(12) United States Patent
Fleck et al.

(10) Patent No.: US 8,623,860 B2
(45) Date of Patent: Jan. 7, 2014

(54) AZETIDINE DERIVATIVES, PHARMACEUTICAL COMPOSITIONS AND USES THEREOF

(71) Applicants: Martin Fleck, Warthausen (DE); Bernd Nosse, Biberach an der Riss (DE); Gerald Juergen Roth, Biberach an der Riss (DE)

(72) Inventors: Martin Fleck, Warthausen (DE); Bernd Nosse, Biberach an der Riss (DE); Gerald Juergen Roth, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/714,525

(22) Filed: Dec. 14, 2012

(65) Prior Publication Data

US 2013/0172316 A1     Jul. 4, 2013

(30) Foreign Application Priority Data

Dec. 30, 2011   (EP) .................................... 11196170

(51) Int. Cl.
| | | |
|---|---|---|
| C07D 205/04 | (2006.01) | |
| C07D 403/04 | (2006.01) | |
| C07D 401/10 | (2006.01) | |
| C07D 405/10 | (2006.01) | |
| C07D 413/14 | (2006.01) | |
| C07D 417/12 | (2006.01) | |
| C07D 417/04 | (2006.01) | |
| C07D 413/12 | (2006.01) | |
| C07D 403/12 | (2006.01) | |
| C07D 401/12 | (2006.01) | |
| C07D 405/12 | (2006.01) | |
| C07D 401/04 | (2006.01) | |
| C07D 498/04 | (2006.01) | |

(52) U.S. Cl.
USPC .............. 514/210.21; 514/210.01; 514/210.2; 544/316; 544/332; 544/122; 544/298; 544/238; 544/255; 544/335; 546/171; 546/268.1; 548/138; 548/248; 548/364.1; 548/518; 548/195; 548/200; 548/267.6; 548/214; 548/236; 548/233

(58) Field of Classification Search
None
See application file for complete search history.

(56) References Cited

U.S. PATENT DOCUMENTS

| | | | |
|---|---|---|---|
| 2008/0274947 A1 | 11/2008 | Jaehne et al. | |
| 2011/0263562 A1 | 10/2011 | Yamashita et al. | |
| 2011/0306587 A1* | 12/2011 | Allen et al. .............. | 514/210.16 |

FOREIGN PATENT DOCUMENTS

| | | |
|---|---|---|
| WO | 03072197 A1 | 9/2003 |
| WO | 2007075629 A2 | 7/2007 |
| WO | 2007143823 A1 | 12/2007 |
| WO | 2010043052 A1 | 4/2010 |
| WO | 2010127212 A1 | 11/2010 |

OTHER PUBLICATIONS

Ito et al., A medium-term rat liver bioassay for rapid in vivo detection of carcinogenic potential of chemicals, 2003, 94, 3-8.*
Abstract in English for JP2006-131559, Date May 25, 2006.
Abstract in English for JP2008-179621, Date Aug. 7, 2008.
Abstract in English for JP2010-043019, Date Feb. 25, 2010.
International Search Report, Form PCT/ISA/210, and Written Opinion, Form PCT/ISA/237, for cooresponding application PCT/EP2012/077027, Date of mailing Mar. 5, 2013.

* cited by examiner

*Primary Examiner* — Jason M Nolan
*Assistant Examiner* — Po-Chih Chen
(74) *Attorney, Agent, or Firm* — Michael P. Morris; Alan R. Stempel

(57) ABSTRACT

The invention relates to new azetidine derivatives of the formula I

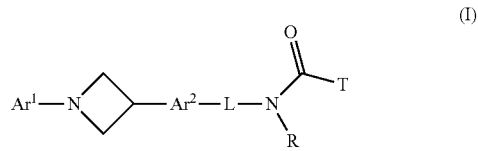

to their use as medicaments, to methods for their therapeutic use and to pharmaceutical compositions containing them.

10 Claims, No Drawings

AZETIDINE DERIVATIVES, PHARMACEUTICAL COMPOSITIONS AND USES THEREOF

FIELD OF THE INVENTION

This invention relates to new compounds, in particular azetidine derivatives, to processes for preparing such compounds, to their use as inhibitors of acetyl-CoA carboxylase(s), to methods for their therapeutic use, in particular in diseases and conditions mediated by the inhibition of acetyl-CoA carboxylase(s), and to pharmaceutical compositions comprising them.

BACKGROUND OF THE INVENTION

Obesity is a major public health issue not only for the EU, USA, Japan but also for the world in general. It is associated with a number of serious diseases including diabetes, dyslipidemia, hypertension, cardiovascular and cerebrovascular diseases. Although the underlying mechanisms are not yet fully understood, the impairment of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G I Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (Saggerson D. Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62(2):237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, nonalcoholic steatohepatitis (NASH) and the metabolic syndrome (L. Tong, H J Harwood Jr. Journal of Cellular Biochemistry 99:1476-1488, 2006; Corbett J W, Harwood J H Jr., Recent Pat Cardiovasc Drug Discov. 2007 November; 2(3):162-80).

Furthermore recent data show that cellular toxicity mediated by lipids (lipotoxicity) is implicated in the susceptibitlity to diabetes associated nephropathy (for review see M Murea, B I Freedmann, J S Parks, P A Antinozzi, S C Elbein, L M Ma; Clin J Am Soc Nephrol. 2010; 5:2373-9). A large-scale genome-wide association study in japanese patients identified single nucleotide polymorphism in the ACC2 gene (ACACB) associated with diabetic nephropathy risk which was replicated in nine independent cohorts. In the kidney, dysregulation of fatty acid metabolism leading to increased fatty acid levels is believed to lead to glomerular and tubular dysfunction (M Murea, B I Freedmann, J S Parks, P A Antinozzi, S C Elbein, L M Ma; Clin J Am Soc Nephrol. 2010; 5:2373-9). Therefore inhibitors targeting ACC as key molecule involved in lipid oxidation have the potential to be beneficial for favorably affecting diabetic nephropathy.

Additionally, insulin resistance, deregulated lipid metabolism, lipotoxicity and increased intramuscular lipids have also been described to play a role in type 1 diabetes (I E Schauer, J K Snell-Bergeon, B C Bergman, D M Maahs, A Kretowski, R H Eckel, M Rewers Diabetes 2011; 60:306-14; P Ebeling, B Essen-Gustaysson, J A Tuominen and V A Koivisto Diabetologia 41: 111-115; K J Nadeau, J G Regensteiner, T A Bauer, M S Brown, J L Dorosz, A Hull, P Zeitler, B Draznin, J E B. Reusch J Clin Endocrinol Metab, 2010, 95:513-521). Therefore ACC inhibitors are also considered as interesting drugs for the treatment of type 1 diabetes.

In addition ACC inhibitors also have the potential to intervene in the progression of diseases that result from the rapid growth of malignant cells or invading organisms that are dependent on endogenous lipid synthesis to sustain their rapid proliferation. De novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao Front Biosci 2010; 2:515-26).

Furthermore in central nervous system disorders including but not limited to Alzheimer's disease, Parkinson disease and epilepsy, impairments in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (S T Henderson Neurotherapeutics, 2008, 5:470-480; L C Costantini, L J Barr, J L Vogel, S T Henderson BMC Neurosci. 2008, 9 Suppl 2:S16; K W Baranano, A L Hartman. Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, AD, hypoxia, ischemia, amyotrophic lateral sclerosis and glioma (L C Costantini, L J Barr, J L Vogel, S T Henderson BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson BMC Neurosci. 2008, 9 Suppl 2:S16; K W Barañano, A L Hartman. Curr Treat Options Neurol. 2008; 10:410-9).

Furthermore, the potential of ACC inhibitors as antifungal agents and as antibacterial agents is well documented (L. Tong, H J Harwood Jr. Journal of Cellular Biochemistry 99:1476-1488, 2006). In addition, ACC inhibitors can be used to combat viral infections. It was discovered recently that viruses rely on the metabolic network of their cellular hosts to provide energy and building blocks for viral replication (Munger J, B D Bennett, A Parikh, X J Feng, J McArdle, H A Rabitz, T Shenk, J D Rabinowitz. *Nat. Biotechnol.* 2008; 26:1179-86). A flux measurement approach to quantify changes in metabolic activity induced by human cytomegalovirus (HCMV) elucidated that infection with HCMV markedly changed fluxes through much of the central carbon metabolism, including glycolysis, tricarboxylic acid cycle and fatty acid biosynthesis. Pharmacological inhibition of fatty acid biosynthesis suppressed the replication of two divergent enveloped viruses (HCMV and influenza A) indicating that fatty acid synthesis is essential for the replication. These examples show that acetyl-CoA fluxes and de novo fatty acid biosynthesis are critical to viral survival and propagation as the newly synthesized fatty acids and phospholipids are important for formation of viral envelopes. Changing the metabolic flux influences the absolute quantity of phospholipid available, the chemical composition and physical properties of the envelope negatively affect viral growth and replication. Hence, ACC inhibitors acting on key enzymes in the fatty acid metabolism, have the potential to be antiviral drugs.

AIM OF THE PRESENT INVENTION

The aim of the present invention is to provide new compounds, in particular new azetidine derivatives, which are active with regard to acetyl-CoA carboxylase(s).

Another aim of the present invention is to provide new compounds, in particular new azetidine derivatives, which are active with regard to ACC2.

A further aim of the present invention is to provide new compounds, in particular new azetidine derivatives, which have an inhibitory effect on acetyl-CoA carboxylase(s) in vitro and/or in vivo and possess suitable pharmacological and pharmacokinetic properties to use them as medicaments.

A further aim of the present invention is to provide new compounds, in particular new azetidine derivatives, which have an inhibitory effect on ACC2 in vitro and/or in vivo and possess suitable pharmacological and pharmacokinetic properties to use them as medicaments.

A further aim of the present invention is to provide effective ACC inhibitors, in particular for the treatment of metabolic disorders, for example of obesity and/or diabetes.

A further aim of the present invention is to provide methods for treating a disease or condition mediated by the inhibition of acetyl-CoA carboxylase(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular azetidine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to acetyl-CoA carboxylase(s).

According to another aspect of the present invention it has been found that the new compounds of general formula (I) as described hereinafter exhibit an inhibiting activity with regard to ACC2.

In a first aspect the present invention provides a compound of general formula (I)

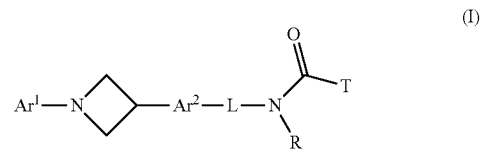

wherein
$Ar^1$ is selected from the group $Ar^1$-G1 consisting of:
  6- to 10-membered aryl and 5- to 10-membered heteroaryl, which are each substituted with one or more substituents $R^1$,
    wherein two substituents $R^1$ linked to adjacent C-atoms of $Ar^1$ together may form a $C_{3-5}$-alkylene bridge, in which 1, 2 or 3 $CH_2$-groups may be replaced by O, C(=O), S, S(=O), S(=O)$_2$, NH or N($C_{1-4}$-alkyl),
    and wherein the alkylene bridge may optionally be substituted by one or two $C_{1-3}$-alkyl groups; while
$R^1$ is selected from the group $R^1$-G1 consisting of:
  H, F, Cl, Br, I, CN, OH, —NC$_2$, $C_{1-6}$-alkyl, $C_{2-6}$-alkenyl, $C_{2-6}$-alkynyl, $C_{3-10}$-carbocyclyl, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{1-6}$-alkyl-S(=O)—, $C_{1-6}$-alkyl-S(=O)$_2$—, $C_{3-10}$-carbocyclyl-S—, $C_{3-10}$-carbocyclyl-$C_{1-3}$-alkyl-S—, $C_{1-4}$-alkyl-C(=O)—, $C_{3-10}$-carbocyclyl-C(=O)—, $R^3R^4N$—, $R^3R^4N$—$C_{2-3}$-alkyl-O—, $R^3R^4N$—C(=O)—, $R^3R^4N$—S(=O)$_2$—, $C_{1-6}$-alkyl-C(=O)—$NR^3$—, $C_{1-6}$-alkyl-S(=O)$_2$—$NR^3$—, $C_{1-6}$-alkyl-C(=O)—$NR^3$—$C_{1-3}$-alkyl-, HO—C(=O)—, $C_{1-6}$-alkyl-O—C(=O)—, heterocyclyl, heterocyclyl-O—, heterocyclyl-$C_{1-3}$-alkyl, heterocyclyl-$C_{1-3}$-alkyl-O—, heterocyclyl-C(=O)—, heterocyclyl-$NR^4$—, aryl, aryl-$C_{1-3}$-alkyl, aryl-O—, aryl-$C_{1-3}$-alkyl-O—, heteroaryl, heteroaryl-$C_{1-3}$-alkyl, heteroaryl-O— and heteroaryl-$C_{1-3}$-alkyl-O—,
  wherein in each carbocyclyl and heterocyclyl a $CH_2$-group may be replaced by —C(=O)—, —C=CH$_2$—, —C=CH($C_{1-6}$-alkyl)- or —C=C($C_{1-6}$-alkyl)$_2$-,
  wherein each carbocyclyl and heterocyclyl may be substituted with one or more $C_{1-4}$-alkyl, which may be substituted with one or more substituents $R^2$,
  wherein each alkyl, carbocyclyl and heterocyclyl may be substituted with one or more substituents $R^2$, wherein each heterocyclyl may be substituted with aryl or heteroaryl, and wherein each aryl and heteroaryl group may be substituted with one or more substituents $R^5$;

$R^2$ is selected from the group $R^2$-G1 consisting of:

F, Cl, Br, CN, OH, $C_{1-4}$-alkyl-O—, $C_{3-7}$-cycloalkyl-O—, $C_{3-7}$-cycloalkyl-$C_{1-3}$-alkyl-O—, $H_2N$—, ($C_{1-4}$-alkyl)NH—, ($C_{1-4}$-alkyl)$_2$N—, $C_{1-4}$-alkyl-C(=O)—, $C_{1-4}$-alkyl-S(=O)$_2$—, HO—C(=O)— and $C_{1-4}$-alkyl-O—C(=O)—, wherein each alkyl or cycloalkyl may be substituted with one or more substituents independently selected from F and OH; and $R^3$ is selected from the group $R^3$-G1 consisting of:

H, $C_{1-6}$-alkyl, $C_{3-10}$-carbocyclyl, $C_{3-10}$-carbocyclyl-$C_{1-3}$-alkyl, $C_{3-6}$-alkenyl, $C_{3-6}$-alkynyl, heterocyclyl, heterocyclyl-$C_{1-3}$-alkyl, aryl, aryl-$C_{1-3}$-alkyl, heteroaryl and heteroaryl-$C_{1-3}$-alkyl, wherein each carbocyclyl and heterocyclyl may be substituted with one or more $C_{1-4}$-alkyl, wherein in each carbocyclyl and heterocyclyl one $CH_2$-group may be replaced by —C(=O)—, wherein each alkyl, carbocyclyl, heterocyclyl, aryl and heteroaryl group may be substituted with one or more substituents $R^5$, $R^4$ is selected from the group $R^4$-G1 consisting of: H and $C_{1-6}$-alkyl; and $Ar^2$ is selected from the group $Ar^2$-G1 consisting of:

phenylene and a 5- or 6-membered monocyclic heteroarylene group containing 1, 2 or 3 heteroatoms independently selected from N, O, or S, wherein each of the groups mentioned above for $Ar^2$ may be substituted with one or more substituents $R^6$; and $R^5$ is selected from the group $R^5$-G1 consisting of F, Cl, Br, CN, OH, $C_{1-4}$-alkyl-, $C_{1-4}$-alkyl-O—, $C_{1-4}$-alkyl-S—, $C_{1-4}$-alkyl-S(=O)$_2$—, $C_{1-3}$-alkyl-O—(C=O)—, $H_2N$—, ($C_{1-4}$-alkyl)NH—, ($C_{1-4}$-alkyl)$_2$N—, $C_{1-4}$-alkyl-C(=O)—NH—, $C_{1-4}$-alkyl-C(=O)—N($C_{1-4}$ alkyl)- and heterocyclyl, wherein each alkyl may be optionally substituted with one or more F-atoms and/or with a substituent selected from OH, $C_{1-3}$-alkyl-O— and CN;

and wherein two substituents $R^6$ attached to an aryl or heteroaryl group together may form a $C_{2-5}$-alkylene bridge, in which 1 or 2-$CH_2$-groups may be replaced by a group independently selected from O, S, NH and N($C_{1-4}$-alkyl)-, and wherein the $C_{2-5}$-alkylene bridge is optionally be substituted by 1 or 2 $C_{1-3}$-alkyl groups;

L is selected from the group L-G1 consisting of:

a straight chain $C_{1-4}$-alkylene group which is optionally substituted with one or more $C_{1-3}$-alkyl or $C_{1-3}$-alkyl-O—$C_{1-3}$-alkyl groups, wherein two alkyl substituents together may form a $C_{1-5}$-alkylene bridge in which 1 or 2-$CH_2$-groups may be replaced by a group independently selected from O, S, NH or N($C_{1-4}$-alkyl)-, and wherein the $C_{1-5}$-alkylene bridge is optionally substituted by 1 or 2 $C_{1-3}$-alkyl groups; and R is selected from the group R-G1 consisting of: H and $C_{1-3}$-alkyl;

T is selected from the group T-G1 consisting of:

$C_{1-6}$-alkyl, $C_{2-6}$-alkenyl, $C_{2-6}$-alkynyl, $C_{3-10}$-carbocyclyl, $C_{3-10}$-carbocyclyl-$C_{1-3}$-alkyl, $C_{1-6}$-alkyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, $C_{1-4}$-alkyl-C(=O)—, $C_{1-4}$-alkyl-S(=O)$_2$—, $R^3R^4$—N—, $R^3R^4$—N—$C_{1-3}$-alkyl-, $R^3R^4$—N—CO—, $C_{1-4}$-alkyl-C(=O)—$R^4N$—$C_{1-3}$-alkyl, heterocyclyl, aryl and heteroaryl, wherein in each carbocyclyl and heterocyclyl a $CH_2$-group may be replaced by —O(=O)—, wherein each carbocyclyl and heterocyclyl may be substituted with one or more $C_{1-4}$-alkyl, which may be substituted with one or more substituents $R^2$, wherein each alkyl, carbocyclyl and heterocyclyl may be substituted with one or more substituents $R^2$, and wherein each aryl and heteroaryl group may be substituted with one or more substituents $R^5$, including any tautomers and stereoisomers thereof, or a salt thereof or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described hereinbefore and hereinafter.

According to another aspect of the invention, there is provided a compound of the general formula (I) or a pharmaceutically acceptable salt thereof for a therapeutic method as described hereinbefore and hereinafter.

In a further aspect this invention relates to a method for treating a disease or condition mediated by the inhibition of acetyl-CoA carboxylase(s) in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of acetyl-CoA carboxylase(s).

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $Ar^1$, $Ar^2$, R, $R^1$, $R^2$, $R^3$, $R^4$, $R^5$, $R^6$ and L, are defined as above and hereinafter. If residues, substituents, or groups occur several times in a compound, as for example $R^3$, $R^4$ or $R^5$, they may have the same or different meanings. Some preferred meanings of individual groups and substituents of the compounds according to the invention will be given hereinafter. Any and each of these definitions may be combined with each other.

$Ar^1$:

$Ar^1$-G1:

The group $Ar^1$ is preferably selected from the group $Ar^1$-G1 as defined hereinbefore and hereinafter.

$Ar^1$-G2:

In one embodiment the group $Ar^1$ is selected from the group $Ar^1$-G2 consisting of: phenyl, naphthyl, thiadiazolyl, pyridinyl, pyrimidinyl, pyridazinyl, pyrazinyl, quinolinyl, oxazolo[4,5-d]pyrimidinyl, benzo[1,3]dioxolyl, 2,3-dihydro-benzo[1,4]dioxinyl and 3,4-dihydro-2H-benzo[b][1,4]dioxepinyl, wherein the before mentioned bicyclic groups preferably are linked to the ring of the core structure of the formula (I) via an aromatic or heteroaromatic ring of the bicyclic group, and wherein all of the before mentioned groups may be optionally substituted with one or more substituents $R^1$.

$Ar^1$-G3:

In another embodiment the group $Ar^1$ is selected from the group $Ar^1$-G3 consisting of: phenyl, thiadiazolyl, pyridinyl, pyrimidinyl, pyridazinyl, quinolinyl, oxazolo[4,5-d]pyrimidinyl, 2,3-dihydro-benzo[1,4]dioxinyl and 3,4-dihydro-2H-benzo[b][1,4]dioxepinyl, wherein each of the beforementioned groups may be substituted with one or two substituents $R^1$.

$Ar^1$-G3a:

In another embodiment the group $Ar^1$ is selected from the group $Ar^1$-G3a consisting of:

phenyl, pyridinyl and pyrimidinyl, wherein each of the beforementioned groups may be substituted with one or two substituents $R^1$.

$Ar^1$-G4:

In another embodiment the group $Ar^1$ is selected from the group $Ar^1$-G4 consisting of:

wherein each group may additionally be substituted with one substituent selected from the group consisting of F, Cl, $CH_3$ and $OCH_3$; and wherein the asterisk of each group indicates the bond which is connected to the azetidine ring of the core structure of the formula (I).

$Ar^1$-G4a:

In another embodiment the group $Ar^1$ is selected from the group $Ar^1$-G4a consisting of:

wherein each group may additionally be substituted with one substituent selected from the group consisting of F and Cl; and wherein the asterisk of each group indicates the bond which is connected to the azetidine ring of the core structure of the formula (I).

Ar¹-G4b:

In another embodiment the group Ar¹ is selected from the group Ar¹-G4b consisting of:

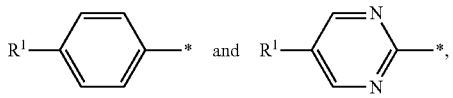

wherein the asterisk of each group indicates the bond which is connected to the azetidine ring of the core structure of the formula (I).

Ar¹-G4c:

In another embodiment the group Ar¹ is selected from the group Ar¹-G4c consisting of:

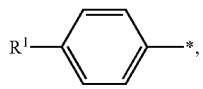

wherein the asterisk indicates the bond which is connected to the azetidine ring of the core structure of the formula (I).

Ar¹-G4d:

In another embodiment the group Ar¹ is selected from the group Ar¹-G4d consisting of:

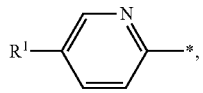

which may additionally be substituted with one substituent selected from the group consisting of F, and wherein the asterisk indicates the bond which is connected to the azetidine ring of the core structure of the formula (I).

Ar¹-G4e:

In another embodiment the group Ar¹ is selected from the group Ar¹-G4e consisting of:

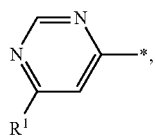

which may additionally be substituted with one substituent selected from the group consisting of F and Cl, and wherein the asterisk indicates the bond which is connected to the azetidine ring of the core structure of the formula (I).

Ar¹-G4f:

In another embodiment the group Ar¹ is selected from the group Ar¹-G4f consisting of:

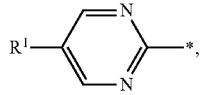

wherein the asterisk indicates the bond which is connected to the azetidine ring of the core structure of the formula (I).

Ar¹-G4g:

In another embodiment the group Ar¹ is selected from the group Ar¹-G4g consisting of:

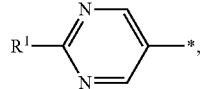

wherein the asterisk indicates the bond which is connected to the azetidine ring of the core structure of the formula (I).

$R^1$:

$R^1$-G1:

The group $R^1$ is preferably selected from the group $R^1$-G1 as defined hereinbefore and hereinafter, $R^1$-G2:

In another embodiment the group $R^1$ is selected from the group $R^1$-G2 consisting of: H, F, Cl, Br, ON, OH, $C_{1-5}$-alkyl, $C_{3-7}$-cycloalkyl, $C_{1-4}$-alkyl-O—, $C_{3-7}$-cycloalkyl-O—, $C_{3-7}$-cycloalkyl-$C_{1-3}$-alkyl-O—, $H_2N$—, pyrrolidino, piperidino, morpholino, thiophenyl, phenyl and phenyl-$CH_2$—, wherein each alkyl and cycloalkyl group may be substituted by one or more F; and wherein in the $NH_2$-group, one or both hydrogen atoms may independently be replaced by $C_{1-4}$-alkyl, $C_{3-7}$-cycloalkyl or $C_{3-7}$-cycloalkyl-$C_{1-3}$-alkyl, wherein each alkyl and cycloalkyl group may be substituted by one or more F; and wherein each phenyl group may be substituted by F, Cl, Br or —$OCH_3$.

$R^1$-G2a:

In another embodiment the group $R^1$ is selected from the group $R^1$-G2a consisting of: H, F, Cl, Br, CN, OH, $C_{1-5}$-alkyl, $C_{3-7}$-cycloalkyl, $C_{1-4}$-alkyl-O—, $C_{3-7}$-cycloalkyl-O—, $C_{3-7}$-cycloalkyl-$C_{1-3}$-alkyl-O—, $H_2N$—, thiophenyl, phenyl and phenyl-$CH_2$—, wherein each alkyl and cycloalkyl group may be substituted by one or more F; and wherein in the $NH_2$-group, one or both hydrogen atoms may independently be replaced by $C_{1-4}$-alkyl, $C_{3-7}$-cycloalkyl or $C_{3-7}$-cycloalkyl-$C_{1-3}$-alkyl, wherein each alkyl and cycloalkyl group may be substituted by one or more F; and wherein each phenyl group may be substituted by F, Cl, Br or —$OCH_3$.

$R^1$-G3:

In another embodiment the group $R^1$ is selected from the group $R^1$-G3 consisting of: F, Cl, Br, $C_{1-4}$-alkyl, $C_{3-5}$-cycloalkyl, $C_{1-4}$-alkyl-O—, $C_{3-6}$-cycloalkyl-O—, $C_{3-5}$-cycloalkyl-$CH_2$—O—, $H_2N$—, thiophenyl and phenyl, wherein each alkyl and cycloalkyl group may be substituted by one to three F; and wherein in the $NH_2$-group, one or both hydrogen atoms may independently be replaced by $C_{1-4}$-alkyl or $C_{3-5}$-cycloalkyl, wherein each alkyl and cycloalkyl group may be substituted by one or more F; and wherein each phenyl group may be substituted by Cl or —$OCH_3$.

$R^1$-G3a:

In another embodiment the group $R^1$ is selected from the group $R^1$-G3a consisting of: F, Br, $CF_3$, $C_{1-4}$-alkyl, $C_{3-5}$-cycloalkyl, $C_{1-4}$-alkyl-O—, $C_{3-6}$-cycloalkyl-O—, $C_{3-5}$-cycloalkyl-$CH_2$—O—, $H_2N$— and phenyl, wherein in the $NH_2$-group, one or two hydrogen atoms may independently be replaced by $C_{1-4}$-alkyl or cyclobutyl, wherein each alkyl group may be substituted by one or more F; and wherein each phenyl group may be substituted by —$OCH_3$.

R¹-G4:
   In another embodiment the group R¹ is selected from the group R¹-G4 consisting of: Br, $CF_3$, $C_{1-4}$-alkyl, cyclopropyl, $C_{1-4}$-alkyl-O—, $C_{3-5}$-cycloalkyl-O—, cyclopropyl-$CH_2$—O—, $H_2N$—, thiophenyl and phenyl,
   wherein in the $NH_2$-group, one or two hydrogen atoms may independently be replaced by $C_{1-4}$-alkyl or cyclobutyl; and
   wherein each alkyl and cycloalkyl group (including the substituents on the $H_2N$— group) may be substituted by one to three F; and
   wherein each phenyl group may be substituted by Cl or —$OCH_3$.

R¹-G5:
   In another embodiment the group R¹ is selected from the group R¹-G5 consisting of: $C_{1-4}$-alkyl-O—, and cyclopropyl-$CH_2$—O,
wherein each alkyl and cyclopropyl group may be substituted by one or more F.

R¹-G5a:
   In another embodiment the group R¹ is selected from the group R¹-G5a consisting of: $C_{1-4}$-alkyl, $C_{1-4}$-alkyl-O—, $C_{3-5}$-cycloalkyl-O— and cyclopropyl-$CH_2$—O—.

R¹-G5b:
   In another embodiment the group R¹ is selected from the group R¹-G5b consisting of: Br, $C_{1-4}$-alkyl, cyclopropyl, cyclopropyl-$CH_2$—O—. and 4-methoxy-phenyl,
wherein each cyclopropyl group may be substituted by one or more F.

R¹-G5c:
   In another embodiment the group R¹ is selected from the group R¹-G5c consisting of:
Br, $C_{1-4}$-alkyl, cyclopropyl and 4-methoxy-phenyl.

R¹-G5d:
   In another embodiment the group R¹ is selected from the group R¹-G5d consisting of:
$CF_3$, cyclobutyl-O—, cyclobutyl-NH— and ($C_{1-4}$-alkyl)NH—.

Ar²:
Ar²-G1:
   The group Ar² is preferably selected from the group Ar²-G1 as defined hereinbefore and hereinafter.

Ar²-G2:
   In another embodiment the group Ar² is selected from the group Ar²-G2 consisting of: phenylene, which may be optionally substituted with one or two substituents R⁵.

Ar²-G2a:
   In another embodiment the group Ar² is selected from the group Ar²-G2a consisting of: phenylene.

Ar²-G3:
   In another embodiment the group Ar² is selected from the group Ar²-G3 consisting of:

wherein the before mentioned group may be optionally substituted with one substituent R⁵.

Ar²-G3a:
   In another embodiment the group Ar² is selected from the group Ar²-G3a consisting of:

L:
L-G1:
   The group L is preferably selected from the group L-G1 as defined hereinbefore and hereinafter.

L-G2:
   In one embodiment the group L is selected from the group L-G2 consisting of: a straight chain $C_{1-4}$-alkylene group which is optionally substituted with one or more $C_{1-3}$-alkyl groups.

L-G2a:
   In one embodiment the group L is selected from the group L-G2a consisting of: a straight chain $C_{1-4}$-alkylene group which is optionally substituted with one $C_{1-3}$-alkyl group.

L-G3:
   In another embodiment the group L is selected from the group L-G3 consisting of: a straight chain $C_{1-3}$-alkylene group which is optionally substituted with one or more methyl groups.

L-G3a:
   In another embodiment the group L is selected from the group L-G3a consisting of: a straight chain $C_{1-3}$-alkylene group which is optionally substituted with one methyl group.

L-G4:
   In another embodiment the group L is selected from the group L-G4 consisting of:

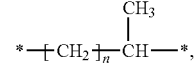

wherein n is 0, 1 or 2, and
wherein the asterisk to the left-hand side is connected to Ar² and the asterisk to the right-hand side is connected to N atom depicted in formula (I).
   Preferably, n is 0 or 1.

L-G4a:
   In another embodiment the group L is selected from the group L-G4a consisting of:

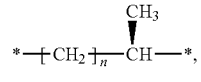

wherein n is 0, 1 or 2, and
wherein the asterisk to the left-hand side is connected to Ar² and the asterisk to the right-hand side is connected to N atom depicted in formula (I).
   Preferably, n is 0 or 1.

L-G4b:
   In another embodiment the group L is selected from the group L-G4b consisting of:

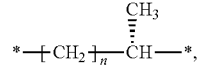

wherein n is 0, 1 or 2, and
wherein the asterisk to the left-hand side is connected to Ar$^2$ and the asterisk to the right-hand side is connected to N atom depicted in formula (I).
  Preferably, n is 0 or 1.
L-G5:
  In another embodiment the group L is selected from the group L-G5 consisting of:

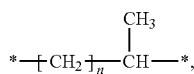

wherein n is 2, and
wherein the asterisk to the left-hand side is connected to Ar$^2$ and the asterisk to the right-hand side is connected to N atom depicted in formula (I).
L-G5a:
  In another embodiment the group L is selected from the group L-G5a consisting of:

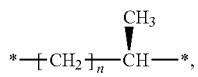

wherein n is 2, and
wherein the asterisk to the left-hand side is connected to Ar$^2$ and the asterisk to the right-hand side is connected to N atom depicted in formula (I).
  L-G5b:
  In another embodiment the group L is selected from the group L-G5b consisting of:

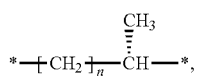

wherein n is 2, and
wherein the asterisk to the left-hand side is connected to Ar$^2$ and the asterisk to the right-hand side is connected to N atom depicted in formula (I).
L-G6:
  In another embodiment the group L is selected from the group L-G6 consisting of:

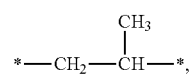

wherein the asterisk to the left-hand side is connected to Ar$^2$ and the asterisk to the right-hand side is connected to N atom depicted in formula (I).
  L-G6a:
  In another embodiment the group L is selected from the group L-G6a consisting of:

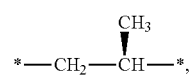

wherein the asterisk to the left-hand side is connected to Ar$^2$ and the asterisk to the right-hand side is connected to N atom depicted in formula (I).

L-G6b:
  In another embodiment the group L is selected from the group L-G6b consisting of:

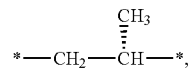

wherein the asterisk to the left-hand side is connected to Ar$^2$ and the asterisk to the right-hand side is connected to N atom depicted in formula (I).
L-G7:
  In another embodiment the group L is selected from the group L-G7 consisting of: —CH(CH$_3$)—.
L-G7a:
  In another embodiment the group L is selected from the group L-G7a consisting of:

wherein the asterisk to the left-hand side is connected to Ar$^2$ and the asterisk to the right-hand side is connected to N atom depicted in formula (I).
L-G7b:
  In another embodiment the group L is selected from the group L-G7b consisting of:

wherein the asterisk to the left-hand side is connected to Ar$^2$ and the asterisk to the right-hand side is connected to N atom depicted in formula (I).
R:
R-G1:
  The group R is preferably selected from the group R-G1 as defined hereinbefore and hereinafter.
R-G2:
  In one embodiment the group R is selected from the group R-G2 consisting of: H and CH$_3$.
R-G3:
  In one embodiment the group R is selected from the group R-G3 consisting of: H.
T:
T-G1:
  The group T is preferably selected from the group T-G1 as defined hereinbefore and hereinafter.
T-G2:
  In one embodiment the group T is selected from the group T-G2 consisting of: C$_{1-4}$-alkyl, —O—(C$_{1-3}$-alkyl), C$_{3-7}$-cycloalkyl, C$_{3-7}$-cycloalkenyl, C$_{2-6}$-alkenyl, C$_{2-6}$-alkinyl, R$^3$, R$^4$—N—, heterocyclyl, heterocyclyl-CH$_2$—, aryl, aryl-CH$_2$—, heteroaryl and heteroaryl-CH$_2$—)
    wherein in each heterocyclyl a —CH$_2$-group may optionally be replaced by —C(=O)—, and
    wherein each alkyl, cycloalkyl, heterocyclyl, aryl and heteroaryl may be optionally substituted with one or more substituents independently selected from R$^5$.

T-G3:

In another embodiment the group T is selected from the group T-G3 consisting of: $C_{1-3}$-alkyl, —O—($C_{1-2}$-alkyl), $C_{3-5}$-cycloalkyl, $C_{3-5}$-cycloalkenyl, $C_{2-6}$-alkenyl, $C_{2-6}$-alkinyl, —NH—($C_{1-2}$-alkyl), —N($C_{1-2}$-alkyl)$_2$, heterocyclyl, phenyl, heteroaryl and heteroaryl-CH$_2$—, wherein in each heterocyclyl a —CH$_2$-group may optionally be replaced by —C(=O)—, and wherein each alkyl, cycloalkyl, heterocyclyl, aryl and heteroaryl may be optionally substituted with one to three groups independently selected from the group consisting of: F, CN, OH, $C_{1-3}$-alkyl-, $C_{1-3}$-alkyl-O—, —$C_{1-3}$-alkyl-O—(C=O)— and CH$_3$—C(=O)—NH—.

T-G3a:

In another embodiment the group T is selected from the group T-G3a consisting of: $C_{1-3}$-alkyl, —O—($C_{1-2}$-alkyl), $C_{3-5}$-cycloalkyl, $C_{3-5}$-cycloalkenyl, $C_{2-6}$-alkenyl, $C_{2-6}$-alkinyl, —NH—($C_{1-2}$-alkyl), —N($C_{1-2}$-alkyl)$_2$, heterocyclyl, phenyl, heteroaryl and heteroaryl-CH$_2$—, wherein the heterocyclyl group is selected from the group consisting of: pyrrolidinyl, tetrahydrofuranyl, piperidinyl, tetrahydropyranyl; and and wherein each heteroaryl group is selected from the group consisting of: pyrrolyl, furanyl, oxazolyl, isoxazolyl, thiazolyl, isothiazolyl, pyrazolyl, imidazolyl, triazolyl, pyridinyl, pyrimidinyl, pyrazinyl and pyridyzinyl; and wherein in each heterocyclyl a —CH$_2$-group may optionally be replaced by —C(=O)—; and wherein each alkyl, cycloalkyl, heterocyclyl, aryl and heteroaryl may be optionally substituted with one to three groups independently selected from the group consisting of: F, CN, OH, $C_{1-3}$-alkyl-, $C_{1-3}$-alkyl-O— and CH$_3$—C(=O)—NH—.

T-G4:

In another embodiment the group T is selected from the group T-G4 consisting of: $C_{1-3}$-alkyl, $C_{3-4}$-cycloalkyl and heteroaryl, wherein the heteroaryl group is selected from the group consisting of: pyrrolyl, furanyl, oxazolyl, isoxazolyl, thiazolyl, isothiazolyl, pyrazolyl, triazolyl, pyridinyl, pyrimidinyl and pyridyzinyl; and wherein each alkyl group may be optionally substituted with one to three F atoms; and wherein each heteroaryl may be optionally substituted with one or two groups independently selected from the group consisting of: CH$_3$, and CH$_3$—C(=O)—NH—.

T-G5:

In another embodiment the group T is selected from the group T-G5 consisting of: $C_{1-3}$-alkyl, —CH$_2$F, —CHF$_2$, —CF$_3$, —CHF—CH$_3$, —CF$_2$CH$_3$, —CH$_2$—OH, —CH$_2$—OCH$_3$, —CH$_2$—OCH$_2$CH$_3$, —CH$_2$—CN, —(CH$_2$)$_2$—CN, —(CH$_2$)$_2$—OH, —(CH$_2$)$_2$—OCH$_3$, —(CH$_2$)$_2$—OCH$_2$CH$_3$, —OCH$_3$, —O—CH$_2$CH$_3$, —CH$_2$—CH=CH$_2$,

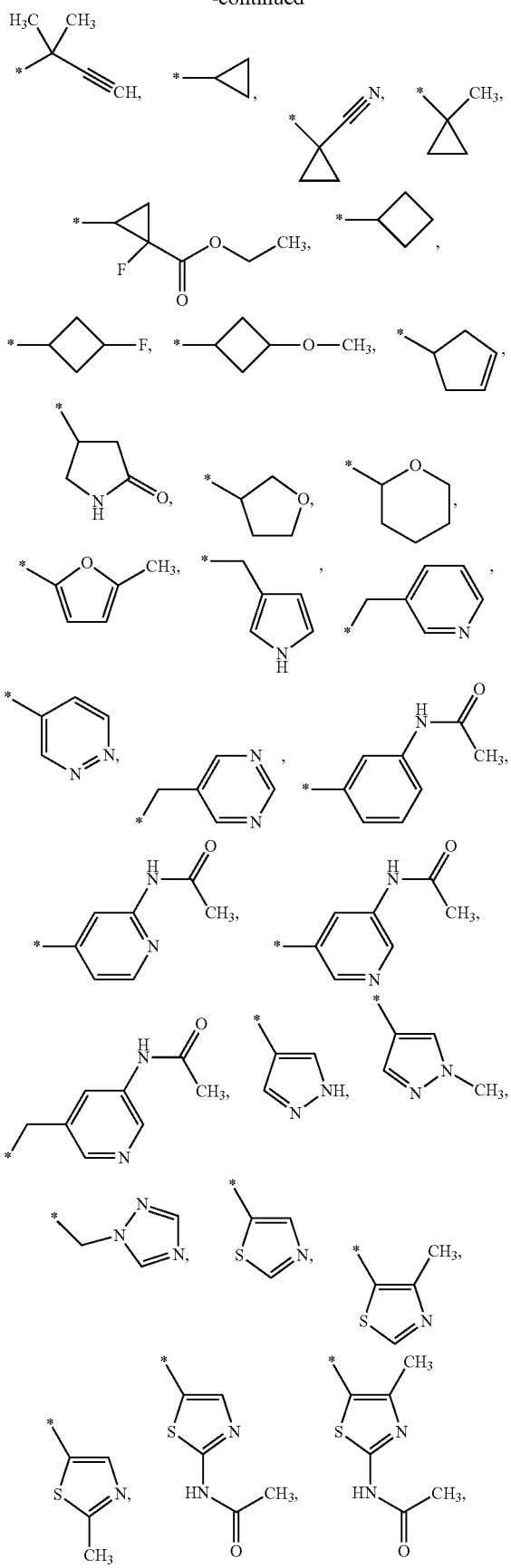

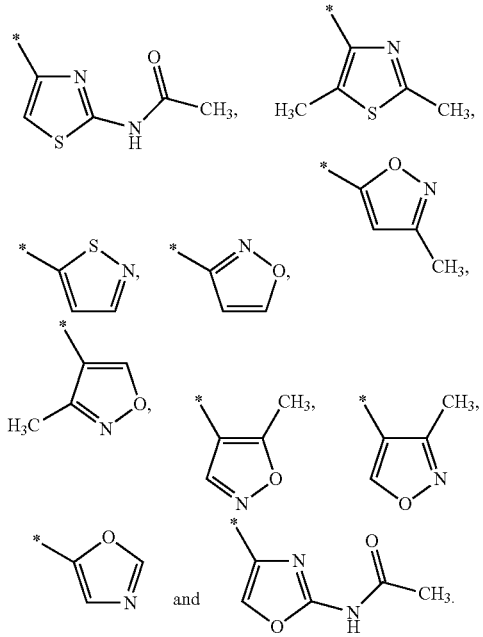

T-G6:
In another embodiment the group T is selected from the group T-G6 consisting of: $CH_3$, cyclopropyl and heteroaryl,
wherein the heteroaryl group is selected from the group consisting of: oxazolyl, isoxazolyl, thiazolyl, isothiazolyl and pyrazolyl; and
wherein each of the before-mentioned heteroaryl group may be optionally substituted with one or two groups independently selected from the group consisting of: $CH_3$, and $CH_3-C(=O)-NH-$.

T-G6a:
In another embodiment the group T is selected from the group T-G6a consisting of: $CH_3$.

$R^2$
$R^2$-G1:
The group $R^2$ is preferably selected from the group $R^2$-G1 as defined hereinbefore and hereinafter.

$R^2$-G2:
In another embodiment the group $R^2$ is selected from the group $R^2$-G2 consisting of: F, Cl, CN, OH, $C_{1-4}$-alkyl-O—, $C_{3-5}$-cycloalkyl-O—, $C_{3-5}$-cycloalkyl-$CH_2$—O—, $H_2N$—, $(C_{1-4}$-alkyl)NH—, $(C_{1-4}$-alkyl)$_2$N— and $C_{1-4}$-alkyl-O—C(=O)—,
wherein each alkyl or cycloalkyl may be substituted with one or more F.

$R^2$-G3:
In another embodiment the group $R^2$ is selected from the group $R^2$-G3 consisting of: F, Cl, $CF_3$, $C_{1-4}$-alkyl-O—, $C_{3-5}$-cycloalkyl-O—, $C_{3-6}$-cycloalkyl-$CH_2$—O—.

$R^3$:
$R^3$-G1:
The group $R^3$ is preferably selected from the group $R^3$-G1 as defined hereinbefore and hereinafter.

$R^3$-G2:
In one embodiment the group $R^3$ is selected from the group $R^3$-G2 consisting of: H, $C_{1-4}$-alkyl, $C_{3-7}$-cycloalkyl, $C_{3-7}$-cycloalkyl-$C_{1-3}$-alkyl, phenyl and phenyl-$C_{1-3}$-alkyl,
wherein each alkyl and cycloalkyl may be optionally substituted with one or more groups independently selected from the group consisting of: F, Cl, Br, ON, OH and —O—($C_{1-4}$-alkyl), and wherein each phenyl group may be optionally substituted with one or more substituents $R^5$.

$R^3$-G3:
In another embodiment the group $R^3$ is selected from the group $R^3$-G3 consisting of: H, $C_{1-4}$-alkyl, $C_{3-6}$-cycloalkyl, $C_{3-7}$-cycloalkyl-$CH_2$—,
wherein each alkyl may be optionally substituted with one or more F.

$R^3$-G4:
In another embodiment the group $R^3$ is selected from the group $R^3$-G4 consisting of: H, $C_{1-4}$-alkyl and $C_{3-6}$-cycloalkyl.

$R^3$-G5:
In another embodiment the group $R^3$ is selected from the group $R^3$-G5 consisting of: $C_{1-4}$-alkyl and $C_{3-5}$-cycloalkyl.

$R^3$-G6:
In another embodiment the group $R^3$ is selected from the group $R^3$-G6 consisting of: butyl and cyclobutyl.

$R^4$
$R^4$-G1:
The group $R^4$ is preferably selected from the group $R^4$-G1 as defined hereinbefore and hereinafter.

$R^4$-G2:
In another embodiment the group $R^4$ is selected from the group $R^4$-G2 consisting of:
H and $CH_3$.

$R^4$-G3:
In another embodiment the group $R^4$ is selected from the group $R^4$-G3 consisting of: H.

$R^5$:
$R^5$-G1:
The group $R^5$ is preferably selected from the group $R^5$-G1 as defined hereinbefore and hereinafter.

$R^5$-G2:
In another embodiment the group $R^5$ is selected from the group $R^5$-G2 consisting of: F, Cl, CN, OH, $C_{1-3}$-alkyl-, $C_{1-3}$-alkyl-O—, $C_{1-3}$-alkyl-O—(C=O)—, $H_2N$—, $(C_{1-3}$-alkyl)NH—, $(C_{1-3}$-alkyl)$_2$N—, $C_{1-3}$-alkyl-C(=O)—NH—, and heterocyclyl;
wherein each alkyl may be optionally substituted with one or more F-atoms and/or a substituent selected from OH, $CH_3$—O— and CN; and
wherein heterocyclyl is defined as hereinbefore and hereinafter or heterocyclyl
preferably denotes a $C_{3-6}$-cycloalkyl ring wherein one or two —$CH_2$-groups are replaced by a group selected from —O—, —NH—, —N($C_{1-3}$-alkyl)-; and
wherein two substituents L attached to adjacent C-atoms of an aryl or heteroaryl group may be linked to each other and form a —O—$CH_2$—$CH_2$—O— or —O—$CH_2$—O— bridging group which is optionally substituted by 1 or 2 $CH_3$— groups.

$R^5$-G3:
In another embodiment the group $R^5$ is selected from the group $R^5$-G3 consisting of: F, Cl, CN, OH, $C_{1-3}$-alkyl-, $C_{1-3}$-alkyl-O—, $CH_3$—C(=O)—NH— and $H_2N$—,
wherein each alkyl may be optionally substituted with one or more F-atoms and/or a substituent selected from OH, $CH_3$—O— and CN.

Examples of preferred subgeneric embodiments according to the present invention are set forth in the following table, wherein each substituent group of each embodiment is defined according to the definitions set forth hereinbefore and wherein all other substituents of the formula (I) are defined according to the definitions set forth hereinbefore:

| Embodiment | R¹ | Ar¹ | Ar² | L | R | T |
|---|---|---|---|---|---|---|
| E-1 | R¹-G1 | Ar¹-G1 | Ar²-G1 | L-G1 | R-G1 | T-G1 |
| E-2 | R¹-G2 | Ar¹-G2 | Ar²-G2 | L-G2 | R-G2 | T-G2 |
| E-3 | R¹-G2 | Ar¹-G2 | Ar²-G2a | L-G2 | R-G2 | T-G3 |
| E-4 | R¹-G3 | Ar¹-G3 | Ar²-G2 | L-G2a | R-G3 | T-G3 |
| E-5 | R¹-G3 | Ar¹-G3 | Ar²-G2a | L-G3 | R-G3 | T-G3 |
| E-6 | R¹-G3a | Ar¹-G3 | Ar²-G2a | L-G3a | R-G3 | T-G4 |
| E-7 | R¹-G3a | Ar¹-G3 | Ar²-G2a | L-G4 | R-G3 | T-G5 |
| E-8 | R¹-G4 | Ar¹-G3 | Ar²-G2a | L-G4 | R-G3 | T-G5 |
| E-9 | R¹-G3 | Ar¹-G3a | Ar²-G2 | L-G2a | R-G3 | T-G3 |
| E-10 | R¹-G3 | Ar¹-G3a | Ar²-G2a | L-G3 | R-G3 | T-G3 |
| E-11 | R¹-G3a | Ar¹-G3a | Ar²-G2a | L-G3a | R-G3 | T-G4 |
| E-12 | R¹-G3a | Ar¹-G3a | Ar²-G2a | L-G4 | R-G3 | T-G5 |
| E-13 | R¹-G4 | Ar¹-G3a | Ar²-G2a | L-G4 | R-G3 | T-G5 |
| E-14 | R¹-G4 | Ar¹-G4 | Ar²-G2a | L-G4 | R-G3 | T-G5 |

The following preferred embodiments of compounds of the formula (I) are described using generic formulae (I.1) to (I.4b), wherein any tautomers and stereoisomers, solvates, hydrates and salts thereof, in particular the pharmaceutically acceptable salts thereof, are encompassed.

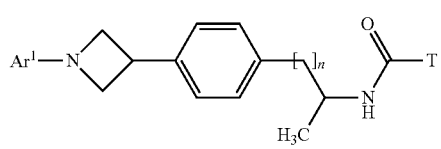
(I.1)

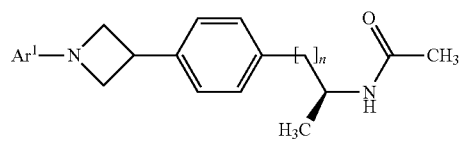
(I.1a)

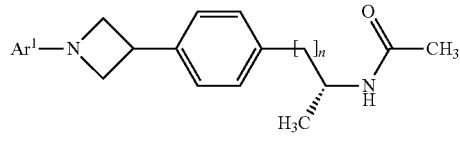
(I.1b)

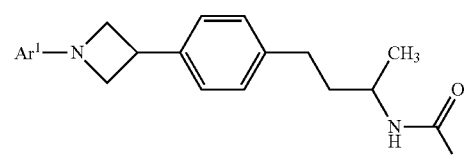
(I.2)

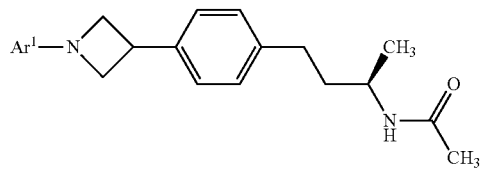
(I.2a)

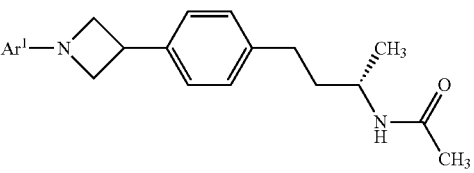
(I.2b)

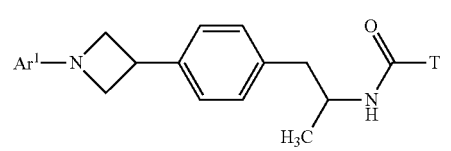
(I.3)

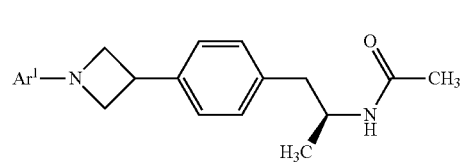
(I.3a)

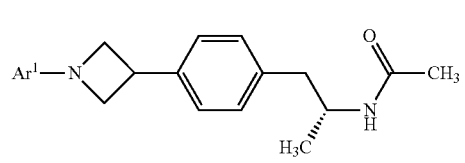
(I.3b)

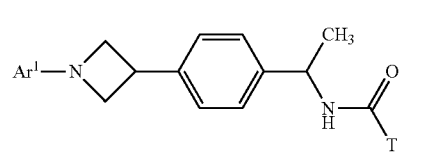
(I.4)

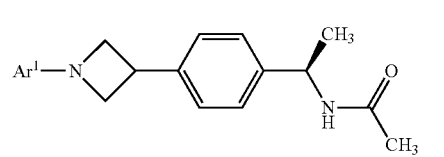
(I.4a)

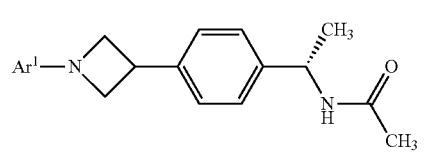
(I.4b)

wherein in each of the above formulae (I.1) to (I.4b), the groups Ar¹ and T are defined as hereinbefore and hereinafter.

A preferred embodiment of the present invention concerns compounds of general formula

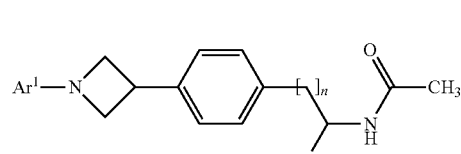
(I.1)

wherein
n is 0, 1 or 2; and
$Ar^1$ is selected from a group consisting of:
phenyl, pyridinyl, pyrimidinyl, pyridazinyl,

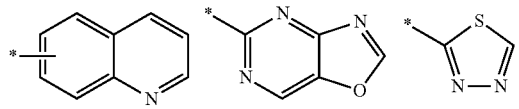

wherein each $Ar^1$ group is optionally substituted by 1 or 2 $R^1$ and
$R^1$ is selected from a group consisting of:
Br, straight-chained or branched $C_{1-4}$-alkyl, cyclopropyl, $C_{1-4}$-alkyl-O—, $C_{3-5}$-cycloalkyl-O—, $C_{3-5}$-cycloalkyl-NH—, cyclopropyl-CH$_2$—O—, $R^3R^4N$, phenyl, thiophenyl,
wherein two $R^1$ groups that are attached to adjacent C-atoms together may form a —O—CH$_2$—CH$_2$—O— or —O—CH$_2$—CH$_2$—CH$_2$—O-bridge,
wherein $R^3$ is H or $C_{1-4}$-alkyl, and
$R^4$ is H or $C_{1-3}$-alkyl,
wherein the phenyl group mentioned for $R^1$ is optionally
substituted by Cl or —O—($C_{1-3}$-alkyl),
and wherein the above-mentioned alkyl groups or cycloalkyl groups may each be substituted by one or more F atoms,
including any tautomers and stereoisomers thereof,
or a salt thereof
or a solvate or hydrate thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably the compounds are obtained analogously to the methods of preparation explained more fully hereinafter, in particular as described in the experimental section.

Synthesis Schemes

Compounds of general formula (I) may be prepared by palladium-mediated Buchwald reactions or copper-mediated Ullmann reactions of aryl halogenides or aryl triflates (II) with azetidines (III) wherein Z is a leaving group which for example denotes Cl, Br, I or OTf (triflate).

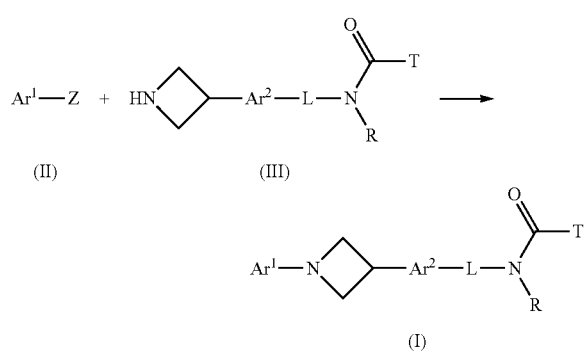

Compounds of general formula (I) may alternatively be prepared by nucleophilic aromatic substitution reactions ($S_NAr$) of aryl/heteroaryl halogenides, aryl/heteroaryl triflates or heteroaryl sulfoxides (II) with azetidines (III), wherein Z is a leaving group which for example denotes Cl, Br, I, S(=O)CH$_3$ or triflate.

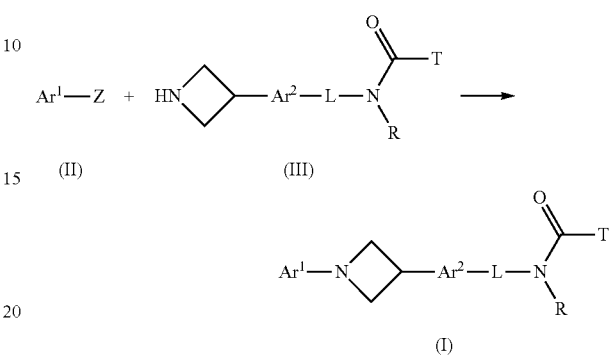

Compounds of general formula (I) may be prepared by amide coupling reactions of amines (IV) with carboxylic acids (V) mediated by coupling reagents such as eg TBTU, HOBt, HATU or CDI.

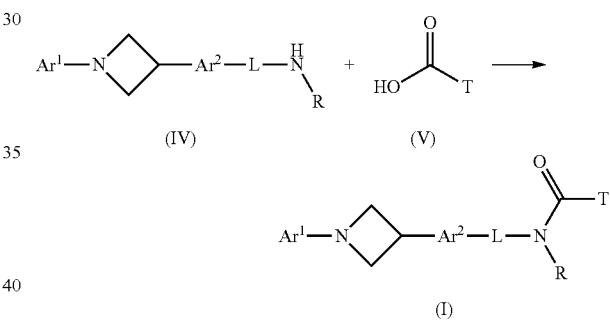

Compounds of general formula (IXa-c) may be prepared by nucleophilic displacement of a leaving group X in (VIa-c) by alcohols (VII) using a suitable base (e.g. NaH), wherein X for example denotes F, Cl or Br. ($R^7$=$R^1$, preferably $R^7$=H, F, Cl, CH$_3$, OCH$_3$; $R^8$=$C_{1-6}$-alkyl-, $C_{3-6}$-alkenyl-, $C_{3-6}$-alkynyl-, $C_{3-10}$-carbocyclyl-, $C_{3-10}$-carbocyclyl-$C_{1-3}$-alkyl-, $R^3R^4N$—$C_{2-3}$-alkyl-, heterocyclyl-, heterocyclyl-$C_{1-3}$-alkyl-, aryl-, aryl-$C_{1-3}$-alkyl-, heteroaryl- and heteroaryl-$C_{1-3}$-alkyl-,
wherein in each carbocyclyl and heterocyclyl a CH$_2$-group may be replaced by —C(=O)—, —C=CH$_2$—, —C=CH($C_{1-6}$-alkyl)- or —C=C($C_{1-6}$-alkyl)$_2$-,
wherein each carbocyclyl and heterocyclyl may be substituted with one or more $C_{1-4}$-alkyl, which may be substituted with one or more substituents $R^2$,
wherein each alkyl, carbocyclyl and heterocyclyl may be substituted with one or more substituents $R^2$, and $R^2$ is as defined above,
wherein each heterocyclyl may be substituted with aryl or heteroaryl, and wherein each aryl and heteroaryl group may be substituted with one or more substituents $R^5$, and $R^5$ is as defined above)

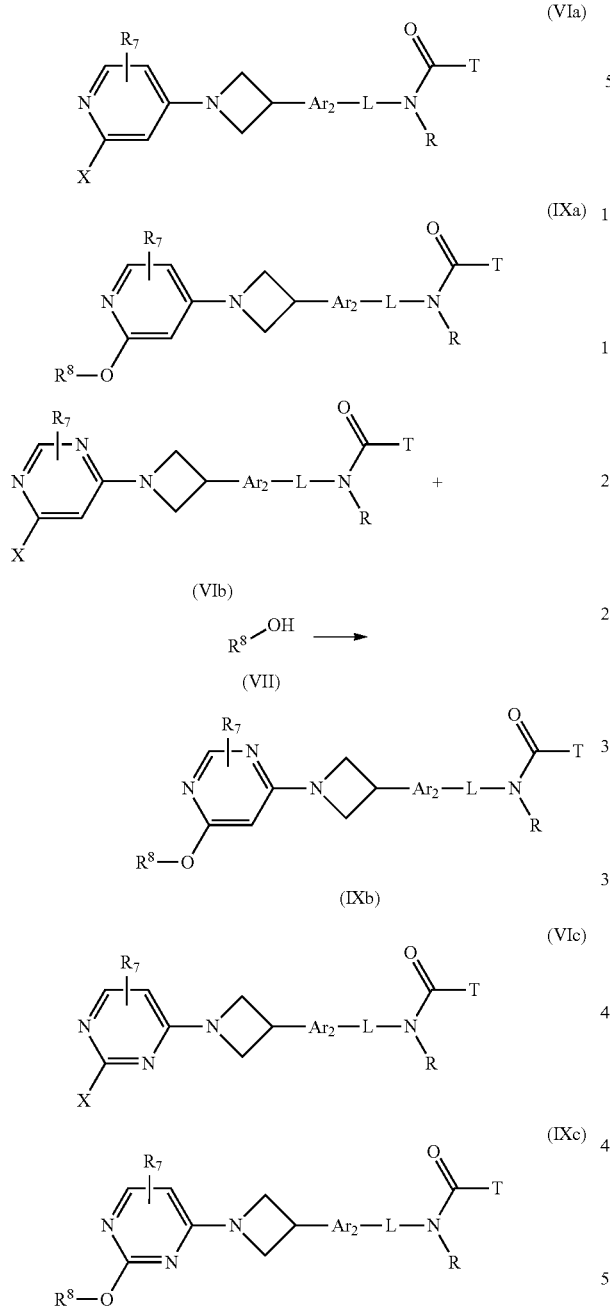
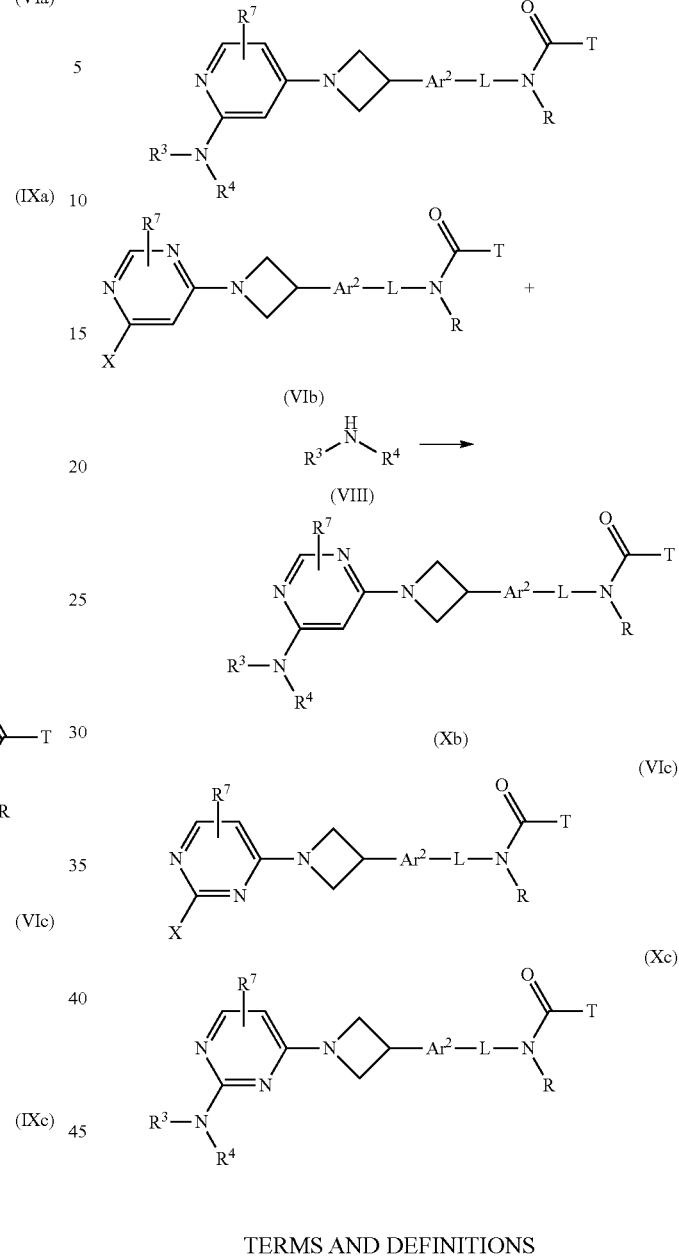

Compounds of general formula (Xa-c) and may be prepared by nucleophilic displacement of a leaving group X in (VIa-c) by amines (VIII), wherein X for example denotes F, Cl or Br.

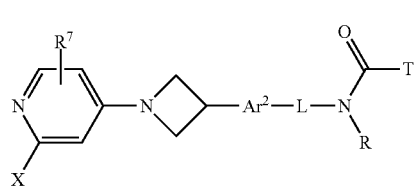

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of acetyl-CoA carboxylase(s) (ACC) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

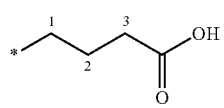

wherein the carboxy group is attached to the third carbon atom of the propyl group. The terms "1-methylpropyl-", "2,2-dimethylpropyl-" or "cyclopropylmethyl-" group represent the following groups:

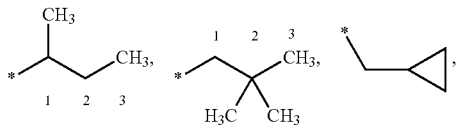

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —($CH_2$)—, —($CH_2$—$CH_2$)—, —($CH(CH_3)$)-, —($CH_2$—$CH_2$—$CH_2$)—, —($C(CH_3)_2$)—, —($CH(CH_2CH_3)$)-, —($CH(CH_3)$—$CH_2$)—, —($CH_2$—$CH(CH_3)$)-, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —$CH$=$CH_2$, —$CH$=$CH$—$CH_3$, —$CH_2$—$CH$=$CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —$CH$=$CH$—, —$CH$=$CH$—$CH_2$—, —$CH_2$—$CH$=$CH$—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —$C$≡$CH$, —$C$≡$C$—$CH_3$, —$CH_2$—$C$≡$CH$.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cylcoalkyl, $C_{3-10}$-cycloalkenyl, octahydropentalenyl, octahydroindenyl, decahydronaphthyl, indanyl, tetrahydronaphthyl. Most preferably the term $C_{3-n}$-carbocyclyldenotes $C_{3-n}$-cylcoalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)$_r$ with r=0, 1 or 2 which in addition may have a carbonyl group. The term "heterocyclyl is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

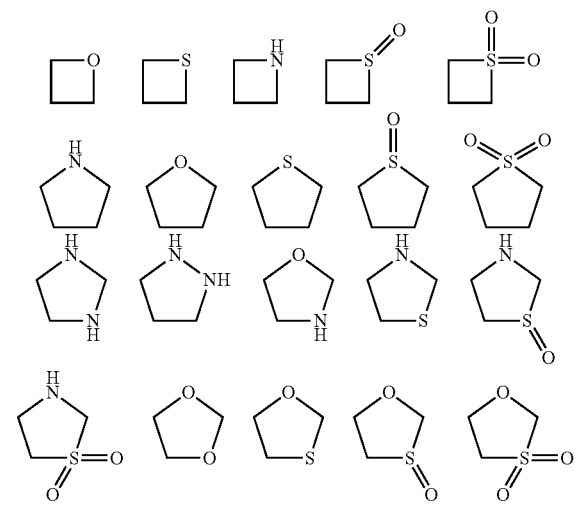

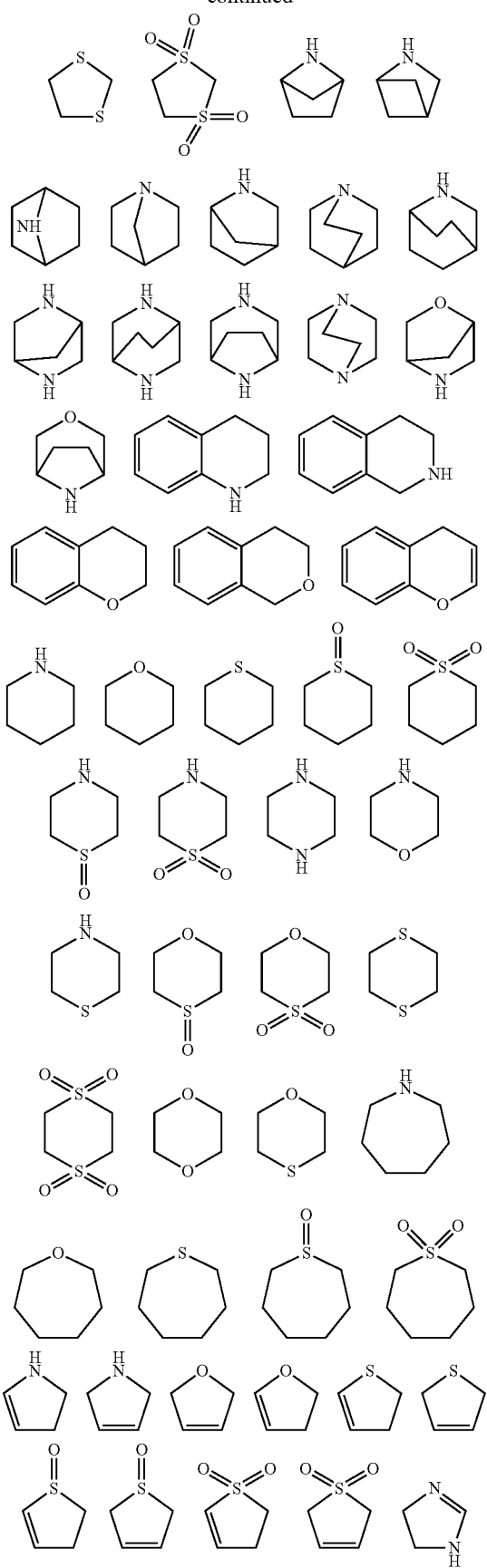
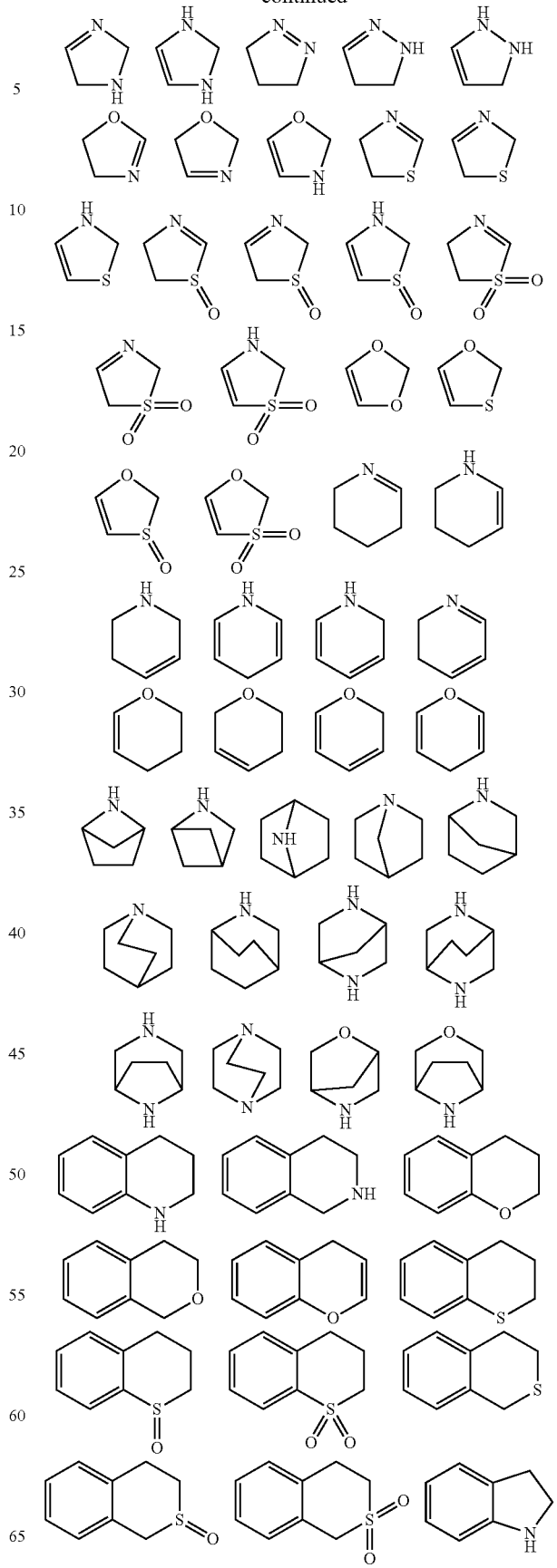

-continued

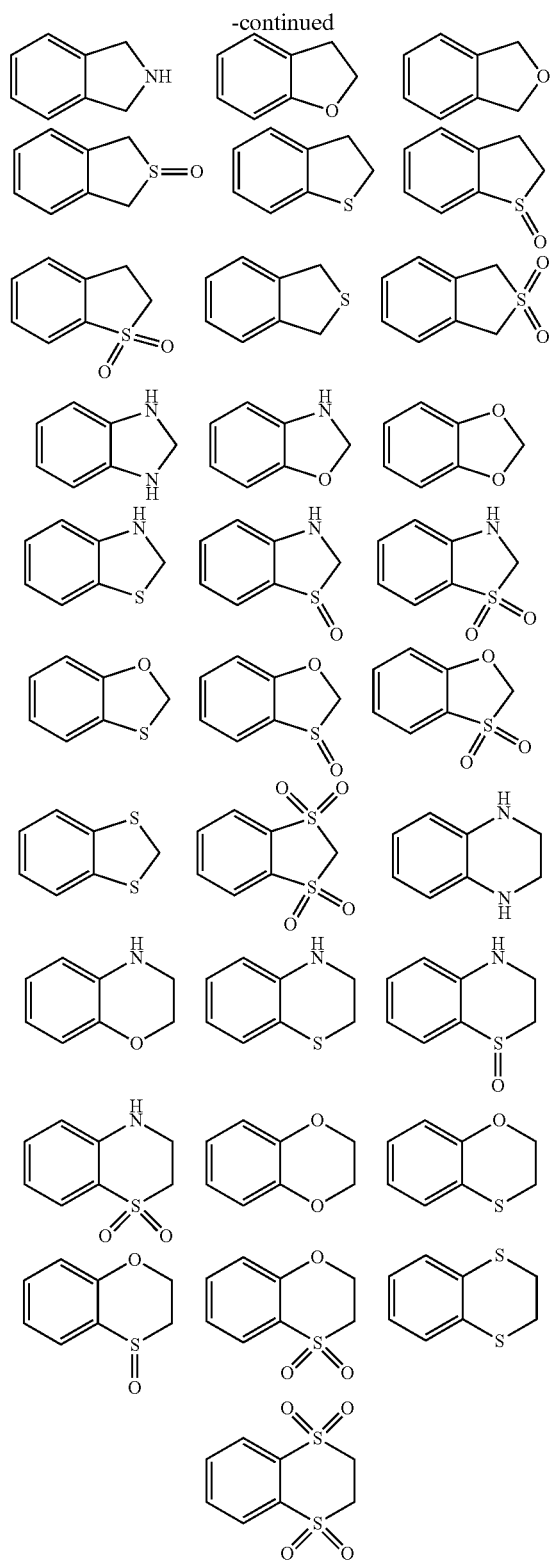

The term "heteroaryl" means a mono- or polycyclic, preferably mono- or bicyclic-ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

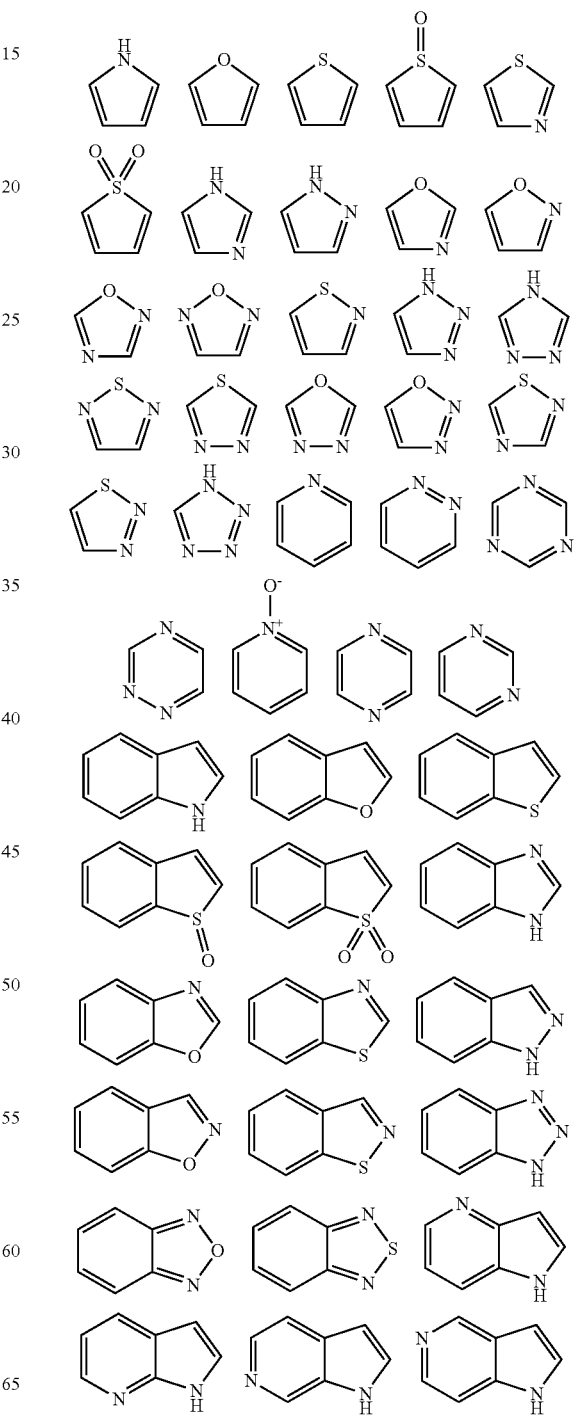

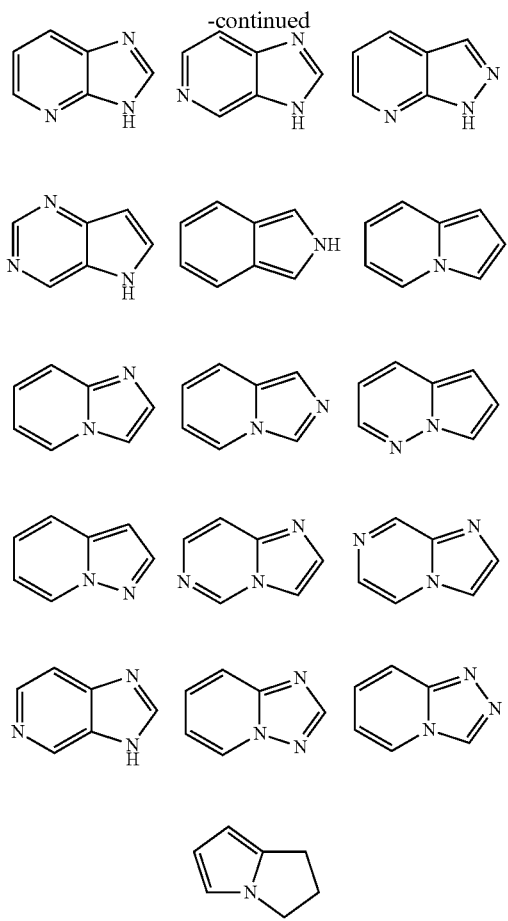

Many of the terms given above may be used repeatedly in the definition of a formula or group and in each case have one of the meanings given above, independently of one another.

Pharmacological Activity

The activity of the compounds of the invention may be demonstrated using the following ACC2 assay:

Spectrophotometric 384 Well Assay

Malonyl CoA formation by acetyl CoA carboxylases is stoichiometrically linked to the consumption of ATP. ACC2 activity is measured in a NADH-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM $KHCC_3$, 10 mM $MgCl_2$, 0.5 mg/ml BSA, 3.75 mM reduced L-glutathione, 15 U/ml lactate dehydrogenase, 0.5 mM phosphoenolpyruvate, 15 U/ml pyruvate kinase, compounds at different concentrations at final DMSO concentrations of 1%.

The enzymatic reaction is then started by addition of a mixture of NADH, acetyl Coenzyme A (both 200 µM f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW').

The slope S is used for calculation of % CTL=(S(compound)−S('LOW'))/(S('HIGH')−S('LOW'))*100. Compounds will give values between 100% CTL (no inhibition) and 0% CTL (complete inhibition).

For $IC_{50}$ value determination, the sample slope in the presence of the test compound after subtraction of the low controls (S(compound)−S('LOW')) are used.

An $IC_{50}$ value is derived from the compound slopes at different dosages after subtraction of the low controls (S(compound)−S('LOW')) by non-linear regression curve fitting (equation $y=(A+((B-A)/(1+((C/x)^D))))$).

The compounds of general formula (I) according to the invention for example have $IC_{50}$ values below 10000 nM, particularly below 1000 nM, preferably below 300 nM.

In the following table the activity expressed as $IC_{50}$ (µM) of compounds according to the invention is presented wherein the $IC_{50}$ values are determined in the ACC2 assay as described hereinbefore. The term "Ex." refers to the example numbers according to the following experimental section.

| Example | ACC2 [µM] | Example | ACC2 [µM] | Example | ACC2 [µM] |
|---|---|---|---|---|---|
| 1.01 | 0.51 | 3.02 | 1.06 | 3.53 | 2.38 |
| 1.02 | 0.26 | 3.03 | 0.38 | 3.54 | 2.36 |
| 1.03 | 0.34 | 3.04 | 0.25 | 3.55 | 1.33 |
| 1.04 | 0.63 | 3.05 | 1.73 | 3.56 | 0.70 |
| 1.05 | 0.90 | 3.06 | 1.07 | 3.57 | 1.65 |
| 1.06 | 3.81 | 3.07 | 2.58 | 3.58 | 3.01 |
| 1.07 | 5.63 | 3.08 | 3.07 | 3.59 | 0.78 |
| 1.08 | 0.65 | 3.09 | 2.51 | 3.60 | 1.17 |
| 1.09 | 2.73 | 3.10 | 0.89 | 3.61 | 2.52 |
| 1.10 | 8.10 | 3.11 | 1.45 | 3.62 | 2.91 |
| 1.11 | 0.60 | 3.12 | 2.73 | 3.63 | 1.22 |
| 1.12 | 0.61 | 3.13 | 2.97 | 3.64 | 2.46 |
| 1.13 | 0.95 | 3.14 | 1.77 | 3.65 | 1.18 |
| 1.14 | 0.67 | 3.15 | 1.05 | 3.66 | 0.97 |
| 1.15 | 0.48 | 3.16 | 3.05 | 3.67 | 1.68 |
| 1.16 | 0.41 | 3.17 | 2.79 | 3.68 | 1.00 |
| 1.17 | 0.19 | 3.18 | 3.05 | 3.69 | 2.40 |
| 1.18 | 3.18 | 3.19 | 2.88 | 3.70 | 1.02 |
| 1.19 | 1.13 | 3.20 | 1.02 | 3.71 | 1.69 |
| 1.20 | 0.49 | 3.21 | 2.96 | 3.72 | 1.97 |
| 1.21 | 0.34 | 3.22 | 2.58 | 3.73 | 2.49 |
| 1.22 | 2.08 | 3.23 | 2.65 | 3.74 | 0.96 |
| 1.23 | 0.38 | 3.24 | 1.67 | 3.75 | 3.08 |
| 1.24 | 1.63 | 3.25 | 3.01 | 3.76 | 2.82 |
| 1.25 | 0.54 | 3.26 | 2.42 | 3.77 | 1.70 |
| 1.26 | 0.51 | 3.27 | 2.86 | 3.78 | 1.22 |
| 1.27 | 0.17 | 3.28 | 1.21 | 3.79 | 2.30 |
| 1.28 | 0.68 | 3.29 | 1.67 | 3.80 | 2.44 |
| 1.29 | 0.78 | 3.30 | 2.06 | 3.81 | 1.40 |
| 1.30 | 0.74 | 3.31 | 1.64 | 3.82 | 1.62 |
| 1.31 | 0.60 | 3.32 | 1.76 | 3.83 | 3.13 |
| 1.32 | 9.04 | 3.33 | 2.87 | 3.84 | 3.60 |
| 1.33 | 0.18 | 3.34 | 2.73 | 3.85 | 0.36 |
| 1.34 | 0.83 | 3.35 | 1.46 | 3.86 | 0.45 |
| 1.35 | 0.18 | 3.36 | 2.19 | 3.87 | 0.47 |
| 2.01 | 8.56 | 3.37 | 1.17 | 3.88 | 0.53 |
| 2.02 | 3.79 | 3.38 | 1.41 | 3.89 | 0.55 |
| 2.03 | 7.02 | 3.39 | 1.52 | 3.90 | 0.62 |
| 2.04 | 2.56 | 3.40 | 1.31 | 3.91 | 0.63 |
| 2.05 | 0.81 | 3.41 | 2.07 | 4.1 | 1.82 |
| 2.06 | 1.42 | 3.42 | 0.94 | 4.2 | 1.01 |
| 2.07 | 0.34 | 3.43 | 2.57 | 4.3 | 1.51 |
| 2.08 | 0.32 | 3.44 | 1.13 | 5.1 | 1.45 |
| 2.09 | 0.45 | 3.45 | 1.87 | 5.2 | 1.22 |

-continued

| Example | ACC2 [μM] | Example | ACC2 [μM] | Example | ACC2 [μM] |
|---|---|---|---|---|---|
| 2.10 | 0.47 | 3.46 | 1.15 | 5.3 | 1.59 |
| 2.11 | 7.76 | 3.47 | 2.70 | 5.4 | 0.68 |
| 2.12 | 0.42 | 3.48 | 1.10 | 5.5 | 0.38 |
| 2.13 | 0.69 | 3.49 | 1.69 | 5.6 | 0.54 |
| 2.14 | 1.31 | 3.50 | 2.17 | 5.7 | 0.40 |
| 2.15 | 0.85 | 3.51 | 2.18 | | |
| 3.01 | 0.33 | 3.52 | 0.71 | | |

In view of their ability to inhibit acetyl-CoA carboxylase(s), the compounds of general formula (I) according to the invention and the corresponding salts thereof are theoretically suitable for the treatment, including preventative treatment of all those diseases or conditions which may be affected or which are mediated by the inhibition of acetyl-CoA carboxylase(s), in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase(s), in particular ACC2, in a patient, preferably in a human.

In yet another aspect the present invention relates a method for treating, including preventing a disease or condition mediated by the inhibition of acetyl-CoA carboxylase(s) in a mammal that includes the step of administering to a patient, preferably a human, in need of such treatment a therapeutically effective amount of a compound of the present invention, or a pharmaceutical composition thereof.

Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as is hyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, micro-albuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or greater.

According to another aspect the compounds of the present invention are particularly suitable for treating, including preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:
A. disorders of fatty acid metabolism and glucose utilization disorders; disorders in which insulin resistance is involved;
B. hepatic disorders and conditions related thereto, including:
    fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;
C. skin disorders and conditions and those associated with polyunsaturated fatty acids, such as
    eczema, acne, sebaceous gland diseases, psoriasis, keloid scar formation or prevention, other diseases related to mucous membrane fatty acid composition;
D. primary hypertriglyceridemia or secondary hypertriglyceridemias following familial histiocytic reticulosis, lipoprotein lipase deficiency, hyperlipo-proteinemias, apolipoprotein deficiency (e.g. apoCII or apoE deficiency);
E. diseases or conditions related to neoplastic cellular proliferation, for example benign or malignant tumors, cancer, neoplasias, metastases, carcinogenesis;
F. diseases or conditions related to neurological, psychiatric or immune disorders or conditions;
G. other diseases or conditions in which inflammatory reactions, cell differentiation and/or other ACC-mediated aspects may for example be involved are:
    atherosclerosis such as, for example (but not restricted thereto), coronary sclerosis including angina pectoris or myocardial infarction, stroke, ischemic, stroke and transient ischemic attack (TIA),
    peripheral occlusive disease,
    vascular restenosis or reocclusion,
    chronic inflammatory bowel diseases such as, for example, Crohn's disease and ulcerative colitis,
    pancreatitis,
    sinusitis,
    retinopathy, ischemic retinopathy,
    adipose cell tumors,
    lipomatous carcinomas such as, for example, liposarcomas, solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc., tumors in which ACC is up regulated, acute and chronic myeloproliferative disorders and lymphomas, angiogenesis neurodegenerative disorders including Alzheimer's disease, multiple sclerosis, Parkinson's disease, epilepsy, erythemato-squamous dermatoses such as, for example, psoriasis, acne vulgaris, other skin disorders and dermatological conditions which are modulated by PPAR, eczemas and neurodermatitis, dermatitis such as, for example, seborrheic dermatitis or photodermatitis, keratitis and keratoses such as, for example, seborrheic keratoses, senile keratoses, actinic keratoses, photo-induced keratoses or keratosis follicularis, keloids and keloid prophylaxis, bacterial infections, fungal infections, warts, including condylomata or condylomata acuminate viral infections such as, for example, human hepatitis B virus (HBV), hepatitis C virus (HCV), West Nile virus (WNV) or Dengue virus, human Immunodeficiency virus (HIV), poxvirus and Vaccinia virus (VV), HCMV, influenza A, human papilloma viral (HPV). venereal papillomata, viral warts such as, for example, molluscum contagiosum, leukoplakia, papular dermatoses such as, for example, lichen planus, skin cancer such as, for example, basal-cell carcinomas, melanomas or cutaneous T-cell lymphomas, localized benign epidermal tumors such as, for example, keratoderma, epidermal naevi, chilblains;

high blood pressure, polycystic ovary syndrome (PCOS), asthma, cystic fibrosis, osteoarthritis, lupus erythematosus (LE) or inflammatory rheumatic disorders such as, for example rheumatoid arthritis, vasculitis, wasting (cachexia), gout, ischemia/reperfusion syndrome, acute respiratory distress syndrome (ARDS)

viral diseases and infections lipodystrophy and lipodystrophic conditions, also for treating adverse drug effect;

myophathies and lipid myopathis (such as carnitine palmitoyltransferase I or II deficiency);

H. formation of muscles and a lean body or muscle mass formation.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11 beta-hydroxy steroid dehydrogenase-1 (11 beta-HSD type 1) inhibitors, stearoyl-CoA desaturase-1 (SCD-1) inhibitors, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-Y antagonists (e.g., NPY Y5 antagonists), $PY_{Y3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, GOAT (Ghrelin O-Acyltransferase) inhibitors, histamine 3 antagonists or inverse agonists, neuromedin U agonists, MTP/ApoB inhibitors (e.g., gut-selective MTP inhibitors), opioid antagonists, orexin antagonists, and the like.

Preferred anti-obesity agents for use in the combination aspects of the present invention include gut-selective MTP inhibitors CCKa agonists, 5HT2c agonists, MCR4 agonists, lipase inhibitors, opioid antagonists, oleoyl-estrone, obinepitide, pramlintide (Symlin®), tesofensine (NS2330), leptin, liraglutide, bromocriptine, orlistat, exenatide (Byetta®), AOD-9604 (CAS No. 221231-10-3) and sibutramine.

Suitable anti-diabetic agents include sodium-glucose co-transporter (SGLT) inhibitors, 11beta-hydroxy steroid dehydrogenase-1 (11 beta-HSD type 1) inhibitors, phosphodiesterase (PDE) 10 inhibitors, diacylglycerol acyltransferase (DGAT) 1 or 2 inhibitors, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, an alpha-amylase inhibitors (e.g., tendamistat, trestatin and AL-3688), alpha-glucoside hydrolase inhibitors (e.g., acarbose), alpha-glucosidase inhibitors (e.g., adiposine, camiglibose, emiglitate, miglitol, voglibose, pradimicin-Q, and salbostatin), PPAR gamma agonists (e.g., balaglitazone, ciglitazone, darglitazone, englitazone, isaglitazone, pioglitazone, rosiglitazone and troglitazone), PPAR alpha/gamma agonists (e.g., CLX-0940, GW-1536, GW-20 1929, GW-2433, KRP-297, L-796449, LR-90, MK-0767 and SB-219994), biguanides (e.g., metformin), GLP-1 derivatives, glucagon-like peptide 1 (GLP-1) agonists (e.g., Byetta™, exendin-3 and exendin-4), GLP-1 receptor and glucagon receptor co-agonists, glucagon receptor antagonists, GIP receptor antagonists, protein tyrosine phosphatase-1 B (PTP-1 B) inhibitors (e.g., trodusquemine, hyrtiosal extract), SIRT-1 activators (e.g. reservatrol), dipeptidyl peptidease IV (DPP-IV) inhibitors (e.g., sitagliptin, vildagliptin, alogliptin, linagliptin and saxagliptin), insulin secretagogues, GPR119 agonists, GPR40 agonists, TGR5 agonists, MNK2 inhibitors, GOAT (Ghrelin O-Acyltransferase) inhibitors, fatty acid oxidation inhibitors, A2 antagonists, c-jun amino-terminal kinase (JNK) inhibitors, insulins, insulin derivatives, fast acting insulins, inhalable insulins, oral insulins, insulin mimetics, glycogen phosphorylase inhibitors, VPAC2 receptor agonists and glucokinase activators.

Preferred anti-diabetic agents are metformin, glucagon-like peptide 1 (GLP-1) agonists (e.g., Byetta™), GLP-1 receptor and glucagon receptor co-agonists, sodium-glucose co-transporter (SGLT) inhibitors, 11beta-hydroxy steroid dehydrogenase-1 (11beta-HSD type 1) inhibitors and DPP-IV inhibitors (e.g. sitagliptin, vildagliptin, alogliptin, linagliptin and saxagliptin).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of the acetyl-CoA carboxylase(s), in particular ACC2, in particular diseases or conditions as described hereinbefore and hereinafter.

In yet another aspect the present invention relates a method for treating, including preventing a disease or condition mediated by the inhibition of acetyl-CoA carboxylase(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

EXAMPLES

The Examples that follow are intended to illustrate the present invention without restricting it. The terms "ambient temperature" and "room temperature" are used interchangeably and designate a temperature of about 20° C.

Preliminary Remarks:

As a rule, 1H-NMR and/or mass spectra have been obtained for the compounds prepared. The $R_f$ values are determined using Merck silica gel 60 $F_{254}$ plates and UV light at 254 nm.

Experimental Part

The following abbreviations are used above and hereinafter:

| | |
|---|---|
| aq. | aqueous |
| ACN | acetonitrile |
| AcOH | acetic acid |
| BOC | tert-butoxy-Carbonyl- |
| Cbz | Benzyloxycarbonyl- |
| CDI | N,N-carbonyldiimidazole |
| CDT | N,N-carbonylditriazole |
| CyH | cyclohexane |
| DBAD | di-tert-butyl azodicarboxylate |
| DCM | dichloromethane |
| DIAD | diisopropyl azodicarboxylate |
| DIBAlH | diisobutyl aluminium hydride |
| DIPE | diisopropyl ether |
| DIPEA | N,N-diisopropylethylamine |
| DMA | N,N-dimethylacetamide |
| DMAP | 4-dimethylaminopyridine |
| DMF | N,N-dimethylformamide |
| DMSO | dimethyl sulfoxide |
| EI-MS | electron induced mass spectrometry |
| ESI-MS | electrospray ionisation mass spectrometry |
| EtOAc | ethyl acetate |
| EtOH | ethanol |
| Ex | example |
| FA | formic acid |
| GC | gas chromatography |
| HATU | 2-(1H-7-azabenzotriazol-1-yl)-1,1,3,3-tetramethyluronium hexafluorophosphate |

-continued

| | |
|---|---|
| HOBt | N-hydroxybenzotriazole |
| HPLC | high performance liquid chromatography |
| iPrOH | iso-propanol |
| LAH | lithium aluminium hydride |
| MeOH | methanol |
| m.p. | melting point |
| MsCl | methanesulfonyl chloride |
| n.d. | not determined |
| NMP | N-methyl-2-pyrrolidone | the mixture is stirred again for 3.5 h. After complete reaction, the mixture is filtrated. The residue is washed with MeOH and the solvent of the filtrate is removed in vacuo. The crude product is used without further purification.

$C_9H_{12}BrN$ (M=214.1 g/mol)

ESI-MS: 214 $[M+H]^+$

Rf (TLC): 0.3 (silica gel, DCM/MeOH 9/1)

The following compounds are prepared analogously to example 1.1

| Ex. | Starting material | Product structure | Mass spec result | TLC retention factor (method) |
|---|---|---|---|---|
| I.1 | | | 214 $[M + H]^+$ | 0.3 (silica gel; DCM/MeOH 9/1) |
| I.2 | | | 228 $[M + H]^+$ | n.d. |

-continued

| | |
|---|---|
| org. | organic |
| Pd/C | palladium on activated carbon |
| PE | petroleum ether |
| PG | protecting group |
| r.t. | room temperature (about 20° C.) |
| sat. | saturated |
| SFC | supercritical fluid chromatography |
| TBME | tert-butyl methyl ether |
| TEA | triethylamine |
| TF/TFA | trifluoroacetic acid |
| THF | tetrahydrofuran |
| TBAF | tetrabutylammonium fluoride |
| TBTU | 2-(1H-benzotriazol-1-yl)-1,1,3,3-tetramethyluronium tetrafluoroborat |
| TMS | trimethylsilyl |
| Ts | 4-toluenesulfonyl |
| X-Phos | 2-dicyclohexylphosphino-2',4',6'-triisopropylbiphenyl |

Preparation of Starting Compounds

Example I

Example 1.1 (General Route)

1-(4-Bromophenyl)propane-2-amine

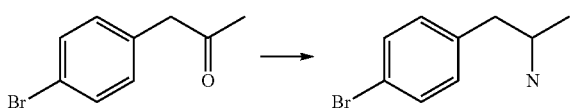

A mixture of 25.0 g (0.12 mol) 4-bromophenylacetone and 400 mL 7N ammonia in MeOH is charged with 1.20 g Raney nickel. The mixture is stirred in an hydrogen atmosphere (15 psi) at r.t. over night. Again 0.6 g Raney nickel are added and Example II Example II.1 (General Route)

N-(1-(4-Bromophenyl)propan-2-yl)acetamide

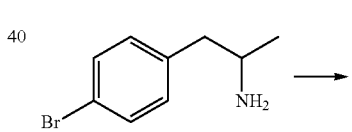

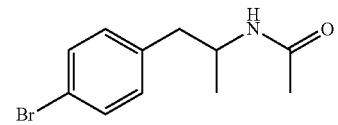

17.0 mL (179.7 mmol) acetic anhydride are added to a mixture of 24.2 g (113 mmol) 1-(4-bromophenyl)propane-2-amine and 20 mL AcOH and the reaction mixture is stirred at r.t. over night. The solvent is evaporated in vacuo, and the residue partitonated between TBME and a saturated aq. NaHCO₃ solution. The layers are separated and the organic layer is washed with water, dried with $Na_2SO_4$, filtered and the solvent is removed in vacuo. The crude product is triturated with DIPE.

$C_{11}H_{14}BrNO$ (M=256.1 g/mol)

ESI-MS: 256 $[M+H]^+$ $R_t$ (HPLC): 2.60 min (method B)

The following compounds are prepared analogously to example II.1.

| Ex. | Starting material | Product structure | Mass spec result | HPLC retention time (method) |
|---|---|---|---|---|
| II.1 | | | 256 [M + H]$^+$ | 2.60 (B) |
| II.2 | | | 242 [M + H]$^+$ | 2.47 (B) |
| II.3 | | | 270 [M + H]$^+$ | 2.11 (A) |
| II.4 | | | 242 [M + H]$^+$ | 1.65 (A) |

Example III

Example III.1 (General Route)

N-(1-(4-iodophenyl)propan-2-yl)acetamide

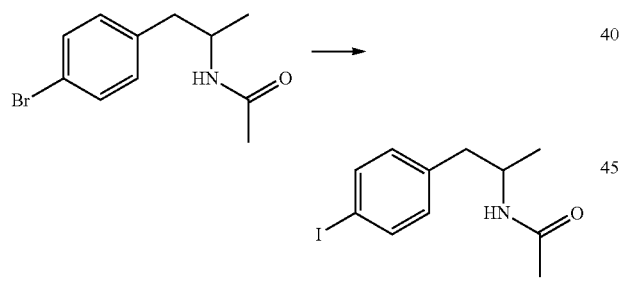

To 6.00 g (23.4 mmol) N-(1-(4-bromophenyl)propan-2-yl)acetamide (II.1) in 65 mL dioxan are added 0.45 g (2.34 mmol) CuI, 0.50 mL (4.70 mmol) N,N''-dimethyl-ethylendiamine and 7.02 g (46.9 mmol) NaI. The reaction mixture is stirred at 120° C. for 70 h. The mixture is allowed to cool to r.t. and half of the solvent is removed in vacuo. EtOAc and diluted aq. ammonia solution are added and the layers are separated. The aq. layer is once more extracted with EtOAc. The organic layers are combined, dried with Na$_2$SO$_4$, filtered and the solvent is removed in vacuo. The crude product is triturated with diethylether and dried at 50° C. in vacuo.

$C_{11}H_{14}INO$ (M=303.1 g/mol)

ESI-MS: 304 [M+H]$^+$

R$_t$ (HPLC): 2.85 min (method B)

The following compounds are prepared analogously to example III.1

For examples III.2-3 the reaction mixture is stirred at 120° C. over night.

| Ex. | Starting material | Product structure | Mass spec result | HPLC retention time (method) |
|---|---|---|---|---|
| III.1 | | | 304 [M + H]$^+$ | 2.85 (B) |

| Ex. | Starting material | Product structure | Mass spec result | HPLC retention time (method) |
|---|---|---|---|---|
| III.2 | 4-Br-C6H4-CH2CH2-CH(CH3)-NHC(O)CH3 | 4-I-C6H4-CH2CH2-CH(CH3)-NHC(O)CH3 | 318 [M + H]+ | 2.17 (A) |
| III.3 | 4-Br-C6H4-CH(CH3)-NHC(O)CH3 | 4-I-C6H4-CH(CH3)-NHC(O)CH3 | 290 [M + H]+ | 2.55 (B) |
| III.4 | (S)-4-Br-C6H4-CH(CH3)-NHC(O)CH3 | (S)-4-I-C6H4-CH(CH3)-NHC(O)CH3 | 290 [M + H]+ | TLC: R_f = 0.57 (silica gel, DCM/MeOH 9/1) |

Example IV
Example IV.1 (General Route)
N-(1-(4-iodophenyl)propan-2-yl)acetamide

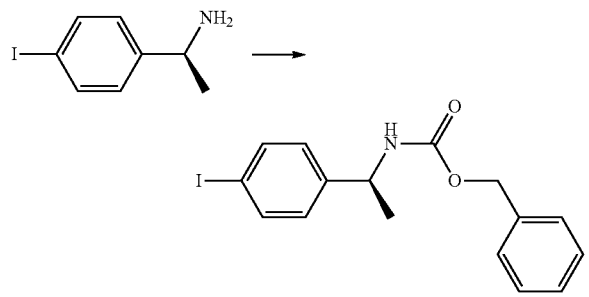

To 51.4 g (0.208 mol) (S)-1-(4-iodophenyl)ethanamine in a mixture of $H_2O$/THF (1:1, 1200 mL) are added 86 g $K_2CO_3$ (0.62 mol) and 48.2 g CbzCl (0.31 mol) and the mixture is stirred at room temperature over night. The reaction mixture is extracted with EtOAc. The organic layer is dried, concentrated and purified by flash chromatography (PE/EtOAc 5/1).

$C_{16}H_{16}INO_2$ (M=381.0 g/mol)
ESI-MS: 382 $[M+H]^+$
$R_f$(TLC): 0.6 (silica gel, PE/EtOAc 2/1)

The following compounds are prepared analogously to example IV.1

| Ex. | Starting material | Product structure | Mass spec result | TLC R_f-value (silica gel) |
|---|---|---|---|---|
| IV.1 | (S)-4-I-C6H4-CH(CH3)-NH2 | (S)-4-I-C6H4-CH(CH3)-NHC(O)OCH2Ph | 382 [M + H]+ | 0.6 PE/EtOAc 2/1 |
| IV.2 | 4-I-C6H4-CH2-CH(CH3)-NH2 | 4-I-C6H4-CH2-CH(CH3)-NHC(O)OCH2Ph | 396 [M + H]+ | 0.5 (PE/EtOAc 5/1) |

Example V

Example V.1 (General Route)

tert-Butyl 3-(4-(2-acetamidopropyl)phenyl)azetidine-1-carboxylate

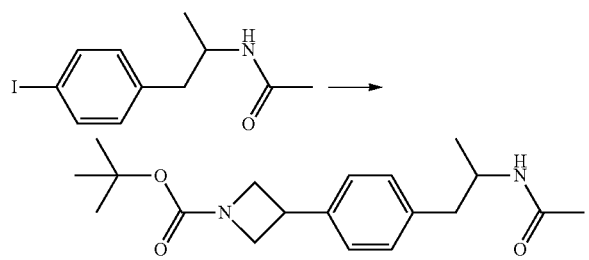

300 mg (7.07 mmol) LiCl are placed in a schlenk tube and heated up for about 5 min with a heat gun in vacuo. After cooling down to r.t. the tube is flushed with argon and 0.61 g (9.33 mmol) zinc dust are added and the mixture is again heated up for 10 min in vacuo with a heat gun, cooled down to r.t. and flushed with argon again. Then 6.50 mL THF and 0.03 mL (0.33 mmol) dibromoethane are added and the mixture is degassed thoroughly. The mixture is warmed to 70° C., stirred for 10 min and cooled down to r.t. 10 μl (66 μmol) TMSCl are added and the mixture is stirred for 20 min before 2.00 g (7.06 mmol) 1-BOC-3-iodoazetidine are added and stirring is continued for 16 h. This mixture is added to a thoroughly degassed mixture of 1.74 g (5.74 mmol) of example III.1, 0.33 g (0.36 mmol) $Pd_2dba_3$ and 0.08 g (0.36 mmol) tri-(2-furyl)-phosphine in 7 mL THF. After degassing for one more time the resulting mixture is stirred at 70° C. for 1.5 h. Then the mixture is pulled on a sat. aq. $NH_4Cl$ solution and extracted three times with EtOAc. The organic layers are combined, dried with $MgSO_4$, filtered and the solvent is removed in vacuo. The crude product is purified by column chromatography (silica gel, DCM/MeOH 100/0 92/8 and PE/EtOAc 50/50→20/80).

$C_{13}H_{28}N_2O_3$ (M=332.4 g/mol)
ESI-MS: 333 $[M+H]^+$
$R_t$ (HPLC): 1.93 min (method A)

The following compounds are prepared analogously to example V.1

For the examples V.2-V.4 the crude product is purified by HPLC.

For the examples V.5 and V.6 the zincation and the Negishi reaction is done in DMA as solvent and with $PdCl_2(dppf)$ and CuI as catalysts.

Example VI

Example VI.1 (general route)

N-(1-(4-(Azetidin-3-yl)phenyl)propan-2-yl)acetamide

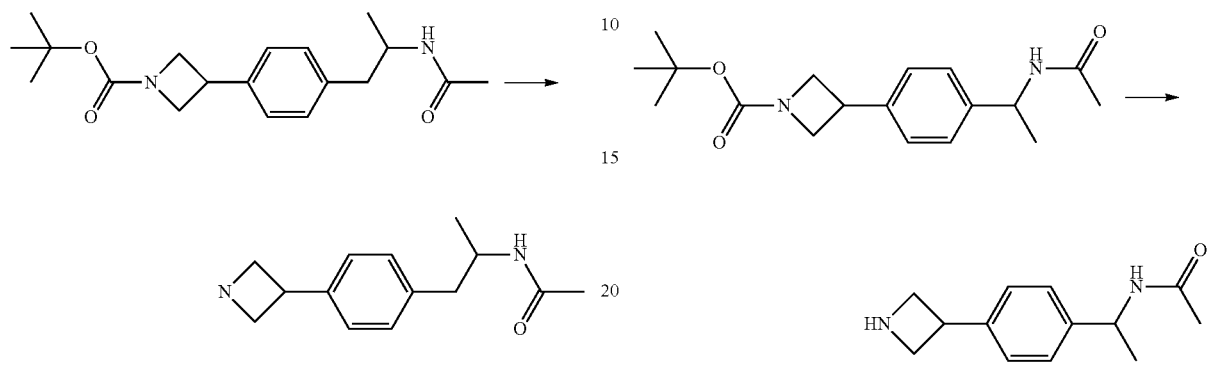

To 3.30 g (9.93 mmol) of the BOC-protected amine V.1 in 30 mL MeOH are added 31.8 mL (39.7 mmol) HCl (c=1.25 mol/L in MeOH). The reaction mixture is stirred at 35° C. for 8 h. The solvent is removed in vacuo and the residue is purified by HPLC (MeOH/H$_2$O/NH$_3$).

$C_{14}H_{20}N_2O$ (M=232.3 g/mol)
ESI-MS: 233 [M+H]+
R$_t$ (HPLC): 1.27 min (method A)

The following compounds are prepared analogously to example V.1

For the examples VI.2 and VI.3 the reaction conditions are 2 h at r.t. and the reaction mixture is neutralised with aq. NaOH solution before removing the solvent.

Example VII

Example VII.1 (General Route)

N-(1-(4-(azetidin-3-yl)phenyl)ethyl)acetamide

To 1.20 g (3.77 mmol) of the BOC-protected amine IV.3 in 10 mL DCM are added 1.5 mL TFA. The reaction mixture is stirred at r.t. over night. One additional ml TFA is added and stirring is continued for 5 h. The solvent is removed in vacuo and the residue is purified by HPLC (MeOH/H$_2$O/NH$_3$).

$C_{13}H_{18}N_2O$ (M=218.3 g/mol)
ESI-MS: 219 [M+H]+
R$_t$ (HPLC): 0.87 min (method A)

| Ex. | Starting material | Product structure | Mass spec result | HPLC retention time (method) |
|---|---|---|---|---|
| VI.1 | V.1 | | 233 [M + H]+ | 1.27 (A) |
| VI.2 | V.2 | | 247 [M + H]+ | 1.71 (A) |
| VI.3 | V.4 | | 219 [M + H]+ | 1.20 (A) |

The following compounds are prepared analogously to example VII.1

| Ex. | Starting material | Product structure | Mass spec result | HPLC retention time (method) |
|---|---|---|---|---|
| VII.1 | V.3 | | 219 [M + H]⁺ | 0.87 (A) |
| VII.2 | V.5 | | n.d. | TLC: $R_f$ = 0.1 (silica gel, DCM/MeOH 10/1) |
| VII.3 | V.6 | | n.d. | TLC: $R_f$ = 0.0 (silica gel, PE/EtOAc 3/1) |

Example VIII

Example VIII.1 (General Route)

1-Bromo-4-cyclopropylmethoxybenzene

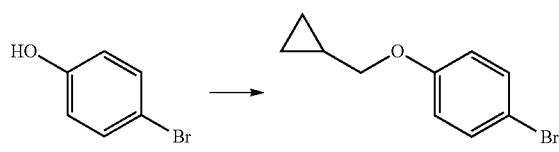 [SMILES: Oc1ccc(Br)cc1 ; Brc1ccc(OCC2CC2)cc1]

5.0 g (28.9 mmol) 4-bromophenol, 3.93 g (43.4 mmol) (chloromethyl)cyclopropane and 7.99 g (57.8 mmol) $K_2CO_3$ are added to 10 mL DMF and stirred at 80° C. over night. Afterwards the reaction mixture is diluted with water and extracted with DCM. The organic layer is dried with $MgSO_4$, filtered and the solvent is removed in vacuo.

$C_{10}H_{11}BrO$ (M=227.1 g/mol)

EI-MS: 226/228 [M]⁺

$R_t$ (HPLC): 8.16 min (method J)

The following compounds are prepared analogously to example VIII.1 For example VIII.2 the reaction temperature is 120° C.

| Ex. | Starting material | Starting material | Product structure | Mass spec result | HPLC retention time (method) |
|---|---|---|---|---|---|
| VIII.1 | | | | 226.228 [M]⁺ | 8.16 (J) |
| VIII.2 | | | | 226.228 [M]⁺ | 4.90 (Q) |
| VIII.3 | | | | n.d. | 9.01 (J) |
| VIII.4 | | | | 244/246 [M]⁺ | 2.12 (A) |

| Ex. | Starting material | Starting material | Product structure | Mass spec result | HPLC retention time (method) |
|---|---|---|---|---|---|
| VIII.5 | 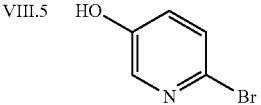 | 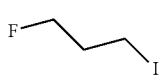 | 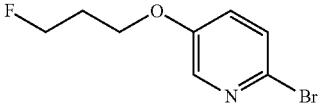 | 234/436 [M]+ | 0.90 (K) |

Example IX

1-Bromo-4-(2-bromoethoxy)benzene

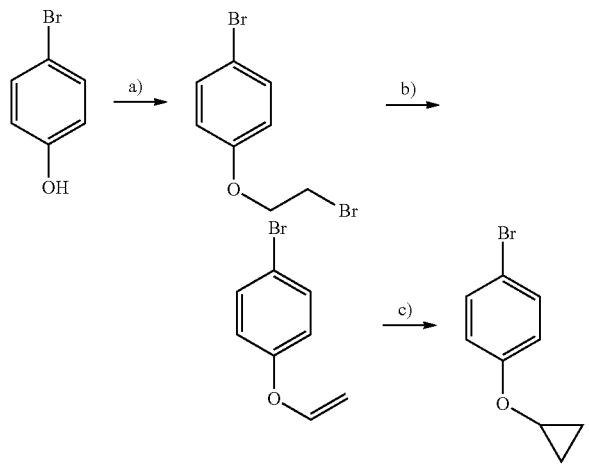

a) 55.0 g (318 mmol) 4-bromophenol and 14.1 g (352 mmol) NaOH are added to 110 mL water. 41.1 mL (477 mmol) dibromoethane are added slowly and the reaction mixture is stirred for 16 h under reflux. Afterwards the reaction mixture is extracted with DCM and the solvent is removed in vacuo. The crude product is purified by column chromatography (silica gel, CyH/EtOAc 4/1).

b) 52.0 g (186 mmol) of 1-bromo-4-(2-bromoethoxy)benzene is added to 300 mL THF and cooled down to 0° C. Within 30 min 25.0 g (223 mmol) KOtBu are added to this mixture in several portions. Cooling is removed and the reaction mixture is stirred at r.t. over night. The reaction is quenched by the addition of water. The resulting mixture is extracted with EtOAc (2×). The org. phases are combined, washed with sat. aq. NaCl solution, dried with MgSO$_4$, filtered and the solvent is removed in vacuo. The resulting product is used without further purification.

c) 39.0 g (176 mmol) of 1-bromo-4-vinyloxybenzene and 32.4 mL (441 mmol) chloroiodomethane are added to 500 mL dichloroethane and cooled down to 0° C. During 1 h 200 mL (200 mmol) diethylzinc solution (c=1 mol/L in hexane) are added and stirring is continued for 2 h at 0° C. The reaction is quenched by the addition of 200 mL of a sat. aq. NH$_4$Cl solution and extracted with TBME (2×). The org. phases are combined, washed with sat. aq. NaCl solution, dried with MgSO$_4$, filtered and the solvent is removed in vacuo. The crude product is purified by column chromatography (silica gel, PE).

C$_9$H$_9$BrO (M=213.1 g/mol)
EI-MS: 212/214 [M]+
R$_f$ (TLC): 0.4 (silica gel, PE)

Example X

5-Bromo-2-cyclobutoxy-pyrimidine

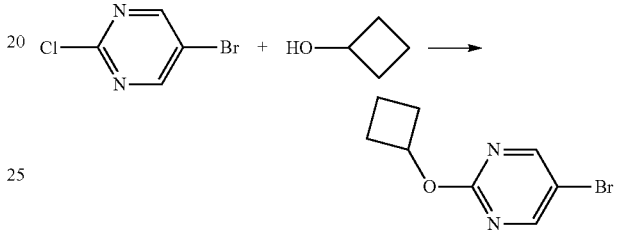

2.42 mL (31.0 mmol) cyclobutanol and 3.00 g (15.5 mmol) 5-bromo-2-chloro-pyrimidine are added to 40 mL dioxane and cooled down to 0° C. Then the reaction mixture is charged with 1.86 g (46.5 mmol) NaH. After removing of the cooling bath the reaction mixture is stirred at r.t. for 1 h. The reaction is quenched by the addition of water and sat. aq. NaHCO$_3$ solution. The dioxane is removed in vacuo and the aq. residue is extracted with DCM. The org. phases are combined, washed with water, dried with MgSO$_4$ and filtered. The solvent is removed under reduced pressure. The crude product is used without further purification.

C$_9$H$_{11}$BrN$_2$O (M=229.1 g/mol)
ESI-MS: 229/231 [M+H]+
R$_f$ (TLC) 1.95 (method A)

Example XI

5-Bromo-N-cyclobutylpyrimidin-2-amine

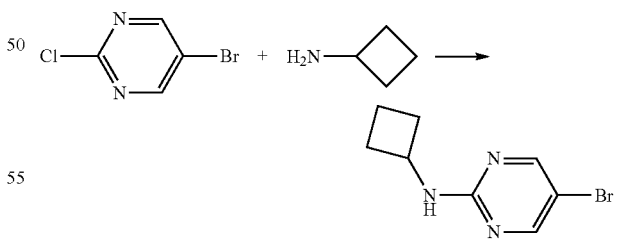

In a sealed tube 2.00 g (10.3 mmol) 5-bromo-2-chloropyrimidine, 1.15 mL (13.4 mmol) cyclobutylamine and 2.70 mL (15.5 mmol) DIPEA are added to 12 mL ACN. The reaction mixture is stirred at 50° C. over night, then diluted with EtOAc and washed with water (2×). The org. phase is dried with MgSO$_4$, filtered and the solvent is removed in vacuo.

C$_8$H$_{10}$BrN$_3$ (M=228.1 g/mol)
ESI-MS: 228/230 [M+H]+
R$_f$ (TLC): 1.87 (method A)

Example XII

5-Bromo-N-sec-butylpyrimidin-2-amine

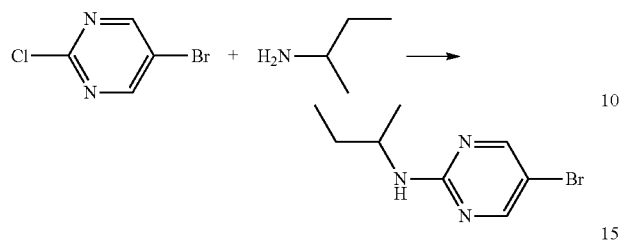

In a sealed tube 2.00 g (10.3 mmol) 5-bromo-2-chloropyrimidine and 3.13 mL (31.0 mmol) sec-butylamin are added to 12 mL ACN. The reaction mixture is stirred at 120° C. for 2 h, then diluted with EtOAc and washed with water (2×). The org. phase is dried with MgSO$_4$, filtered and the solvent is removed in vacuo.

$C_8H_{12}BrN_3$ (M=228.1 g/mol)
ESI-MS: 230/232 [M+H]$^+$
$R_f$ (TLC): 1.93 (method A)

Example XIII

2-Chloro-5-cyclopropylpyrimidine

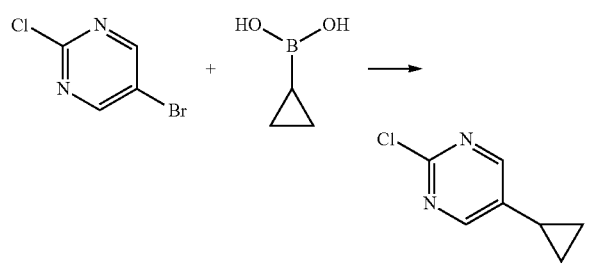

3.60 g (18.6 mmol) 5-bromo-2-chloropyrimidine, 4.80 g (55.8 mmol) cyclopropyl boronic acid, 13.8 g (65.1 mmol) K$_3$PO$_4$, 568 mg (2.03 mmol) tricyclohexylphosphine and 4 mL water are added to 80 mL toluene. The mixture is degassed thoroughly and charged with 627 mg (2.79 mmol) Pd(OAc)$_2$. After degassing again the mixture is stirred at 100° C. over night, filtered and the solvent is removed in vacuo. The crude product is purified by column chromatography (silica gel, PE/EtOAc 90/10 70/30).

$C_7H_7ClN_2$ (M=154.6 g/mol)
EI-MS: 155 [M+H]$^+$
$R_t$ (HPLC): 1.34 (method A)

Example XIV

Example XIV.1 (General Route)

5-Chloro-2-phenyloxazolo[5,4-d]pyrimidine

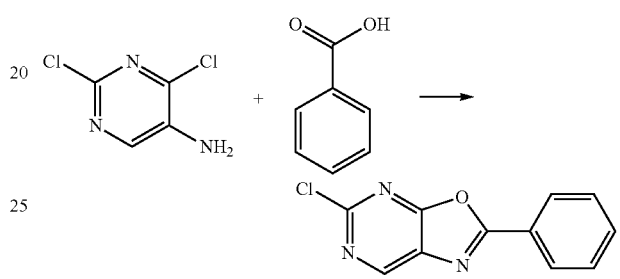

7.82 g (64.0 mmol) benzoic acid and 20 mL POCl$_3$ are stirred together at 100° C. for 30 min. Within 45 min 7.00 g (42.7 mmol) 2,6-dichloro-5-aminopyrimidine are added by several portions. The reaction mixture is stirred for additional 2 h at the same temperature. After that the mixture is carefully added to an ice cold aq. NaOH solution. The resulting precipitate is filtered, washed with water and dried.

$C_{11}H_6ClN_3O$ (M=231.6 g/mol)
EI-MS: 232 [M+H]+
$R_t$ (HPLC): 2.22 (method S)

The following compounds are prepared analogously to example XIV.1.

For the example XIV.2 the solvent of the reaction mixture is removed in vacuo and the residue is triturated first with diethylether, then dissolved in DCM, filtered and the solvent is removed in vacuo again. The residue is one more time triturated with diethylether.

| Ex. | Starting material | Product structure | Mass spec result | HPLC retention time method) |
|---|---|---|---|---|
| XIV.1 | benzoic acid | 5-chloro-2-phenyloxazolo[5,4-d]pyrimidine | 232 [M + H]$^+$ | 2.22 (S) |
| XIV.2 | thiophene-3-carboxylic acid | 5-chloro-2-(thiophen-3-yl)oxazolo[5,4-d]pyrimidine | 238 [M + H]$^+$ | 1.43 (S) |

Example XV 3-(4-chlorophenyl)-6-iodopyridazine

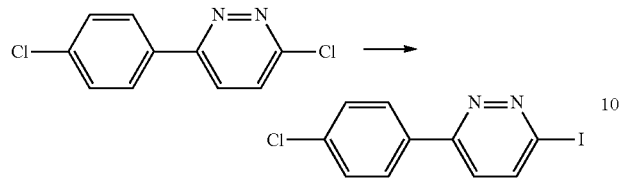

20 ml ACN are added to 0.50 g (1.11 mmol) 3-(4-chlorophenyl)-6-chloropyridazine and 3.33 g (22.2 mmol) NaI before 189 µl fuming conc. HCl are added and the mixture is stirred at 80° C. for 4 h. The mixture is alkalised with aq. Ammonia solution (32%) diluted with water and extracted with EtOAc. The org. phases are combined, dried with Na$_2$SO$_4$ and the solvent is removed in vacuo. The resulting crude product is triturated with TBME.

C$_{10}$H$_6$ClIN$_2$ (M=316.5 g/mol)
ESI-MS: 317 [M+H]+
R$_t$ (HPLC): 3.15 (method B)

Example XVI

4-Iodo-2-propoxy-pyridine

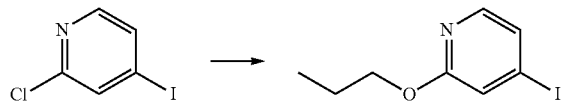

0.58 g (25.06 mmol) sodium are carefully added to 40 mL n-propanol by several portions. The mixture is stirred until the metal is dissolved completely (ca. 45 min). Then 6.00 g (25.1 mmol) 2-chloro-4-iodo-pyridine are slowly added to the mixture. The mixture is stirred at reflux for 3 h. The reaction is quenched by the addition of some water. The solvent is removed in vacuo and to the residue are added 20 mL DMF/MeOH. The mixture is filtrated and the filtrate is purified by HPLC (MeOH/H$_2$O/NH$_3$).

C$_8$H$_{10}$INO (M=263.1 g/mol)
ESI-MS: 264 [M+H]+
R$_t$ (HPLC): 2.22 min (method F)

Example XVII

Example XVII.1 (general route)

(S)-Benzyl 1-(4-(1-(4-(cyclopropylmethoxy)phenyl)azetidin-3-yl)phenyl)ethyl-carbamate

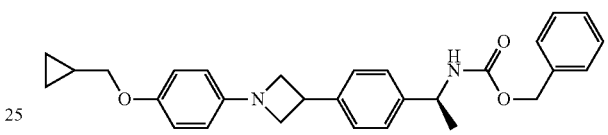

To 3.00 g (9.66 mmol) of amine VII.2 in 50 mL dioxane are added 3.28 g (14.5 mmol) 1-bromo-4-cyclopropoxy-benzene, 1.16 g (29.0 mmol) NaOH, 0.88 g (0.97 mmol) Pd$_2$dba$_3$ and 430 mg (1.45 mmol) 2-(di-tert-butylphosphino)biphenyl. The mixture is degassed thoroughly and stirred at 45° C. over night. DCM is added and the mixture is filtered and the solvent is removed in vacuo. The residue is purified by flash chromatography (silica gel, PE/EtOAc 4/1).

C$_{29}$H$_{32}$N$_2$O$_3$ (M=456.6 g/mol)
R$_f$(TLC): 0.8 (silica gel DCM/MeOH 10/1))

The following compounds are prepared analogously to example XVII.1

| Ex. | Starting material | Structure | TLC R$_f$-value (silica gel) |
|---|---|---|---|
| XVII.1 | VII.2 | 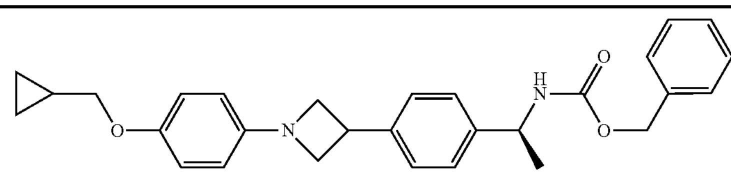 | 0.8 (DCM/MeOH 10/1) |
| XVII.2 | VII.2 | 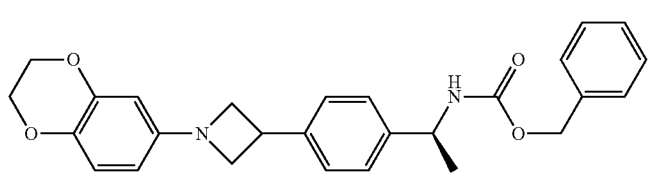 [SMILES: C[C@H](NC(=O)OCc1ccccc1)c1ccc(C2CN(c3ccc4c(c3)OCCO4)C2)cc1] | 0.9 (DCM/MeOH 10/1) |
| XVII.3 | VII.3 | 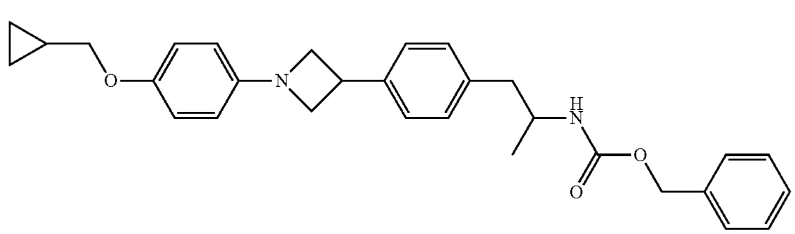 [SMILES: CC(Cc1ccc(C2CN(c3ccc(OCC4CC4)cc3)C2)cc1)NC(=O)OCc1ccccc1] | 0.5 (DCM/MeOH 3/1) |

| Ex. | Starting material | Structure | TLC $R_f$-value (silica gel) |
|---|---|---|---|
| XVII.4 | VII.3 | 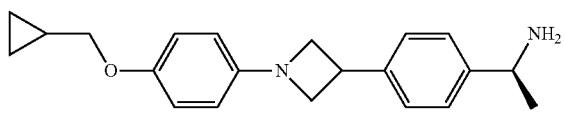 [SMILES: C[C@H](N)c1ccc(C2CN(c3ccc(OCC4CC4)cc3)C2)cc1] | 0.4 (DCM/MeOH 3/1) |

Example XVIII

Example XVIII.1 (General Route)

(S) 1-(4-(1-(4-(cyclopropylmethoxy)phenyl)azetidin-3-yl)phenyl)ethanamine 3.00 g (6.57 mmol) of example XVII.1 and 0.6 g Pd(OH)$_2$/C in 150 mL ethanol are degassed and put under H$_2$ (30 psi) at room temperature over night. After filtration the solution is concentrated and the residue is purified by flash chromatography (silica gel, PE/DCM 0/100).

$C_{21}H_{26}N_2O$ (M=322.4 g/mol)

ESI-MS: 323 [M+H]$^+$ $R_f$(TLC): 0.1 (silica gel PE/EtOAc 1/1)

The following compounds are prepared analogously to example XVIII.1

| Ex. | Starting material | Structure | Mass spec result | TLC $R_f$-value (silica gel) |
|---|---|---|---|---|
| XVIII.1 | XVII.1 | 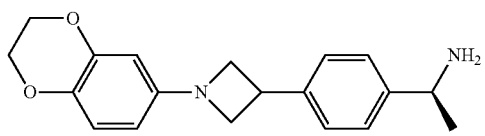 | 323 [M + H]$^+$ | 0.1 (PE/EtOAc 1/1) |
| XVIII.2 | XVII.2 | 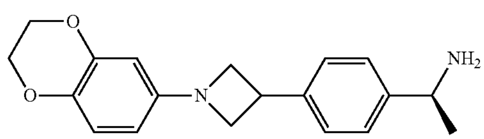 | 311 [M + H]$^+$ | 0.1 (PE/EtOAc 2/1) |
| XVIII.3 | XVII.3 | 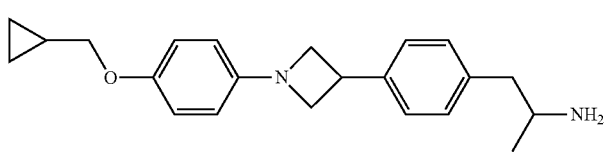 [SMILES: CC(N)Cc1ccc(C2CN(c3ccc(OCC4CC4)cc3)C2)cc1] | 337 [M + H]$^+$ | 0.0 (PE/EtOAc 3/1) |
| XVIII.4 | XVII.3 | 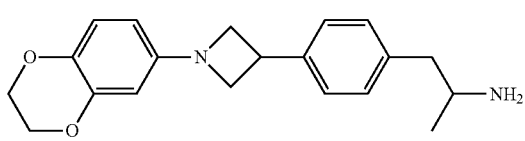 [SMILES: CC(N)Cc1ccc(C2CN(c3ccc4c(c3)OCCO4)C2)cc1] | 325 [M + H]$^+$ | 0.0 (PE/EtOAc 3/1) |

Example XIX

2-Acetamidooxazole-4-carboxylic acid

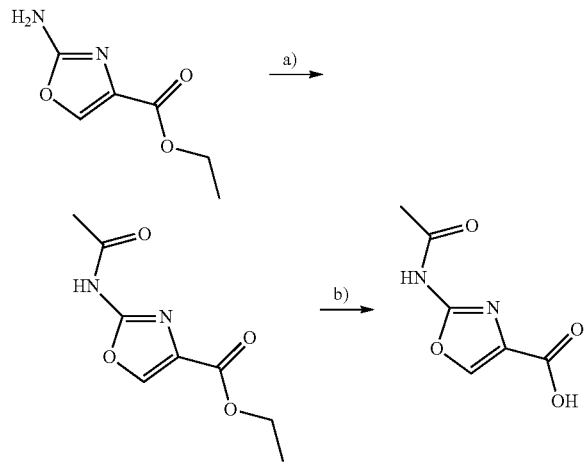

a) 1.0 g (6.41 mmol) ethyl 2-aminooxazole-4-carboxylate and 9.10 mL (96.3 mmol) Ac$_2$O are stirred at r.t. over the weekend. Then the solvent is removed in vacuo. Some toluene is added and all volatile components are removed in vacuo again. This procedure is repeated three times. The crude product is used without further purification.

b) 1.31 g (6.60 mmol) of ethyl 2-acetamidooxazole-4-carboxylate are added to 33 mL EtOH. 0.55 g (13.2 mmol) LiOH are added and the resulting mixture is stirred at r.t. over night. Then the EtOH is removed in vacuo and diluted aq. HCl is added and the resulting precipitate is collected, washed with cold water and dried. The resulting product is used without further purification.

C$_6$H$_6$N$_2$O$_4$ (M=170.1 g/mol)
ESI-MS: 171 [M+H]$^+$
R$_t$ (HPLC): 0.51 (method V)

Example XX

Example XX.1 (General Route)

2-Bromo-5-(2,2-difluoro-cyclopropylmethoxy)-pyridine

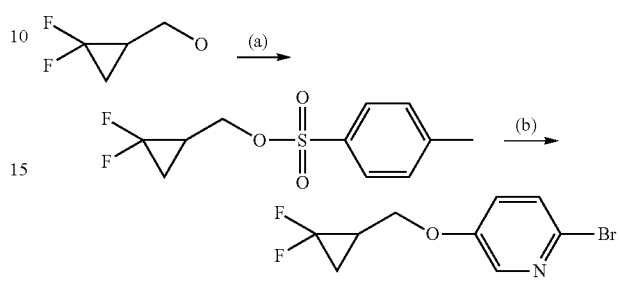

a) To 5.50 g (50.9 mmol) (2,2-difluorocyclopropyl)methanol and 14.4 mL (102 mmol) TEA in 70 mL THF are added 10.2 g (53.4 mmol) p-toluenesulfonyl chloride and the resulting mixture is stirred at r.t. over night. Afterwards the reaction ist quenched by the addition of water and extracted with EtOAC (2×50 mL). The combined org. layers are washed with aq. half sat. NaHCO$_3$ solution, dried over MgSO$_4$, filtered and the solvent is removed in vacuo.

C$_{11}$H$_{12}$F$_2$O$_3$S (M=262.3 g/mol)
ESI-MS: 285 [M+Na]$^+$
R$_t$ (HPLC): 1.03 min (method W)

b) 5.0 g (28.7 mmol) 2-bromo-5-hydroxypyridine, 7.54 g (28.7 mmol) of the above mentioned product and 11.9 g (86.2 mmol) K$_2$CO$_3$ are added to 100 mL ACN and stirred at 80° C. over night. Afterwards the reaction mixture is diluted with water, filtered and directly purified by HPLC (ACN/H$_2$O/NH$_3$).

C$_9$H$_8$BrF$_2$NO (M=264.1 g/mol)
ESI-MS: 264/266 [M]$^+$
R$_t$ (HPLC): 0.85 min (method X)

The following compounds are prepared analogously to example XX.1

| Ex. | Starting material | Product structure | Mass spec result | HPLC retention time (method) |
|---|---|---|---|---|
| XX.1 | HO-pyridine-Br | F$_2$-cyclopropyl-CH$_2$-O-pyridine-Br | 264/266 [M + H]$^+$ | 0.85 (X) |
| XX.2 | HO-pyridine(F)-Cl | F$_2$-cyclopropyl-CH$_2$-O-pyridine(F)-Cl | 237 [M + H]$^+$ | 1.09 (W) |
| XX.3 | HO-pyrimidine-Cl | F$_2$-cyclopropyl-CH$_2$-O-pyrimidine-Cl | 221 [M + H]$^+$ | 1.95 (W) |

Example XXI

Example XXI.1 (General Route)

(S)—N-(1-(4-(1-(2-chloropyrimidin-4-yl)azetidin-3-yl)phenyl)ethyl)acetamide

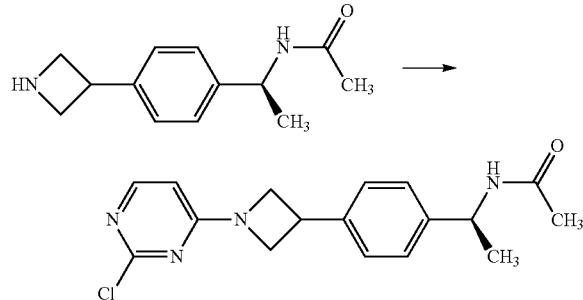

290 mg (1.14 mmol) of intermediate VI.3, 170 mg (1.14 mmol) 2,4-dichloropyrimidine and 0.32 mL (2.23 mmol) TEA are added to 5 mL THF and stirred at 80° C. over night. The reaction mixture is quenched by the addition of water and extracted with EtOAc (3×). The combined org. layers are dried over MgSO$_4$, filtered and the solvent is removed in vacuo.

$C_{17}H_{19}ClN_4O$ (M=330.8 g/mol)

ESI-MS: 331 [M+H]$^+$

R$_t$ (HPLC): 0.83 min (method W)

The following compounds are prepared analogously to example XXI.1

For example XXI.4 ACN is used as solvent and the reaction conditions are r.t. for 3 h.

For the examples XXI.5 and XXI.6 ACN is used as solvent and K$_2$CO$_3$ as base.

| Ex. | Starting material | Product structure | Mass spec result | HPLC retention time (method) |
|---|---|---|---|---|
| XXI.1 | VI.3 + 2,4-dichloro pyrimidine | | 331 [M + H]$^+$ | 0.83 (W) |
| XXI.2 | VI.3 + 2,4-dichloro-5-fluoro pyrimidine | | 349 [M + H]$^+$ | 0.77 (X) |
| XXI.3 | VI.3 + 2,4-difluoro pyrimidine | | 314 [M + H]$^+$ | 0.79 (W) |
| XXI.4 | VI.3 + 4,6-dichloro-5-fluoro pyrimidine | | 349 [M + H]$^+$ | 0.94 (W) |
| XXI.5 | VI.3 + 2,4-dichloro-3-fluoro pyridine | | 348 [M + H]$^+$ | 0.90 (W) |

-continued

| Ex. | Starting material | Product structure | Mass spec result | HPLC retention time (method) |
|---|---|---|---|---|
| XXI.6 | VI.3 + 4,5,6-trichloro-pyrimidine | (structure: 4,5-dichloropyrimidin-6-yl azetidine linked to phenyl-CH(CH₃)-NHCOCH₃) | 365 [M + H]⁺ | 0.98 (W) |

Preparation of Final Compounds

Example 1

Example 1.1 (General Route)

N-(1-(4-(1-(4-Propoxyphenyl)azetidin-3-yl)phenyl)propan-2-yl)acetamide

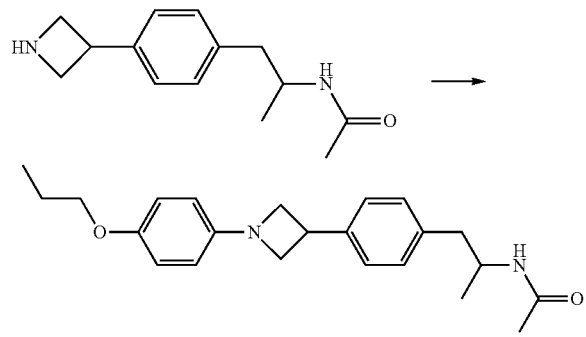

To 80 mg (0.34 mmol) of amine in 1.5 mL dioxane are added 77.8 mg (0.36 mmol) 1-bromo-4-propoxy-benzene, 132 mg (1.38 mmol) NaOtBu, 31.5 mg (34.4 μmol) $Pd_2$ $dba_3$ and 30.8 mg (0.10 mmol) 2-(di-tert-butylphosphino)biphenyl. The mixture is degassed thoroughly and stirred at 45° C. over night. A small amount of water and MeOH is added and the mixture is filtered and afterwards purified by HPLC (MeOH/H₂O/FA).

$C_{23}H_{30}N_2O_2$ (M=366.5 g/mol)

ESI-MS: 367 [M+H]⁺

$R_t$ (HPLC): 2.17 min (method A)

The following compounds are prepared analogously to example 1.1

For example 1.12 the reaction mixture is stirred at 80° C.

For examples 1.31-1.35 chloro(2-dicyclohexylphosphino-2'-4'-6'-tri-isopropyl-1,1'-biphenyl)[2-(2-aminoethyl)phenyl]palladium(II) is used as catalyst.

| Ex. | Starting material(s) | Structure | Mass spec result | HPLC retention time (method) |
|---|---|---|---|---|
| 1.1 | VI.1 | (propoxyphenyl-azetidinyl-phenyl-CH(CH₃)CH₂NHCOCH₃) | 367 [M + H]⁺ | 2.17 (A) |
| 1.2 | VI.1 + VIII.2 | (cyclobutoxyphenyl-azetidinyl-phenyl-CH(CH₃)CH₂NHCOCH₃) | 379 [M + H]⁺ | 2.19 (A) |
| 1.3 | VI.1 + IX | (cyclopropyl-O-phenyl-azetidinyl-phenyl-CH(CH₃)CH₂NHCOCH₃) | 365 [M + H]⁺ | 2.10 (A) |
| 1.4 | VI.1 + VIII.1 | (cyclopropylmethoxy-phenyl-azetidinyl-phenyl-CH(CH₃)CH₂NHCOCH₃) | 379 [M + H]⁺ | 2.14 (A) |

-continued

| Ex. | Starting material(s) | Structure | Mass spec result | HPLC retention time (method) |
|---|---|---|---|---|
| 1.5 | VI.1 | 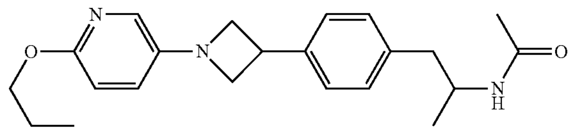 [SMILES: CCCOc1ccc(N2CC(c3ccc(CC(C)NC(C)=O)cc3)C2)cn1] | 368 [M + H]+ | 2.08 (A) |
| 1.6 | VI.1 + X | 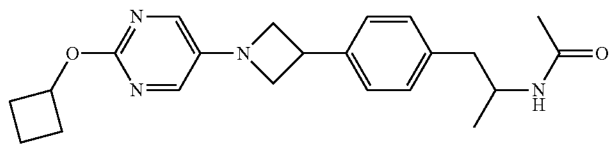 [SMILES: CC(=O)NC(C)Cc1ccc(C2CN(c3cnc(OC4CCC4)nc3)C2)cc1] | 381 [M + H]+ | 2.00 (A) |
| 1.7 | VI.1 + XI | 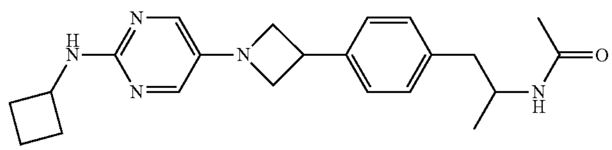 [SMILES: CC(=O)NC(C)Cc1ccc(C2CN(c3cnc(NC4CCC4)nc3)C2)cc1] | 380 [M + H]+ | 1.91 (A) |
| 1.8 | VI.1 | 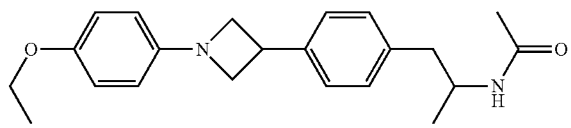 [SMILES: CCOc1ccc(N2CC(c3ccc(CC(C)NC(C)=O)cc3)C2)cc1] | 353 [M + H]+ | 2.05 (A) |
| 1.9 | VI.1 | 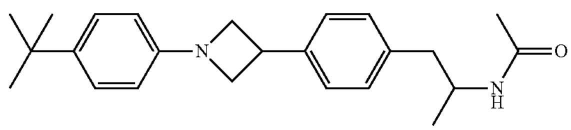 [SMILES: CC(=O)NC(C)Cc1ccc(C2CN(c3ccc(C(C)(C)C)cc3)C2)cc1] | 365 [M + H]+ | 2.33 (A) |
| 1.10 | VI.1 | 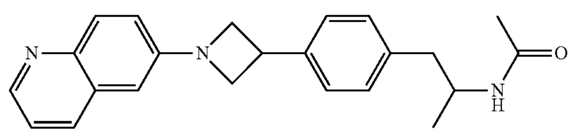 [SMILES: CC(=O)NC(C)Cc1ccc(C2CN(c3ccc4ncccc4c3)C2)cc1] | 360 [M + H]+ | 1.57 (O) |
| 1.11 | VI.1 + VIII.4 | 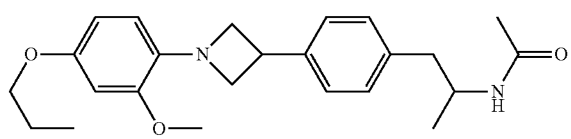 [SMILES: CCCOc1ccc(N2CC(c3ccc(CC(C)NC(C)=O)cc3)C2)c(OC)c1] | 397 [M + H]+ | 1.21 (D) |
| 1.12 | VI.1 + XVI | 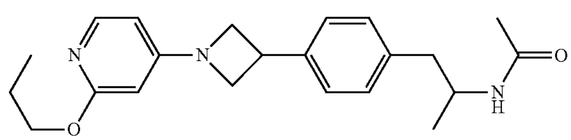 [SMILES: CCCOc1cc(N2CC(c3ccc(CC(C)NC(C)=O)cc3)C2)ccn1] | 368 [M + H]+ | 2.05 (A) |
| 1.13 | VI.1 | 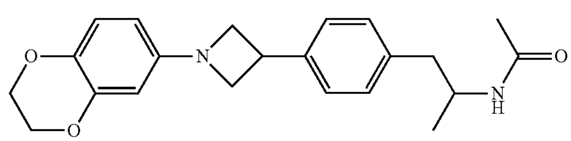 [SMILES: CC(=O)NC(C)Cc1ccc(C2CN(c3ccc4c(c3)OCCO4)C2)cc1] | 367 [M + H]+ | 1.94 (A) |
| 1.14 | VI.2 | 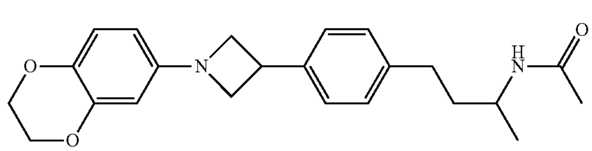 [SMILES: CC(=O)NC(C)CCc1ccc(C2CN(c3ccc4c(c3)OCCO4)C2)cc1] | 381 [M + H]+ | 2.30 (A) |
| 1.15 | VI.2 + IX | 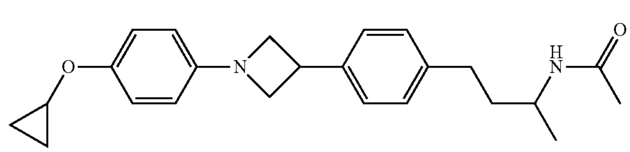 [SMILES: CC(=O)NC(C)CCc1ccc(C2CN(c3ccc(OC4CC4)cc3)C2)cc1] | 379 [M + H]+ | 2.43 (A) |

-continued
| Ex. | Starting material(s) | Structure | Mass spec result | HPLC retention time (method) |
|---|---|---|---|---|
| 1.16 | VI.2 | 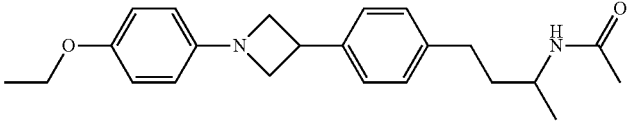 | 367 [M + H]⁺ | 2.40 (A) |
| 1.17* | VI.2 + VIII.1 | 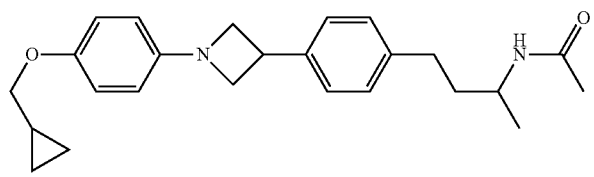 [SMILES: CC(=O)NC(C)CCc1ccc(C2CN(c3ccc(OCC4CC4)cc3)C2)cc1] | 393 [M + H]⁺ | 2.47 (A) |
| 1.18 | VI.2 | 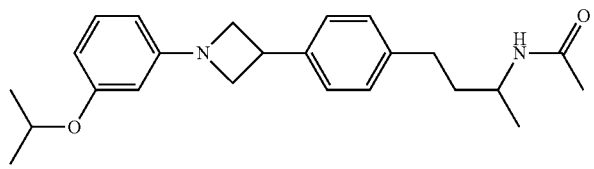 | 381 [M + H]⁺ | 2.25 (A) |
| 1.19 | VII.1 | 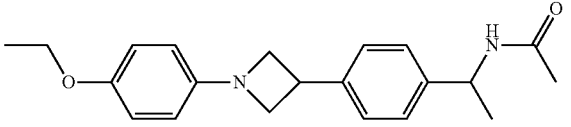 [SMILES: CCOc1ccc(N2CC(c3ccc(C(C)NC(C)=O)cc3)C2)cc1] | 339 [M + H]⁺ | 2.00 (A) |
| 1.20 | VII.1 | 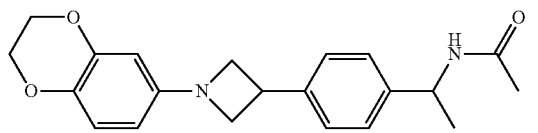 [SMILES: CC(=O)NC(C)c1ccc(C2CN(c3ccc4c(c3)OCCO4)C2)cc1] | 353 [M + H]⁺ | 1.86 (A) |
| 1.21 | VII.1 + VIII.3 | 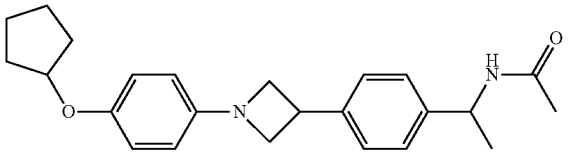 [SMILES: CC(=O)NC(C)c1ccc(C2CN(c3ccc(OC4CCCC4)cc3)C2)cc1] | 379 [M + H]⁺ | 2.20 (A) |
| 1.22 | VII.1 + XII | 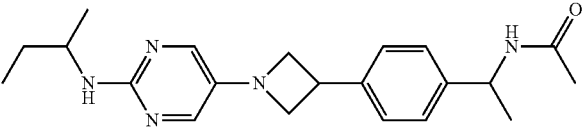 [SMILES: CCC(C)Nc1ncc(N2CC(c3ccc(C(C)NC(C)=O)cc3)C2)cn1] | 368 [M + H]⁺ | 1.89 (A) |
| 1.23 | VI.3 + VIII.1 | 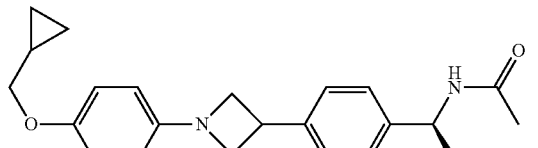 | 365 [M + H]⁺ | 1.99 (A) |
| 1.24 | VI.3 + VIII.2 | 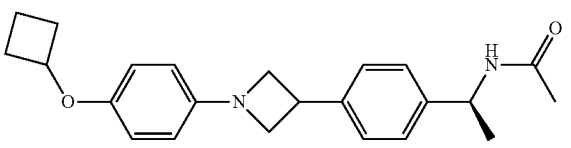 [SMILES: CC(=O)N[C@@H](C)c1ccc(C2CN(c3ccc(OC4CCC4)cc3)C2)cc1] | 365 [M + H]⁺ | 2.04 (A) |

-continued

| Ex. | Starting material(s) | Structure | Mass spec result | HPLC retention time (method) |
|---|---|---|---|---|
| 1.25 | VI.3 + IX | 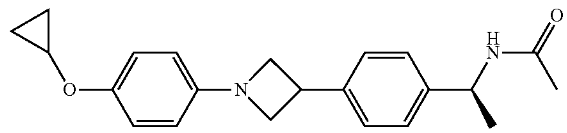 [SMILES: CC(=O)N[C@@H](C)c1ccc(C2CN(c3ccc(OC4CC4)cc3)C2)cc1] | 351 [M + H]+ | 1.93 (A) |
| 1.26 | VI.3 | 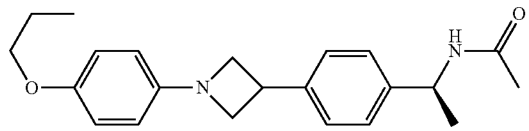 [SMILES: CCCOc1ccc(N2CC(c3ccc([C@H](C)NC(C)=O)cc3)C2)cc1] | 353 [M + H]+ | 2.03 (A) |
| 1.27 | VI.3 | 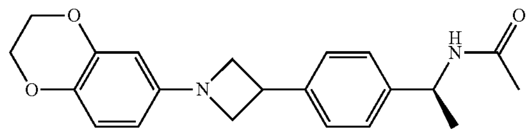 [SMILES: CC(=O)N[C@@H](C)c1ccc(C2CN(c3ccc4c(c3)OCCO4)C2)cc1] | 353 [M + H]+ | 1.76 (A) |
| 1.28 | VI.3 | 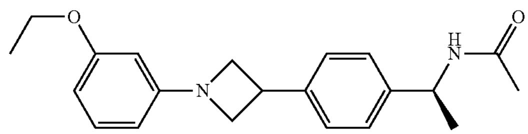 [SMILES: CCOc1cccc(N2CC(c3ccc([C@H](C)NC(C)=O)cc3)C2)c1] | 339 [M + H]+ | 1.94 (A) |
| 1.29 | VI.3 | 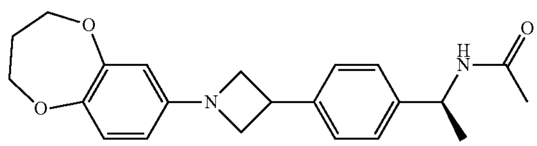 [SMILES: CC(=O)N[C@@H](C)c1ccc(C2CN(c3ccc4c(c3)OCCCO4)C2)cc1] | 367 [M + H]+ | 1.04 (K) |
| 1.30 | VI.1 + XX.2 | 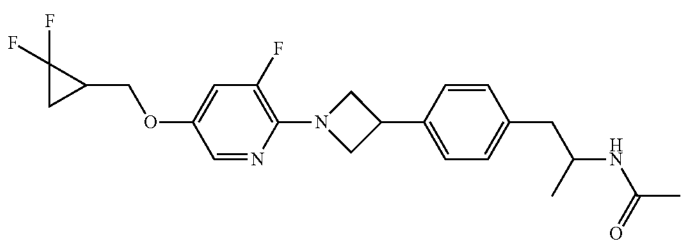 [SMILES: CC(=O)NC(C)Cc1ccc(C2CN(c3ncc(OCC4CC4(F)F)cc3F)C2)cc1] | 434 [M + H]+ | 1.06 (W) |
| 1.31 | VI.3 + XX.1 | 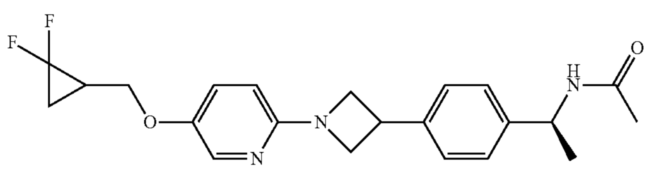 [SMILES: CC(=O)N[C@@H](C)c1ccc(C2CN(c3ccc(OCC4CC4(F)F)cn3)C2)cc1] | 402 [M + H]+ | 0.84 (W) |
| 1.32 | VI.3 | 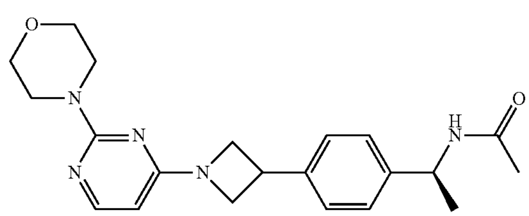 [SMILES: CC(=O)N[C@@H](C)c1ccc(C2CN(c3ccnc(N4CCOCC4)n3)C2)cc1] | 382 [M + H]+ | 0.78 (W) |
| 1.33 | VI.3 + XX.3 | 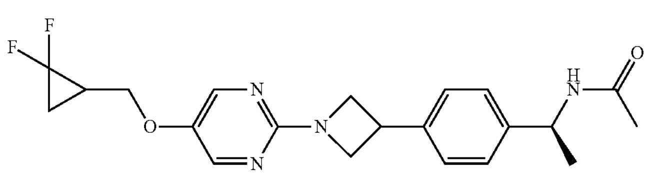 [SMILES: CC(=O)N[C@@H](C)c1ccc(C2CN(c3ncc(OCC4CC4(F)F)cn3)C2)cc1] | 403 [M + H]+ | 1.00 (W) |

-continued

| Ex. | Starting material(s) | Structure | Mass spec result | HPLC retention time (method) |
|---|---|---|---|---|
| 1.34 | VI.3 + VIII.5 | 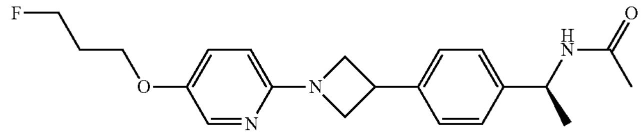 [SMILES: CC(=O)N[C@@H](C)c1ccc(C2CN(c3ccc(OCCCF)cn3)C2)cc1] | 372 [M + H]⁺ | 0.80 (W) |
| 1.35 | VI.3 + XX.2 | 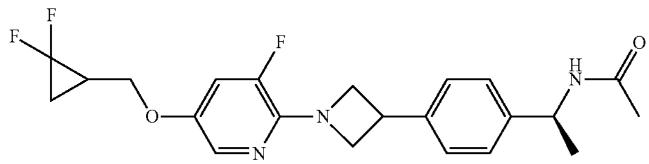 [SMILES: CC(=O)N[C@@H](C)c1ccc(C2CN(c3ncc(OCC4CC4(F)F)cc3F)C2)cc1] | 420 [M + H]⁺ | 0.95 (W) |

*For example 1.17 a separation of the enantiomers was performed using chiral SFC: column: Daicel ADH (250 mm × 4.6 mm); flow: 4 ml/min; solvent: CO₂/iPrOH with diethylamine (60%/40%); time: 10 min.

Example 2

Example 2.1 (General Route)

N-(1-(4-(1-(5-bromopyrimidin-2-yl)azetidin-3-yl)phenyl)propan-2-yl)acetamide

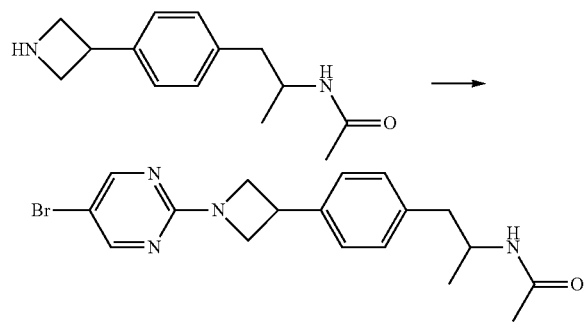

To 70 mg (0.30 mmol) of amine VI.1 in 1 ml DMSO are added 75.8 mg (0.39 mmol) 5-bromo-2-chloropyrimidine and 78.7 µl (0.45 mmol) DIPEA. The mixture is stirred at 35° C. over night and afterwards purified by HPLC (MeOH/H₂O/NH₃).

$C_{18}H_{21}BrN_4O$ (M=389.3 g/mol)

ESI-MS: 389/391 [M+H]⁺

$R_t$ (HPLC): 1.79 min (method A)

The following compounds are prepared analogously to example 2.1.

For the example 2.3 the reaction mixture is stirred at 90° C.

For example 2.14 NMP is used as solvent and the reaction conditions are 150° C. for 2 h.

| Ex. | Starting material(s) | Structure | Mass spec result | HPLC retention time (method) |
|---|---|---|---|---|
| 2.1 | VI.1 | 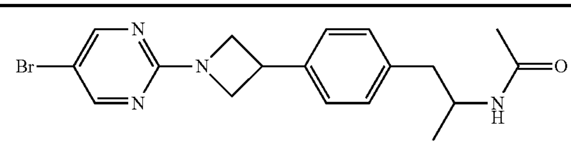 | 389/391 [M + H]⁺ | 1.79 (A) |
| 2.2 | VI.1 | 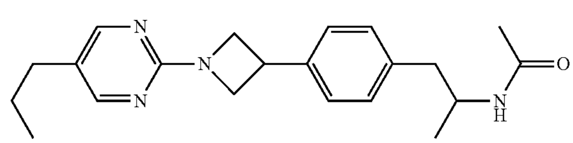 [SMILES: CCCc1cnc(N2CC(c3ccc(CC(C)NC(C)=O)cc3)C2)nc1] | 353 [M + H]⁺ | 1.95 (A) |
| 2.3 | VI.1 + XV | 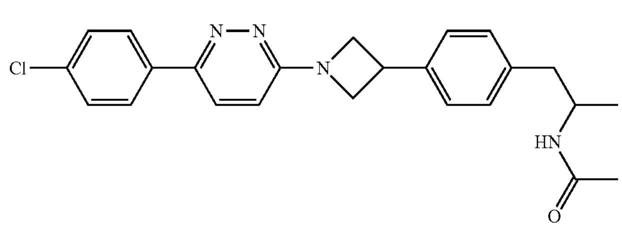 [SMILES: CC(=O)NC(C)Cc1ccc(C2CN(c3ccc(-c4ccc(Cl)cc4)nn3)C2)cc1] | 421 [M + H]⁺ | 2.02 (A) |

-continued

| Ex. | Starting material(s) | Structure | Mass spec result | HPLC retention time (method) |
|---|---|---|---|---|
| 2.4 | VI.2 + XIII | 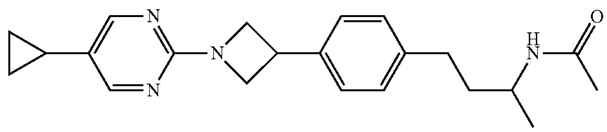 [SMILES: CC(=O)NC(C)CCc1ccc(C2CN(c3ncc(C4CC4)cn3)C2)cc1] | 365 [M + H]⁺ | 1.99 (A) |
| 2.5 | VI.2 + XIV.1 | 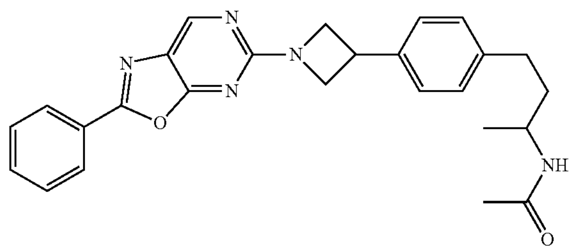 [SMILES: CC(=O)NC(C)CCc1ccc(C2CN(c3ncc4nc(-c5ccccc5)oc4n3)C2)cc1] | 442 [M + H]⁺ | 2.23 (A) |
| 2.6 | VI.2 | 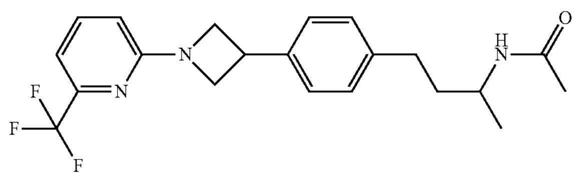 [SMILES: CC(=O)NC(C)CCc1ccc(C2CN(c3cccc(C(F)(F)F)n3)C2)cc1] | 392 [M + H]⁺ | 2.13 (A) |
| 2.7 | VI.3 + XIV.1 | 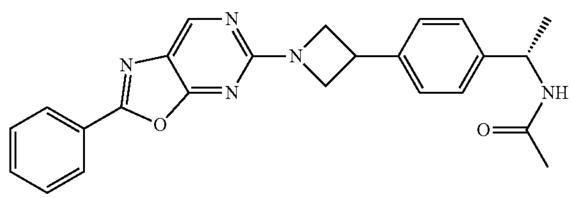 [SMILES: CC(=O)N[C@@H](C)c1ccc(C2CN(c3ncc4nc(-c5ccccc5)oc4n3)C2)cc1] | 414 [M + H]⁺ | 2.10 (A) |
| 2.8 | VI.3 | 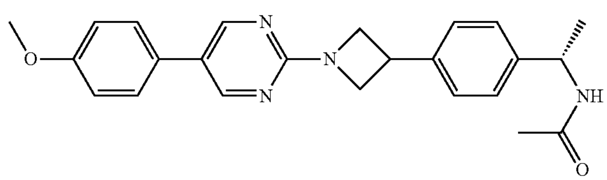 [SMILES: COc1ccc(-c2cnc(N3CC(c4ccc([C@H](C)NC(C)=O)cc4)C3)nc2)cc1] | 403 [M + H]⁺ | 2.11 (A) |
| 2.9 | VI.3 | 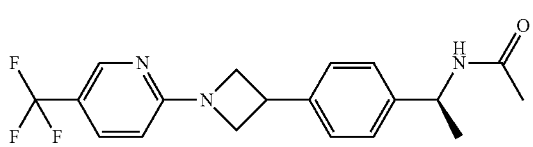 [SMILES: CC(=O)N[C@@H](C)c1ccc(C2CN(c3ccc(C(F)(F)F)cn3)C2)cc1] | 364 [M + H]⁺ | 2.11 (A) |
| 2.10 | VI.3 | 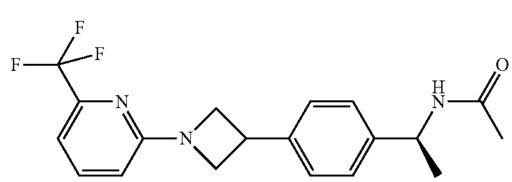 [SMILES: CC(=O)N[C@@H](C)c1ccc(C2CN(c3cccc(C(F)(F)F)n3)C2)cc1] | 364 [M + H]⁺ | 2.11 (A) |
| 2.11 | VI.3 | 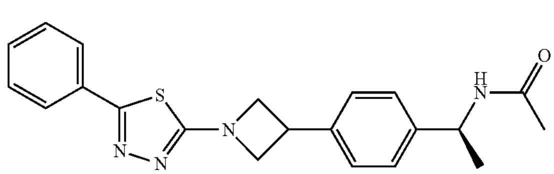 [SMILES: CC(=O)N[C@@H](C)c1ccc(C2CN(c3nnc(-c4ccccc4)s3)C2)cc1] | 379 [M + H]⁺ | 1.06 (K) |

-continued

| Ex. | Starting material(s) | Structure | Mass spec result | HPLC retention time (method) |
|---|---|---|---|---|
| 2.12 | VI.3 + XIII | 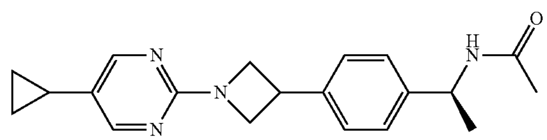 [SMILES: CC(=O)N[C@@H](C)c1ccc(C2CN(c3ncc(C4CC4)cn3)C2)cc1] | 337 [M + H]⁺ | 2.10 (A) |
| 2.13 | VI.3 + XIV.2 | 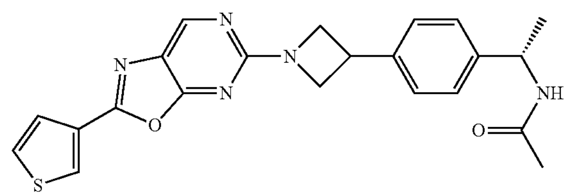 [SMILES: CC(=O)N[C@@H](C)c1ccc(C2CN(c3ncc4nc(-c5ccsc5)oc4n3)C2)cc1] | 420 [M + H]⁺ | 1.11 (K) |
| 2.14 | VI.1 + XX.3 | 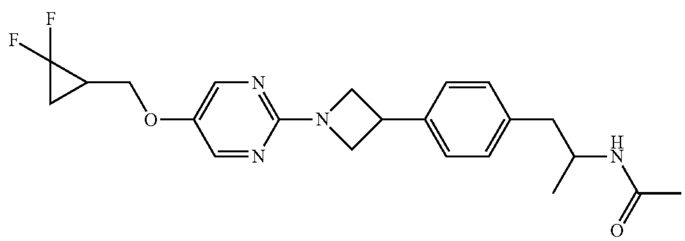 [SMILES: CC(=O)NC(C)Cc1ccc(C2CN(c3ncc(OCC4CC4(F)F)cn3)C2)cc1] | 416 [M + H]⁺ | 0.94 (W) |
| 2.15 | VI.3 | 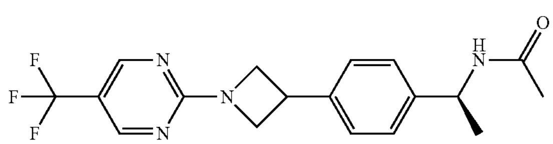 [SMILES: CC(=O)N[C@@H](C)c1ccc(C2CN(c3ncc(C(F)(F)F)cn3)C2)cc1] | 365 [M + H]⁺ | 0.97 (W) |

Example 3

Example 3.1 (General Route)

(S)—N-(1-(4-(1-(4-(cyclopropylmethoxy)phenyl)azetidin-3-yl)phenyl)ethyl)-5-methylisoxazole-4-carboxamide

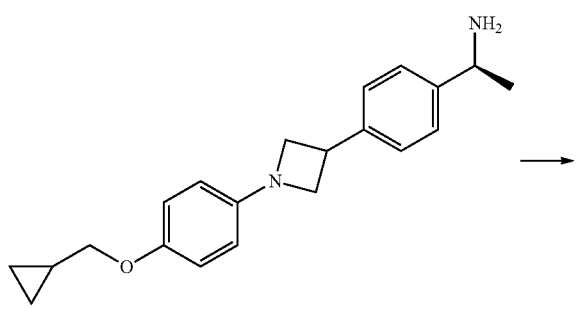

→

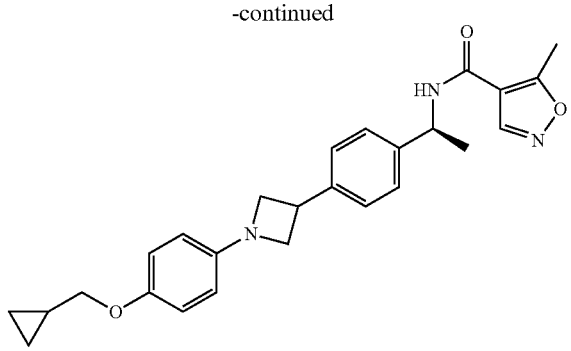

To 48.4 mg (0.15 mmol) of amine XVIII.1 in 2 ml DMF are added 48.2 mg (0.15 mmol) TBTU and 80 µL (0.45 mmol) DIPEA. The mixture is stirred at r.t. for 5 min and then treated with 19.1 mg (0.15 mmol) 5-methylisoazole-4-carboxylic acid. The resulting mixture is stirred at r.t. over night and purified by HPLC (MeOH/H₂O/NH₃).

$C_{26}H_{29}N_3C_3$ (M=431.5 g/mol)

ESI-MS: 432 [M+H]⁺

$R_t$ (HPLC): 1.36 min (method T)

The following compounds are prepared analogously to example 3.1.

For example 3.4 the reaction mixture is stirred at 60° C. over night.

| Ex. | Starting material(s) | Structure | Mass spec result | HPLC retention time (method) |
|---|---|---|---|---|
| 3.1 | XVIII.1 | 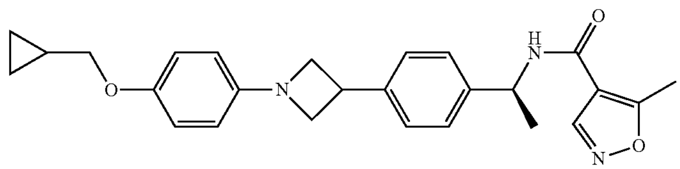 [SMILES: Cc1oncc1C(=O)N[C@@H](C)c1ccc(C2CN(c3ccc(OCC4CC4)cc3)C2)cc1] | 432 [M + H]$^+$ | 1.36 (T) |
| 3.2 | XVIII.1 | 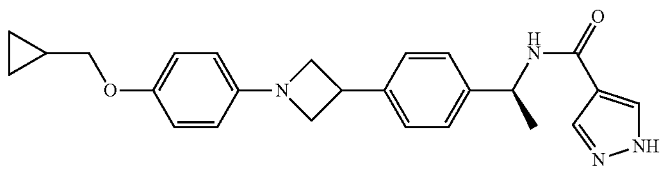 [SMILES: C[C@H](NC(=O)c1cn[nH]c1)c1ccc(C2CN(c3ccc(OCC4CC4)cc3)C2)cc1] | 417 [M + H]$^+$ | 1.25 (T) |
| 3.3 | XVIII.1 | 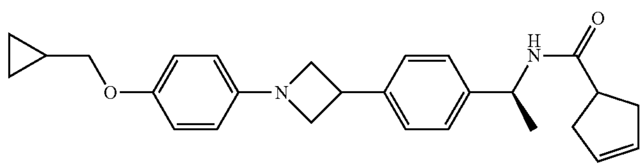 [SMILES: C[C@H](NC(=O)C1CC=CC1)c1ccc(C2CN(c3ccc(OCC4CC4)cc3)C2)cc1] | 417 [M + H]$^+$ | 1.25 (T) |
| 3.4 | XVIII.1 | 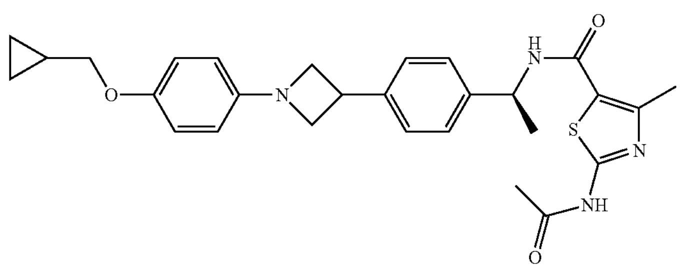 [SMILES: CC(=O)Nc1nc(C)c(C(=O)N[C@@H](C)c2ccc(C3CN(c4ccc(OCC5CC5)cc4)C3)cc2)s1] | 505 [M + H]$^+$ | 1.37 (T) |
| 3.5 | XVIII.3 | 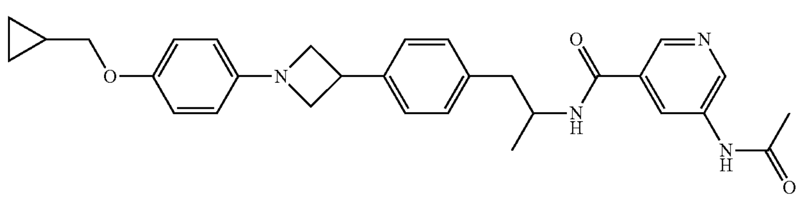 [SMILES: CC(=O)Nc1cncc(C(=O)NC(C)Cc2ccc(C3CN(c4ccc(OCC5CC5)cc4)C3)cc2)c1] | 499 [M + H]$^+$ | 0.66 (U) |
| 3.6 | XVIII.3 | 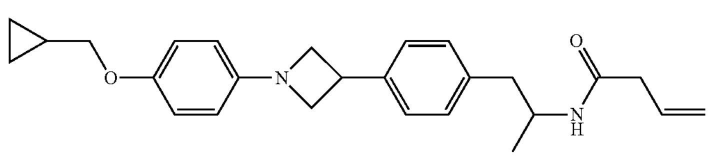 [SMILES: C=CCC(=O)NC(C)Cc1ccc(C2CN(c3ccc(OCC4CC4)cc3)C2)cc1] | 405 [M + H]$^+$ | 0.65 (U) |
| 3.7 | XVIII.3 | 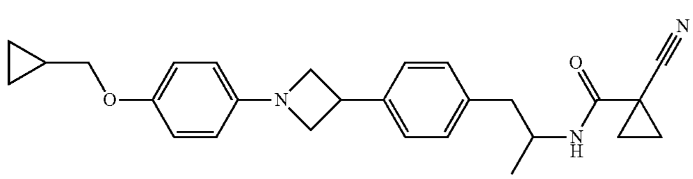 [SMILES: CC(Cc1ccc(C2CN(c3ccc(OCC4CC4)cc3)C2)cc1)NC(=O)C1(C#N)CC1] | 430 [M + H]$^+$ | 0.65 (U) |

-continued
| Ex. | Starting material(s) | Structure | Mass spec result | HPLC retention time (method) |
|---|---|---|---|---|
| 3.8 | XVIII.3 | 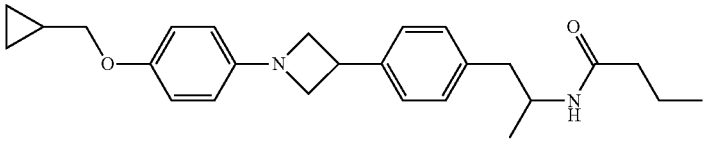 [SMILES: CCCC(=O)NC(C)Cc1ccc(C2CN(c3ccc(OCC4CC4)cc3)C2)cc1] | 407 [M + H]+ | 0.65 (U) |
| 3.9 | XVIII.3 | 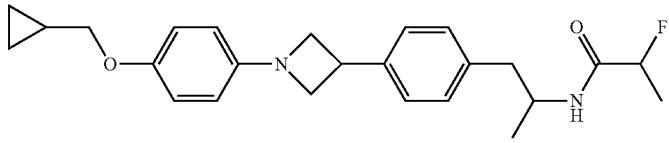 [SMILES: CC(Cc1ccc(C2CN(c3ccc(OCC4CC4)cc3)C2)cc1)NC(=O)C(C)F] | 411 [M + H]+ | 0.66 (U) |
| 3.10 | XVIII.3 | 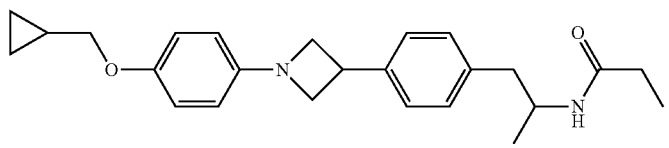 | 393 [M + H]+ | 0.65 (U) |
| 3.11 | XVIII.3 | 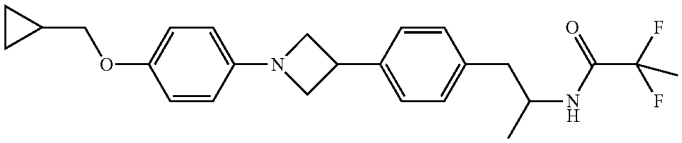 | 429 [M + H]+ | 0.65 (U) |
| 3.12 | XVIII.3 | 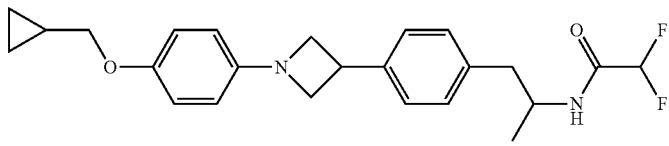 [SMILES: CC(Cc1ccc(C2CN(c3ccc(OCC4CC4)cc3)C2)cc1)NC(=O)C(F)F] | 415 [M + H]+ | 0.65 (U) |
| 3.13 | XVIII.3 | 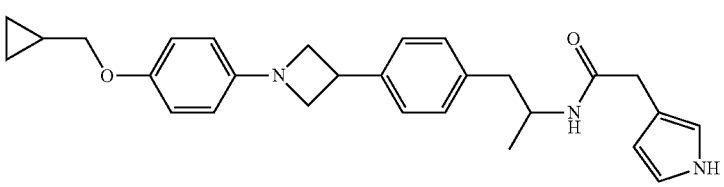 [SMILES: CC(Cc1ccc(C2CN(c3ccc(OCC4CC4)cc3)C2)cc1)NC(=O)Cc1cc[nH]c1] | 444 [M + H]+ | 0.66 (U) |
| 3.14 | XVIII.3 | 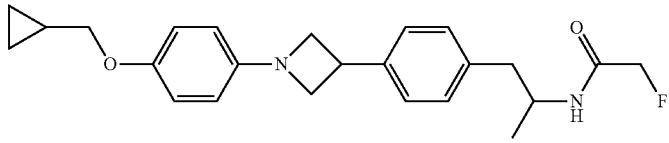 | 397 [M + H]+ | 0.64 (U) |
| 3.15 | XVIII.3 | 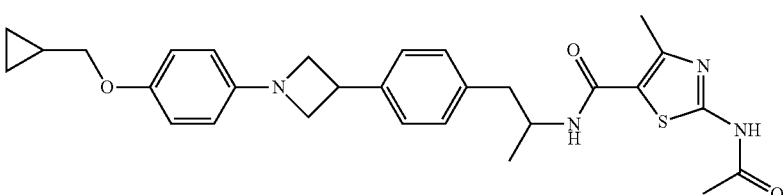 | 519 [M + H]+ | 0.65 (U) |
| 3.16 | XVIII.3 | 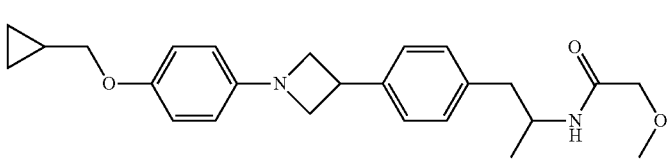 [SMILES: COCC(=O)NC(C)Cc1ccc(C2CN(c3ccc(OCC4CC4)cc3)C2)cc1] | 409 [M + H]+ | 0.64 (U) |

-continued

| Ex. | Starting material(s) | Structure | Mass spec result | HPLC retention time (method) |
|---|---|---|---|---|
| 3.17 | XVIII.3 | 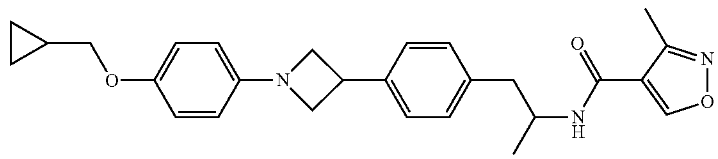 [SMILES: Cc1nocc1C(=O)NC(C)Cc1ccc(C2CN(c3ccc(OCC4CC4)cc3)C2)cc1] | 446 [M + H]+ | 0.65 (U) |
| 3.18 | XVIII.3 | 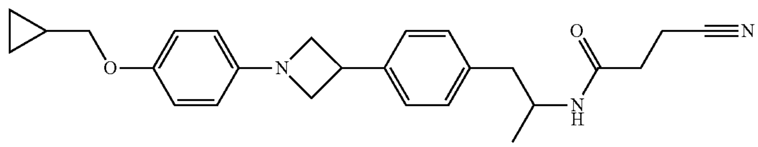 [SMILES: CC(Cc1ccc(C2CN(c3ccc(OCC4CC4)cc3)C2)cc1)NC(=O)CCC#N] | 418 [M + H]+ | 0.64 (U) |
| 3.19 | XVIII.4 | 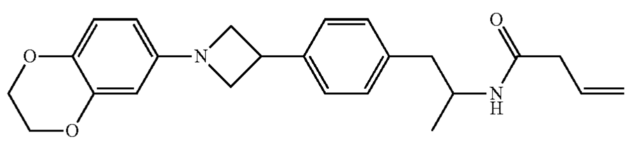 [SMILES: C=CCC(=O)NC(C)Cc1ccc(C2CN(c3ccc4c(c3)OCCO4)C2)cc1] | 393 [M + H]+ | 0.65 (U) |
| 3.20 | XVIII.1 | 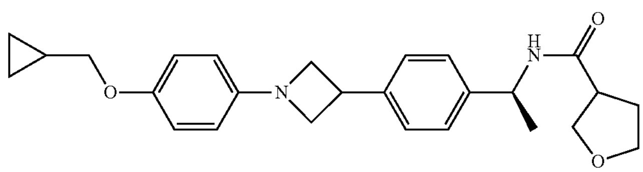 [SMILES: C[C@H](NC(=O)C1CCOC1)c1ccc(C2CN(c3ccc(OCC4CC4)cc3)C2)cc1] | 421 [M + H]+ | 0.61 (U) |
| 3.21 | XVIII.1 | 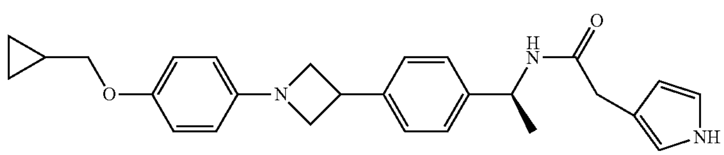 [SMILES: C[C@H](NC(=O)Cc1cc[nH]c1)c1ccc(C2CN(c3ccc(OCC4CC4)cc3)C2)cc1] | 430 [M + H]+ | 0.62 (U) |
| 3.22 | XVIII.1 | 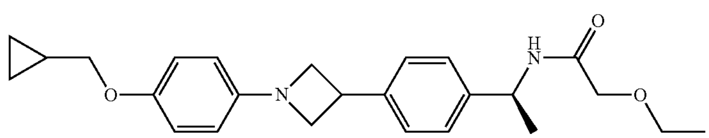 [SMILES: CCOCC(=O)N[C@@H](C)c1ccc(C2CN(c3ccc(OCC4CC4)cc3)C2)cc1] | 409 [M + H]+ | 0.62 (U) |
| 3.23 | XVIII.1 | 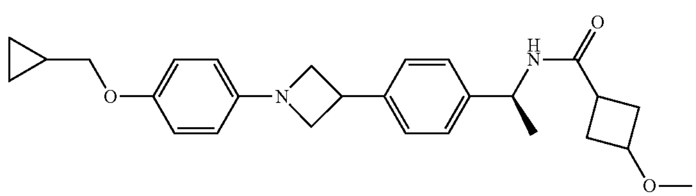 [SMILES: COC1CC(C(=O)N[C@@H](C)c2ccc(C3CN(c4ccc(OCC5CC5)cc4)C3)cc2)C1] | 435 [M + H]+ | 0.62 (U) |
| 3.24 | XVIII.1 | 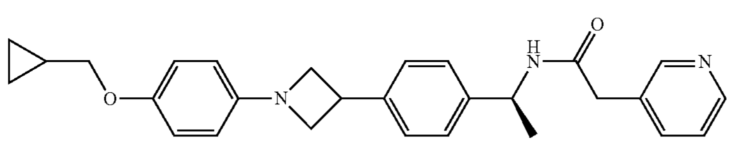 [SMILES: C[C@H](NC(=O)Cc1cccnc1)c1ccc(C2CN(c3ccc(OCC4CC4)cc3)C2)cc1] | 442 [M + H]+ | 0.60 (U) |
| 3.25 | XVIII.1 | 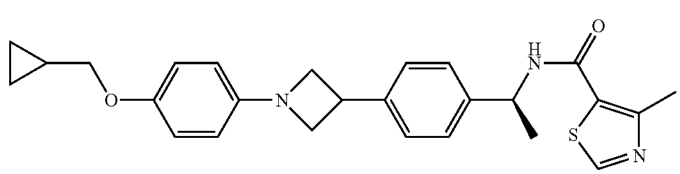 [SMILES: Cc1ncsc1C(=O)N[C@@H](C)c1ccc(C2CN(c3ccc(OCC4CC4)cc3)C2)cc1] | 448 [M + H]+ | 0.62 (U) |

| Ex. | Starting material(s) | Structure | Mass spec result | HPLC retention time (method) |
|---|---|---|---|---|
| 3.26 | XVIII.1 | 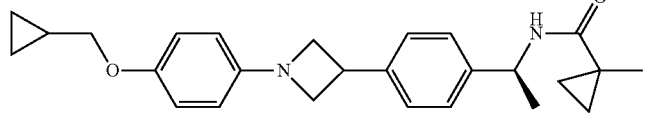 | 405 [M + H]+ | 0.62 (U) |
| 3.27 | XVIII.1 | 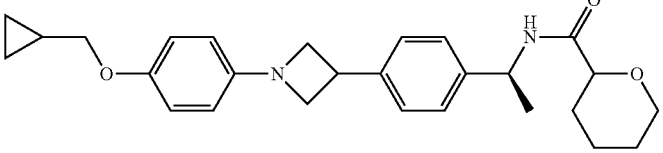 | 435 [M + H]+ | 0.63 (U) |
| 3.28 | XVIII.1 | 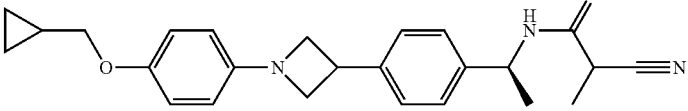 | 404 [M + H]+ | 0.62 (U) |
| 3.29 | XVIII.1 | 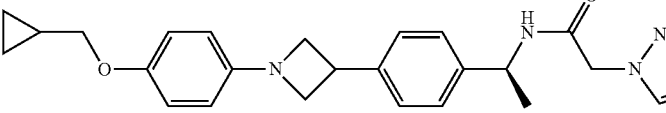 | 432 [M + H]+ | 0.61 (U) |
| 3.30 | XVIII.1 | 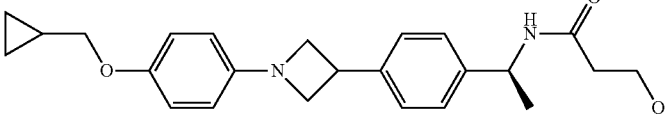 | 409 [M + H]+ | 0.61 (U) |
| 3.31 | XVIII.1 | 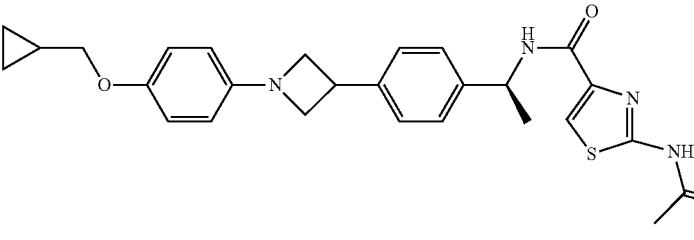 | 491 [M + H]+ | 0.62 (U) |
| 3.32 | XVIII.1 | 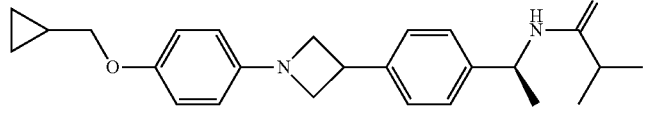 | 393 [M + H]+ | 0.62 (U) |
| 3.33 | XVIII.2 | 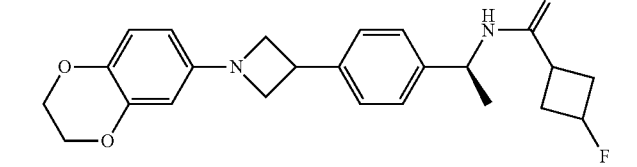 | 411 [M + H]+ | 0.62 (U) |
| 3.34 | XVIII.1 | 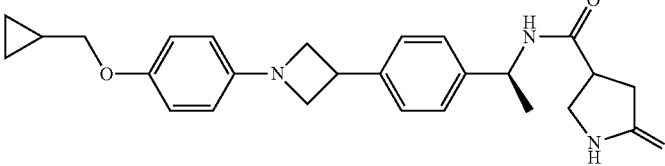 | 434 [M + H]+ | 0.61 (U) |

| Ex. | Starting material(s) | Structure | Mass spec result | HPLC retention time (method) |
|---|---|---|---|---|
| 3.35 | XVIII.1 | 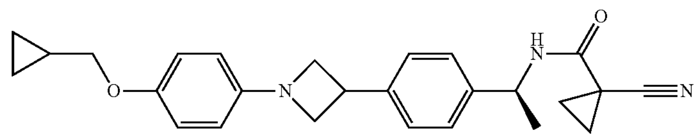 [SMILES: C[C@H](NC(=O)C1(C#N)CC1)c1ccc(C2CN(c3ccc(OCC4CC4)cc3)C2)cc1] | 416 [M + H]+ | 0.62 (U) |
| 3.36 | XVIII.1 | 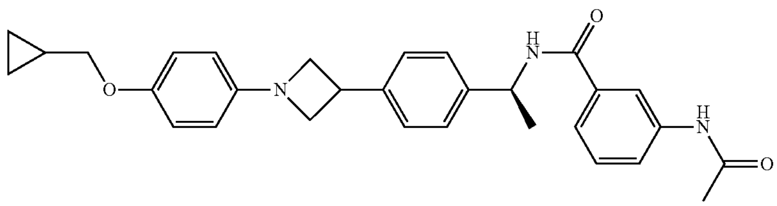 [SMILES: CC(=O)Nc1cccc(C(=O)N[C@@H](C)c2ccc(C3CN(c4ccc(OCC5CC5)cc4)C3)cc2)c1] | 484 [M + H]+ | 0.62 (U) |
| 3.37 | XVIII.1 | 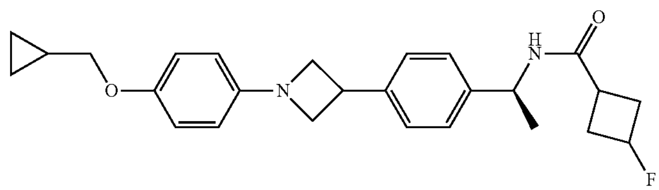 [SMILES: C[C@H](NC(=O)C1CC(F)C1)c1ccc(C2CN(c3ccc(OCC4CC4)cc3)C2)cc1] | 423 [M + H]+ | 0.62 (U) |
| 3.38 | XVIII.1 | 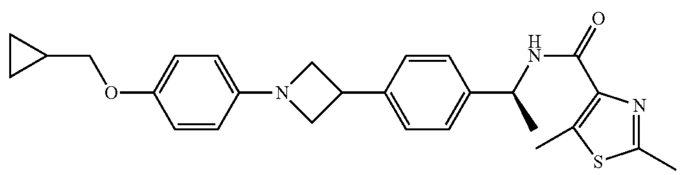 [SMILES: Cc1nc(C(=O)N[C@@H](C)c2ccc(C3CN(c4ccc(OCC5CC5)cc4)C3)cc2)c(C)s1] | 462 [M + H]+ | 0.62 (U) |
| 3.39 | XVIII.1 | 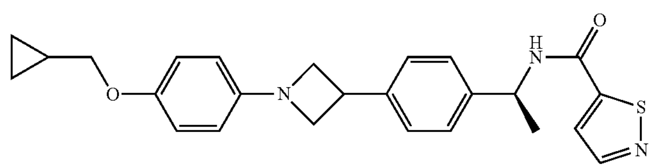 [SMILES: C[C@H](NC(=O)c1ccns1)c1ccc(C2CN(c3ccc(OCC4CC4)cc3)C2)cc1] | 434 [M + H]+ | 0.62 (U) |
| 3.40 | XVIII.1 | 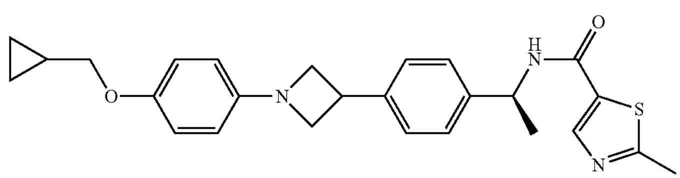 [SMILES: Cc1ncc(C(=O)N[C@@H](C)c2ccc(C3CN(c4ccc(OCC5CC5)cc4)C3)cc2)s1] | 448 [M + H]+ | 0.62 (U) |
| 3.41 | XVIII.1 | 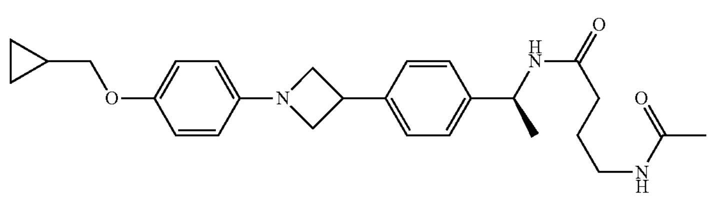 [SMILES: CC(=O)NCCCC(=O)N[C@@H](C)c1ccc(C2CN(c3ccc(OCC4CC4)cc3)C2)cc1] | 450 [M + H]+ | 0.61 (U) |
| 3.42 | XVIII.1 | 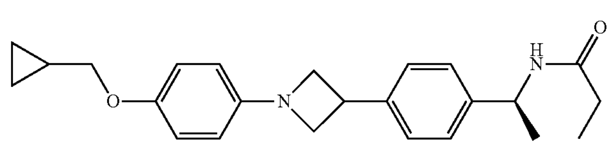 [SMILES: CCC(=O)N[C@@H](C)c1ccc(C2CN(c3ccc(OCC4CC4)cc3)C2)cc1] | 379 [M + H]+ | 0.61 (U) |

-continued

| Ex. | Starting material(s) | Structure | Mass spec result | HPLC retention time (method) |
|---|---|---|---|---|
| 3.43 | XVIII.1 | 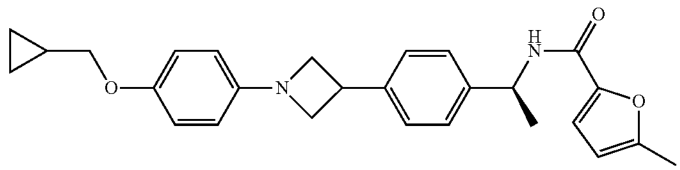 | 431 [M + H]+ | 0.63 (U) |
| 3.44 | XVIII.2 | 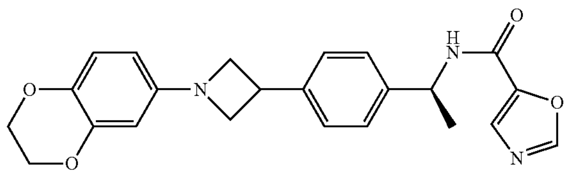 [SMILES: C[C@H](NC(=O)c1cnco1)c1ccc(C2CN(c3ccc4c(c3)OCCO4)C2)cc1] | 406 [M + H]+ | 0.62 (U) |
| 3.45 | XVIII.1 | 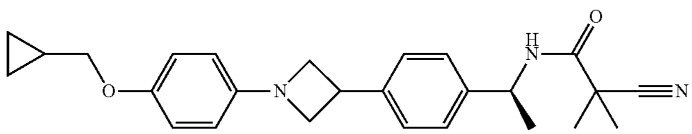 | 417 [M + H]+ | 0.64 (U) |
| 3.46 | XVIII.1 | 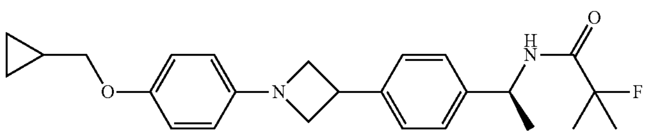 [SMILES: C[C@H](NC(=O)C(C)(C)F)c1ccc(C2CN(c3ccc(OCC4CC4)cc3)C2)cc1] | 411 [M + H]+ | 0.63 (U) |
| 3.47 | XVIII.1 | 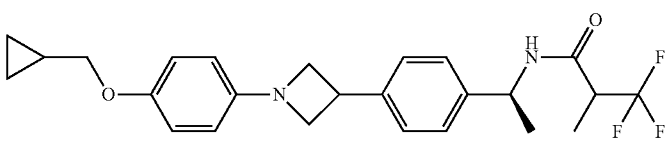 [SMILES: CC(C(=O)N[C@@H](C)c1ccc(C2CN(c3ccc(OCC4CC4)cc3)C2)cc1)C(F)(F)F] | 447 [M + H]+ | 0.63 (U) |
| 3.48 | XVIII.1 | 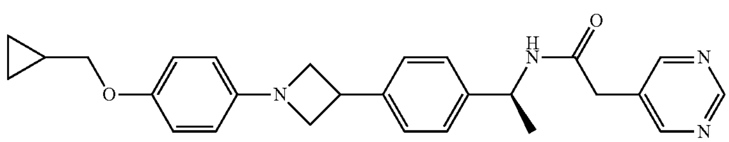 [SMILES: C[C@H](NC(=O)Cc1cncnc1)c1ccc(C2CN(c3ccc(OCC4CC4)cc3)C2)cc1] | 443 [M + H]+ | 0.62 (U) |
| 3.49 | XVIII.1 | 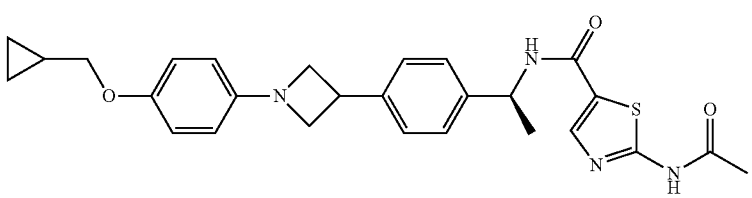 [SMILES: CC(=O)Nc1ncc(C(=O)N[C@@H](C)c2ccc(C3CN(c4ccc(OCC5CC5)cc4)C3)cc2)s1] | 491 [M + H]+ | 0.62 (U) |
| 3.50 | XVIII.1 | 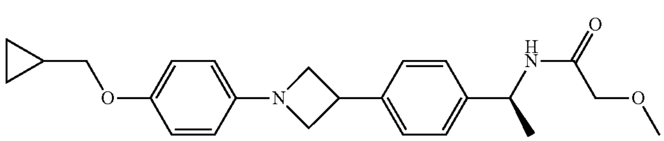 [SMILES: COCC(=O)N[C@@H](C)c1ccc(C2CN(c3ccc(OCC4CC4)cc3)C2)cc1] | 395 [M + H]+ | 0.62 (U) |
| 3.51 | XVIII.1 | 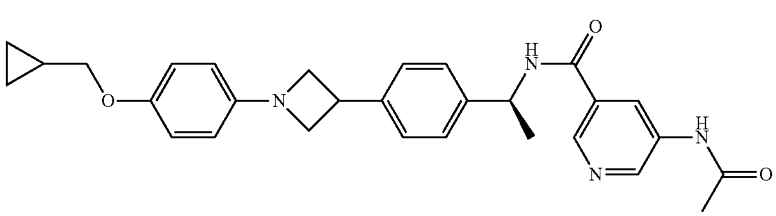 [SMILES: CC(=O)Nc1cncc(C(=O)N[C@@H](C)c2ccc(C3CN(c4ccc(OCC5CC5)cc4)C3)cc2)c1] | 485 [M + H]+ | 0.61 (U) |

| Ex. | Starting material(s) | Structure | Mass spec result | HPLC retention time (method) |
|---|---|---|---|---|
| 3.52 | XVIII.1 | 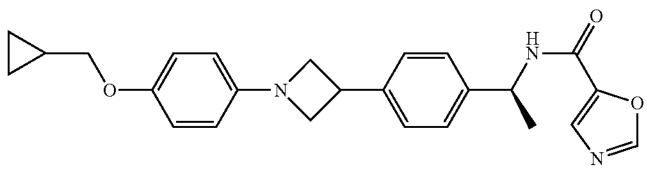 [SMILES: C[C@H](NC(=O)c1cnco1)c1ccc(C2CN(c3ccc(OCC4CC4)cc3)C2)cc1] | 418 [M + H]+ | 0.61 (U) |
| 3.53 | XVIII.1 | 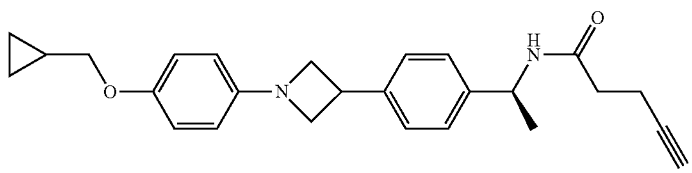 [SMILES: C#CCCC(=O)N[C@@H](C)c1ccc(C2CN(c3ccc(OCC4CC4)cc3)C2)cc1] | 403 [M + H]+ | 0.62 (U) |
| 3.54 | XVIII.1 + XIX | 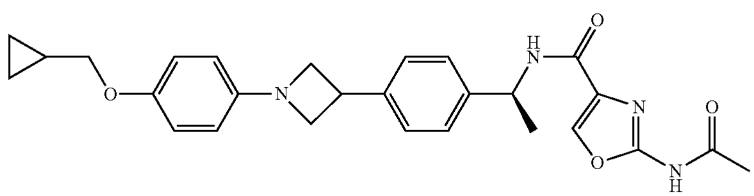 [SMILES: CC(=O)Nc1nc(C(=O)N[C@@H](C)c2ccc(C3CN(c4ccc(OCC5CC5)cc4)C3)cc2)co1] | 475 [M + H]+ | 0.61 (U) |
| 3.55 | XVIII.1 | 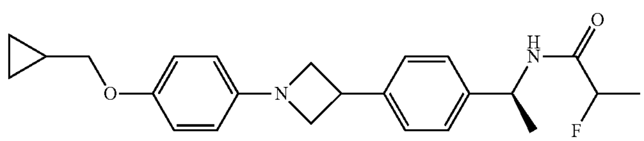 [SMILES: CC(F)C(=O)N[C@@H](C)c1ccc(C2CN(c3ccc(OCC4CC4)cc3)C2)cc1] | 397 [M + H]+ | 0.62 (U) |
| 3.56 | XVIII.1 | 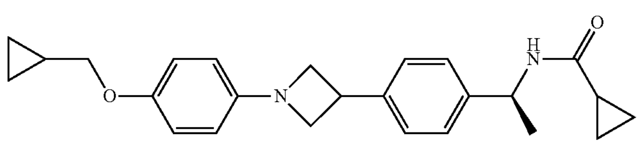 [SMILES: C[C@H](NC(=O)C1CC1)c1ccc(C2CN(c3ccc(OCC4CC4)cc3)C2)cc1] | 391 [M + H]+ | 0.62 (U) |
| 3.57 | XVIII.2 | 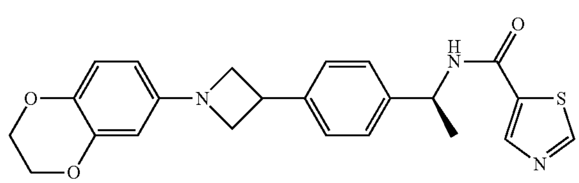 [SMILES: C[C@H](NC(=O)c1cncs1)c1ccc(C2CN(c3ccc4c(c3)OCCO4)C2)cc1] | 422 [M + H]+ | 0.62 (U) |
| 3.58 | XVIII.1 | 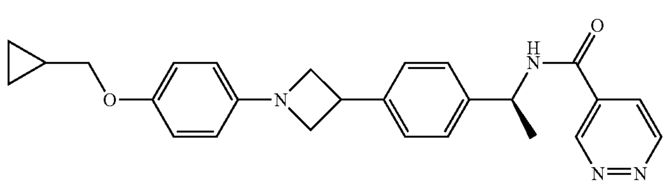 [SMILES: C[C@H](NC(=O)c1ccnnc1)c1ccc(C2CN(c3ccc(OCC4CC4)cc3)C2)cc1] | 429 [M + H]+ | 0.61 (U) |
| 3.59 | XVIII.1 | 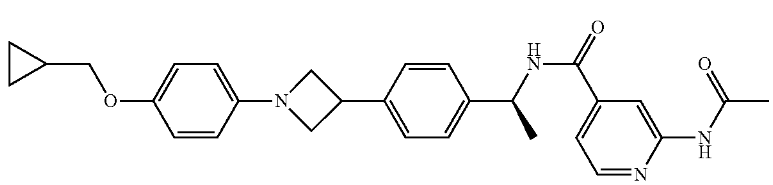 [SMILES: CC(=O)Nc1cc(C(=O)N[C@@H](C)c2ccc(C3CN(c4ccc(OCC5CC5)cc4)C3)cc2)ccn1] | 485 [M + H]+ | 0.61 (U) |
| 3.60 | XVIII.1 | 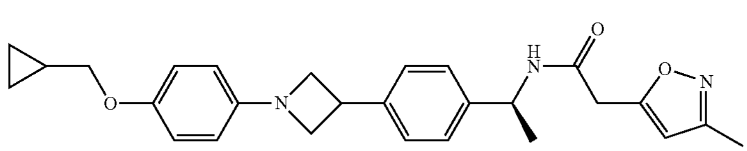 [SMILES: Cc1cc(CC(=O)N[C@@H](C)c2ccc(C3CN(c4ccc(OCC5CC5)cc4)C3)cc2)on1] | 446 [M + H]+ | 0.62 (U) |

-continued

| Ex. | Starting material(s) | Structure | Mass spec result | HPLC retention time (method) |
|---|---|---|---|---|
| 3.61 | XVIII.2 | 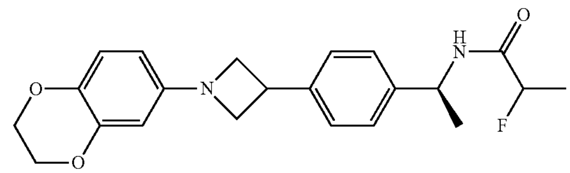 [SMILES: CC(F)C(=O)N[C@@H](C)c1ccc(C2CN(c3ccc4c(c3)OCCO4)C2)cc1] | 385 [M + H]+ | 0.64 (U) |
| 3.62 | XVIII.3 | 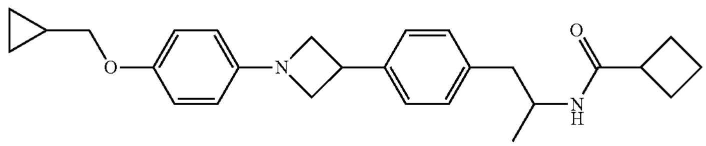 [SMILES: CC(Cc1ccc(C2CN(c3ccc(OCC4CC4)cc3)C2)cc1)NC(=O)C1CCC1] | 419 [M + H]+ | 0.65 (U) |
| 3.63 | XVIII.3 | 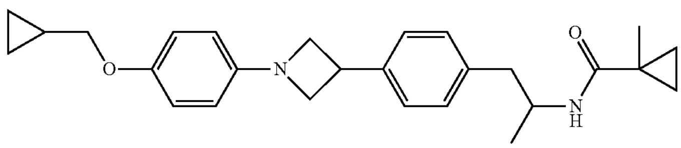 [SMILES: CC(Cc1ccc(C2CN(c3ccc(OCC4CC4)cc3)C2)cc1)NC(=O)C1(C)CC1] | 419 [M + H]+ | 0.65 (U) |
| 3.64 | XVIII.2 | 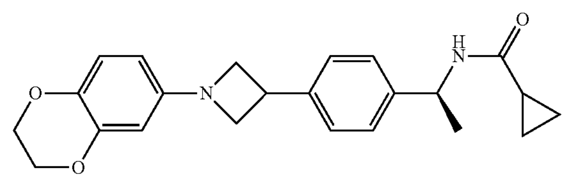 [SMILES: C[C@H](NC(=O)C1CC1)c1ccc(C2CN(c3ccc4c(c3)OCCO4)C2)cc1] | 379 [M + H]+ | 0.61 (U) |
| 3.65 | XVIII.2 | 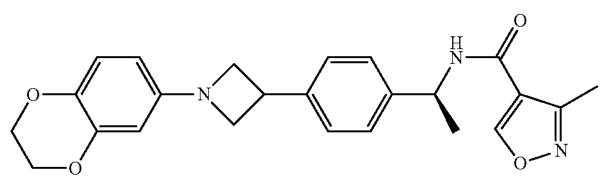 [SMILES: Cc1nocc1C(=O)N[C@@H](C)c1ccc(C2CN(c3ccc4c(c3)OCCO4)C2)cc1] | 420 [M + H]+ | 0.66 (U) |
| 3.66 | XVIII.2 | 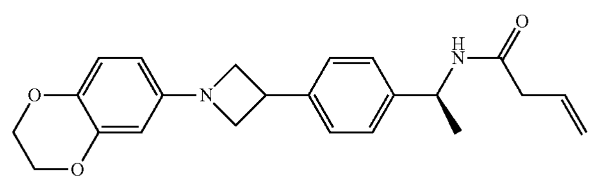 [SMILES: C=CCC(=O)N[C@@H](C)c1ccc(C2CN(c3ccc4c(c3)OCCO4)C2)cc1] | 379 [M + H]+ | 0.62 (U) |
| 3.67 | XVIII.3 | 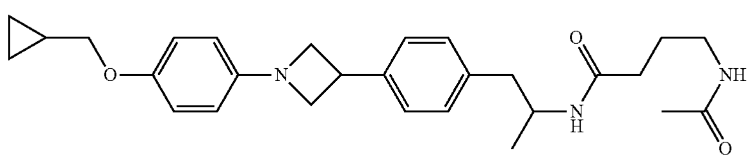 [SMILES: CC(=O)NCCCC(=O)NC(C)Cc1ccc(C2CN(c3ccc(OCC4CC4)cc3)C2)cc1] | 464.2 [M + H]+ | 0.64 (U) |
| 3.68 | XVIII.2 | Chiral | 367 [M + H]+ | 0.61 (U) |

-continued

| Ex. | Starting material(s) | Structure | Mass spec result | HPLC retention time (method) |
|---|---|---|---|---|
| 3.69 | XVIII.2 | 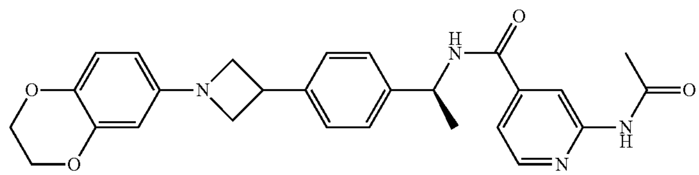 [SMILES: CC(=O)Nc1cc(C(=O)N[C@@H](C)c2ccc(C3CN(c4ccc5c(c4)OCCO5)C3)cc2)ccn1] | 473 [M + H]+ | 0.62 (U) |
| 3.70 | XVIII.2 | 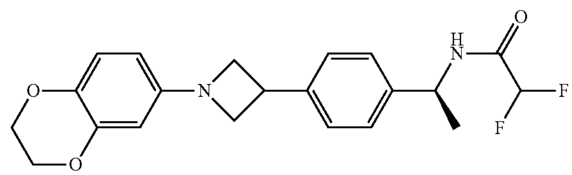 [SMILES: C[C@H](NC(=O)C(F)F)c1ccc(C2CN(c3ccc4c(c3)OCCO4)C2)cc1] | 389 [M + H]+ | 0.66 (U) |
| 3.71 | XVIII.2 | 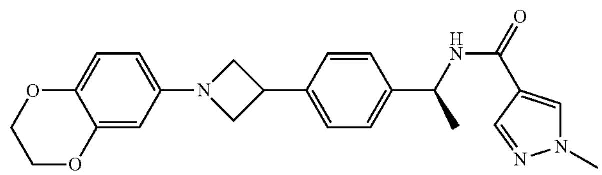 [SMILES: C[C@H](NC(=O)c1cnn(C)c1)c1ccc(C2CN(c3ccc4c(c3)OCCO4)C2)cc1] | 419 [M + H]+ | 0.63 (U) |
| 3.72 | XVIII.2 | 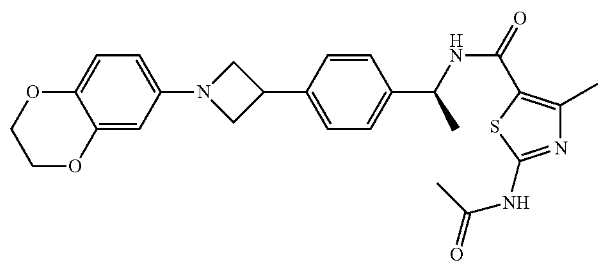 [SMILES: CC(=O)Nc1nc(C)c(C(=O)N[C@@H](C)c2ccc(C3CN(c4ccc5c(c4)OCCO5)C3)cc2)s1] | 493 [M + H]+ | 0.62 (U) |
| 3.73 | XVIII.2 | 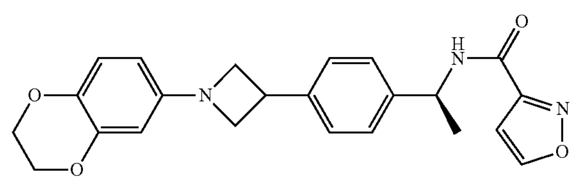 [SMILES: C[C@H](NC(=O)c1ccon1)c1ccc(C2CN(c3ccc4c(c3)OCCO4)C2)cc1] | 406 [M + H]+ | 0.64 (U) |
| 3.74 | XVIII.3 | 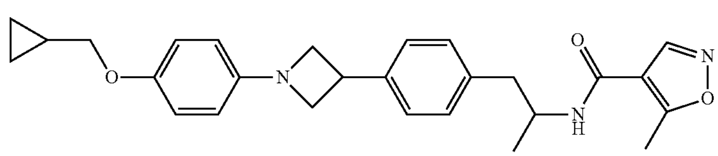 [SMILES: Cc1oncc1C(=O)NC(C)Cc1ccc(C2CN(c3ccc(OCC4CC4)cc3)C2)cc1] | 446 [M + H]+ | 0.65 (U) |
| 3.75 | XVIII.1 | 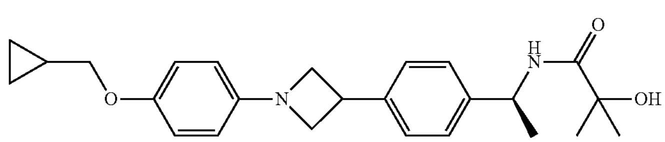 [SMILES: C[C@H](NC(=O)C(C)(C)O)c1ccc(C2CN(c3ccc(OCC4CC4)cc3)C2)cc1] | 409 [M + H]+ | 0.61 (U) |
| 3.76 | XVIII.4 | 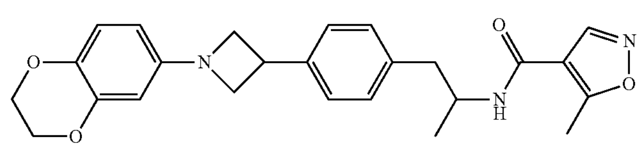 [SMILES: Cc1oncc1C(=O)NC(C)Cc1ccc(C2CN(c3ccc4c(c3)OCCO4)C2)cc1] | 434 [M + H]+ | 0.65 (U) |

| Ex. | Starting material(s) | Structure | Mass spec result | HPLC retention time (method) |
|---|---|---|---|---|
| 3.77 | XVIII.3 | 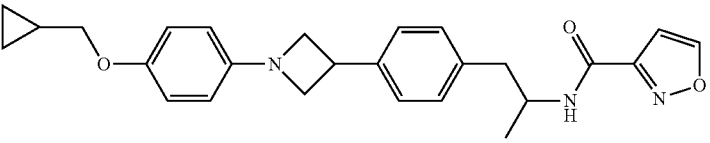 [SMILES: CC(Cc1ccc(C2CN(c3ccc(OCC4CC4)cc3)C2)cc1)NC(=O)c1ccon1] | 432 [M + H]⁺ | 0.65 (U) |
| 3.78 | XVIII.1 | 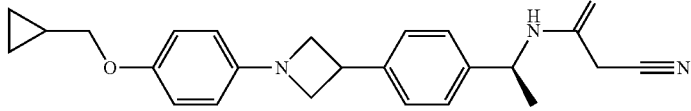 | 390 [M + H]⁺ | 0.61 (U) |
| 3.79 | XVIII.3 | 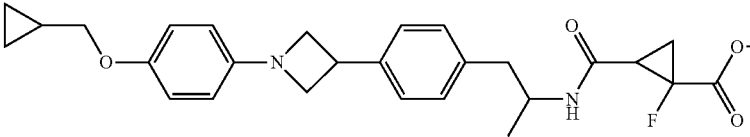 | 495 [M + H]⁺ | 0.65 (U) |
| 3.80 | XVIII.1 | 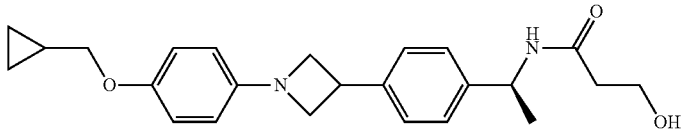 [SMILES: C[C@H](NC(=O)CCO)c1ccc(C2CN(c3ccc(OCC4CC4)cc3)C2)cc1] | 395 [M + H]⁺ | 0.61 (U) |
| 3.81 | XVIII.1 | 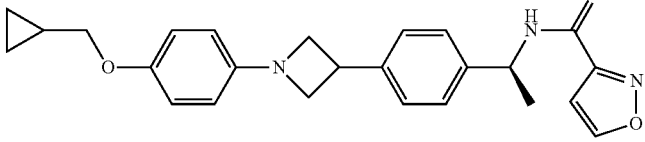 | 418 [M + H]⁺ | 0.62 (U) |
| 3.82 | XVIII.1 | 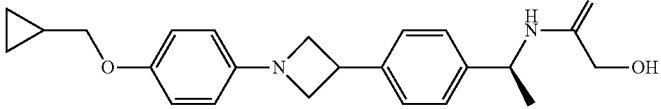 | 381 [M + H]⁺ | 0.61 (U) |
| 3.83 | XVIII.4 | 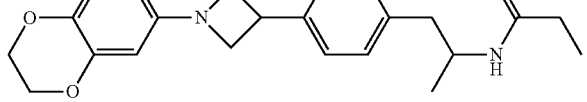 | 381 [M + H]⁺ | 0.65 (U) |
| 3.84 | XVIII.4 | 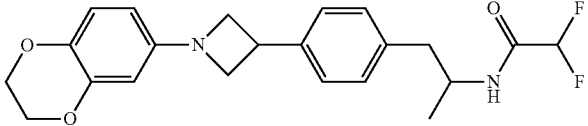 | 403 [M + H]⁺ | 0.64 (U) |
| 3.85 | XVIII.1 | 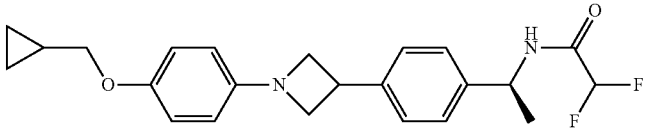 | 401 [M + H]⁺ | 0.62 (U) |
| 3.86 | XVIII.1 | 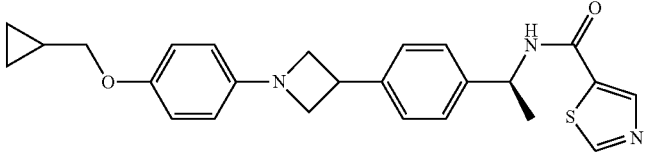 | 434 [M + H]⁺ | 0.62 (U) |

-continued

| Ex. | Starting material(s) | Structure | Mass spec result | HPLC retention time (method) |
|---|---|---|---|---|
| 3.87 | XVIII.1 | 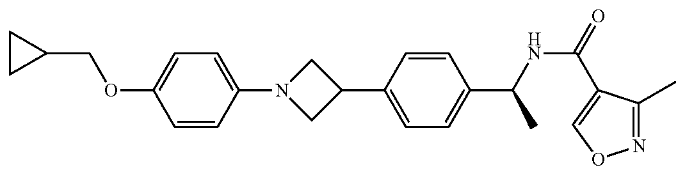 | 432 [M + H]⁺ | 0.62 (U) |
| 3.88 | XVIII.1 | 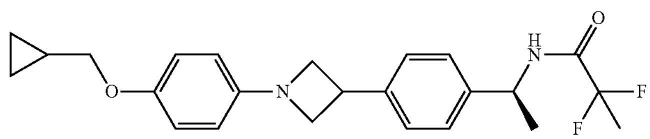 [SMILES: C[C@H](NC(=O)C(C)(F)F)c1ccc(C2CN(c3ccc(OCC4CC4)cc3)C2)cc1] | 415 [M + H]⁺ | 0.63 (U) |
| 3.89 | XVIII.1 | 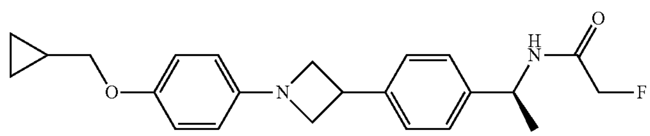 [SMILES: C[C@H](NC(=O)CF)c1ccc(C2CN(c3ccc(OCC4CC4)cc3)C2)cc1] | 383 [M + H]⁺ | 0.61 (U) |
| 3.90 | XVIII.1 | 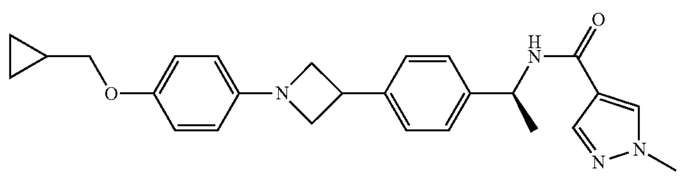 [SMILES: C[C@H](NC(=O)c1cnn(C)c1)c1ccc(C2CN(c3ccc(OCC4CC4)cc3)C2)cc1] | 431 [M + H]⁺ | 0.62 (U) |
| 3.91 | XVIII.1 | 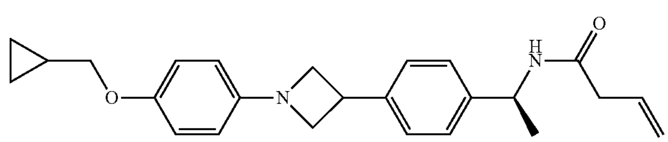 [SMILES: C=CCC(=O)N[C@@H](C)c1ccc(C2CN(c3ccc(OCC4CC4)cc3)C2)cc1] | 391 [M + H]⁺ | |

Example 4

Example 4.1 (General Route)

(S)—N-(1-(4-(1-(2-((2,2-difluoroethyl)(methyl)amino)pyrimidin-4-yl)azetidin-3-yl)phenyl)ethyl)acetamide

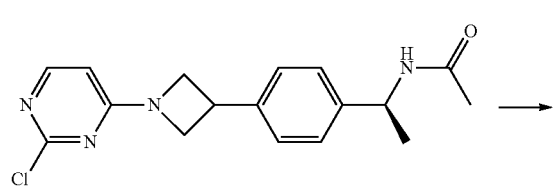

→

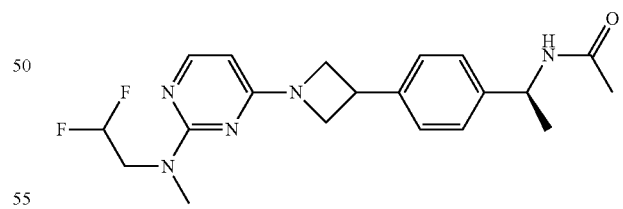

60.0 mg (0.18 mmol) of intermediate XXI.1, 47.7 mg (0.36 mmol) (2,2-difluoro-ethyl)-methyl-amine hydrochloride and 0.16 mL (0.91 mmol) DIPEA are added to 2 mL NMP and stirred at 200° C. for 3 h in a microwave oven. Afterwards the reaction mixture is directly purified by HPLC (ACN/H₂O/NH₃).

$C_{20}H_{25}F_2N_5O$ (M=389.4 g/mol)

ESI-MS: 390 [M+H]⁺

R$_t$ (HPLC): 0.85 min (method X)

The following compounds are prepared analogously to example 4.1.

| Ex. | Starting materia | Structure | Mass spec result | HPLC retention time (method) |
|---|---|---|---|---|
| 4.1 | XXI.1 | 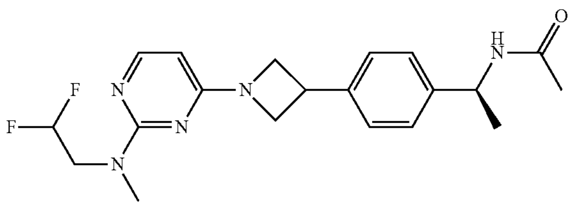 [SMILES: CC(=O)N[C@@H](C)c1ccc(C2CN(c3ccnc(N(C)CC(F)F)n3)C2)cc1] | 390 [M + H]⁺ | 0.85 (X) |
| 4.2 | XXI.2 | 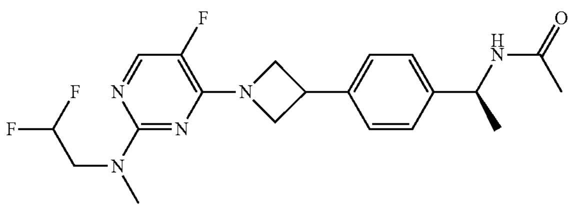 | 408 [M + H]⁺ | 0.90 (X) |
| 4.3 | XXI.2 | 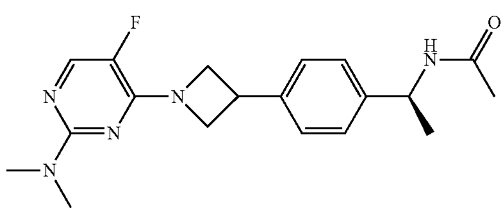 [SMILES: CC(=O)N[C@@H](C)c1ccc(C2CN(c3nc(N(C)C)ncc3F)C2)cc1] | 358 [M + H]⁺ | 0.85 (X) |

Example 5

Example 5.1 (general route)

N-((1S)-1-(4-(1-(2-((2,2-difluorocyclopropyl)meth-oxy)-3-fluoropyridin-4-yl)azetidin-3-yl)phenyl)ethyl)acetamide

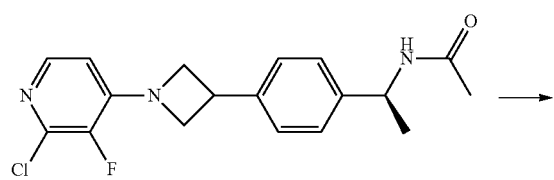

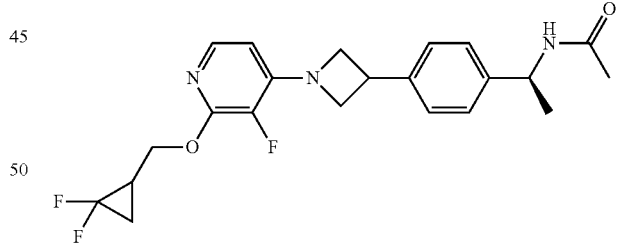

To 30.0 mg (0.09 mmol) of intermediate XXI.5 and 93.2 mg (0.86 mmol) (2,2-difluorocyclopropyl)methanol in 4 mL dioxane are added 17.3 mg (0.43 mmol) NaH and the resulting mixture is stirred at 130° C. over night in a sealed vial. Afterwards the solvent is removed in vacuo. The residue is taken up in DMF and purified by HPLC (ACN/H$_2$O/TFA).

$C_{22}H_{24}F_3N_3O_2$ (M=419.4 g/mol)

ESI-MS: 420 [M+H]⁺

R$_t$ (HPLC): 0.97 min (method W)

The following compounds are prepared analogously to example 5.1.

For the examples 5.6 and 5.7 THF is used as solvent.

The following compounds are prepared analogously to example 3.1.

For example 3.4 the reaction mixture is stirred at 60° C. over night.

| Ex. | Starting material | Structure | Mass spec result | HPLC retention time (method) |
|---|---|---|---|---|
| 5.1 | XXI.5 | 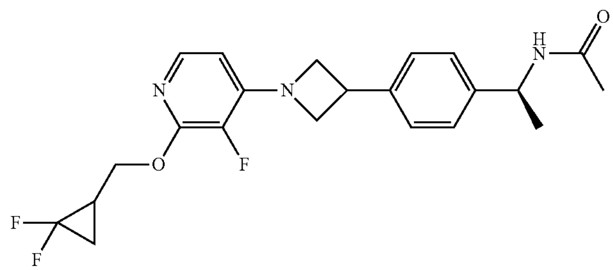 [SMILES: CC(=O)N[C@@H](C)c1ccc(C2CN(c3ccnc(OCC4CC4(F)F)c3F)C2)cc1] | 420 [M + H]⁺ | 0.97 (W) |
| 5.2 | XXI.3 | 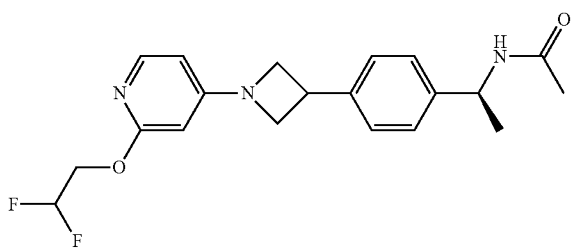 [SMILES: CC(=O)N[C@@H](C)c1ccc(C2CN(c3ccnc(OCC(F)F)c3)C2)cc1] | 376 [M + H]⁺ | 0.77 (W) |
| 5.3 | XXI.3 | 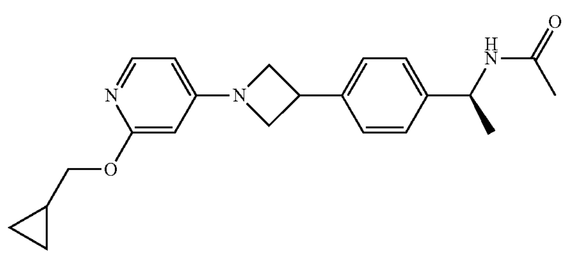 [SMILES: CC(=O)N[C@@H](C)c1ccc(C2CN(c3ccnc(OCC4CC4)c3)C2)cc1] | 366 [M + H]⁺ | 0.83 (W) |
| 5.4 | XXI.6 | 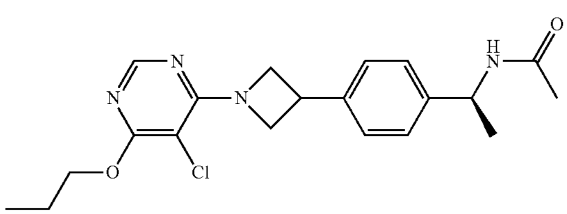 [SMILES: CCCOc1ncnc(N2CC(c3ccc([C@H](C)NC(C)=O)cc3)C2)c1Cl] | 389 [M + H]⁺ | 1.08 (W) |
| 5.5 | XXI.6 | 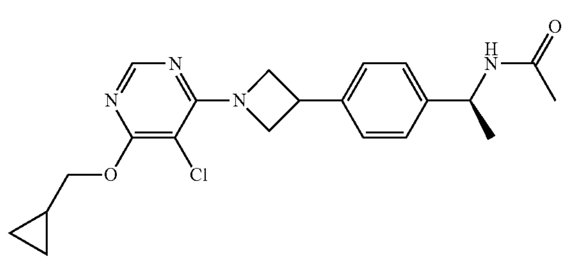 [SMILES: CC(=O)N[C@@H](C)c1ccc(C2CN(c3ncnc(OCC4CC4)c3Cl)C2)cc1] | 401 [M + H]⁺ | 1.08 (W) |

-continued

| Ex. | Starting material | Structure | Mass spec result | HPLC retention time (method) |
|---|---|---|---|---|
| 5.6 | XXI.4 | 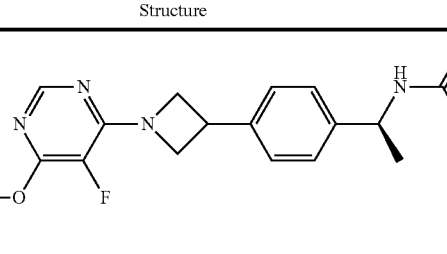 | 421 [M + H]+ | 1.02 (W) |
| 5.7 | XXI.4 | 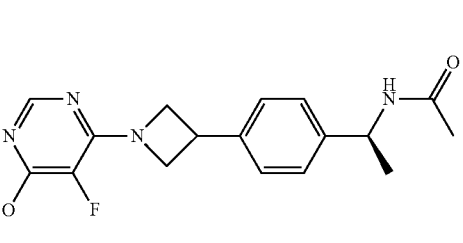 | 385 [M + H]+ | 0.94 (W) |

Analytic methods

Method A

| time (min) | Vol % water (incl. 0.2% NH₄OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters); 2.5 μm; 3.0×30 mm; column temperature: 40° C.; flow: 1.3 mL/min;

Method B

| time (min) | Vol % water (incl. 0.1% FA) | Vol % acetonitrile (incl. 0.1% FA) |
|---|---|---|
| 0.0 | 95 | 5 |
| 0.1 | 95 | 5 |
| 3.1 | 2 | 98 |
| 4.5 | 2 | 98 |
| 5.0 | 95 | 5 |

Analytical column: X-terra™ MS C18 (Waters); 2.5 μm; 4.6×30 mm; column temperature: rt; flow: 1.0 mL/min; detection 210-420 nm.

Method C

| time (min) | Vol % water (incl. 0.1% FA) | Vol % methanol (incl. 0.1% FA) |
|---|---|---|
| 0.0 | 90 | 10 |
| 2.5 | 2 | 98 |
| 6.0 | 2 | 98 |

Method D

| time (min) | Vol % water (incl. 0.2% FA) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Method E

| time (min) | Vol % water (incl. 0.1% TFA) | Vol % methanol |
|---|---|---|
| 0.0 | 80 | 20 |
| 1.7 | 0 | 100 |
| 2.5 | 0 | 100 |
| 2.6 | 80 | 20 |

Analytical column: Sunfire C18 (Waters); 3.5 μm; 4.6×50 mm; column temperature: 60° C.; flow: 2 mL/min;

Method F

| time (min) | Vol % water (incl. 0.2% NH4OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: Gemini C18 (Phenomenex); 2.5 μm; 3.0×30 mm; column temperature: 40° C.; flow: 1.3 mL/min

Method G

| time (min) | Vol % water (incl. 0.2% NH4OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters); 2.5 μm; 3.0×30 mm; column temperature: 60° C.; flow: 1.3 mL/min;

Method H

| time (min) | Vol % water (incl. 0.05% TFA) | Vol % ACN |
|---|---|---|
| 0.0 | 40 | 60 |
| 6 | 10 | 90 |
| 15 | 10 | 90 |
| 15.1 | 40 | 60 |

Analytical column: XBridge C18 (Waters) 3.5 μm; 4.6×50 mm; column temperature: r.t.;

Method I

| time (min) | Vol % water (incl. 0.01M NH4OAc) | Vol % ACN |
|---|---|---|
| 0.0 | 50 | 50 |
| 6 | 10 | 90 |
| 15 | 10 | 90 |
| 15.1 | 40 | 60 |

Analytical column: Eclipse-XDB-C18 (Agilent), 5.0 μm; 4.6×150 mm; column temperature: r.t.; flow: 1.0 ml/min.

Method J

| time (min) | Vol % water (incl. 0.01M NH4OAc) | Vol % ACN |
|---|---|---|
| 0.0 | 70 | 30 |
| 8 | 10 | 90 |
| 15 | 10 | 90 |
| 15.1 | 70 | 30 |

Analytical column: XBridge C8 (Waters) 5.0 μm; 4.6×150 mm; column temperature: r.t.; flow: 1 ml/min.

Method K

| time (min) | Vol % water (incl. 0.2% $NH_4OH$) | Vol % MeOH |
|---|---|---|
| 0.0 | 95 | 5 |
| 0.05 | 95 | 5 |
| 1.40 | 0 | 100 |
| 1.80 | 0 | 100 |

Analytical column: XBridge C18 (Waters) 2.5 μm; 3.0×30 mm; column temperature: 60° C.; flow: 2.2 ml/min.

Method L

| time (min) | Vol % water (incl. 0.2% NH4OH) | Vol % MeOH |
|---|---|---|
| 0.0 | 95 | 5 |
| 1.0 | 10 | 90 |
| 2.2 | 10 | 90 |
| 2.3 | 0 | 100 |
| 2.5 | 0 | 100 |

Analytical column: XBridge C18 (Waters) 2.5 μm; 3.0×30 mm; column temperature: 40° C.; flow: 1.3 ml/min.

Method M

| time (min) | Vol % water (incl. 0.2% TFA) | Vol % MeOH |
|---|---|---|
| 0.00 | 95 | 5 |
| 0.05 | 95 | 5 |
| 1.40 | 0 | 100 |
| 1.80 | 0 | 100 |

Analytical column: Sunfire C18 (Waters) 2.5 μm; 3.0×30 mm; column temperature: 60° C.; flow: 2.2 ml/min.

Method N

| time (min) | Vol % water (incl. 0.1% $NH_4OH$) | Vol % MeOH | Flow [ml/min] |
|---|---|---|---|
| 0.0 | 95 | 5 | 2.2 |
| 0.30 | 95 | 5 | 2.2 |
| 1.50 | 0 | 100 | 2.2 |
| 1.55 | 0 | 100 | 2.9 |
| 1.70 | 0 | 100 | 2.9 |

Analytical column: XBridge C18 (Waters) 2.5 μm; 3.0×30 mm; column temperature: 60° C.

Method O

| time (min) | Vol % water (incl. 0.1% NH4OH) | Vol % MeOH |
|---|---|---|
| 0.0 | 95 | 5 |
| 0.15 | 95 | 5 |
| 1.70 | 0 | 100 |
| 2.10 | 0 | 100 |

Analytical column: XBridge C18 (Agilent) 3.5 μm; 4.6×30 mm; column temperature: 60° C.; flow: 4 ml/min

Method P

| time (min) | Vol % water (incl. 0.15% TFA) | Vol % MeOH |
|---|---|---|
| 0.00 | 95 | 5 |
| 0.25 | 95 | 5 |
| 1.90 | 0 | 100 |
| 2.05 | 0 | 100 |

Analytical column: Microsorb C18 (Waters) 5 μm; 4.6×20 mm; column temperature: r.t.; flow: 5.2 ml/min.

Method Q

| time (min) | Vol % water (incl. 0.05% TFA) | Vol % ACN |
|---|---|---|
| 0.0 | 70 | 30 |
| 8 | 10 | 90 |
| 15 | 10 | 90 |
| 15.1 | 70 | 30 |

Analytical column: XBridge C18 (Waters) 3.5 μm; 4.6×150 mm; column temperature: r.t.; flow: 1 ml/min.

Method R

| time (min) | Vol % water (incl. 0.1% FA) | Vol % ACN |
|---|---|---|
| 0.0 | 40 | 60 |
| 4 | 10 | 90 |
| 15 | 10 | 90 |
| 15.1 | 10 | 60 |

Analytical column: Symmetry C18 (Waters) 3.5 μm; 4.6×75 mm; column temperature: r.t.; flow: 1 ml/min.

Method S

| time (min) | Vol % water (incl. 0.1% TFA) | Vol % ACN (incl. 0.1% TFA) |
|---|---|---|
| 0.0 | 95 | 5 |
| 2.0 | 0 | 100 |
| 2.49 | 0 | 100 |
| 2.50 | 95 | 5 |

Analytical column: Sunfire C18 (Waters) 3.5 μm; 4.6×50 mm; column temperature: 40° C.; flow: 1.5 ml/min.

Method T

| time (min) | Vol % water (incl. 0.1% TFA) | Vol % MeOH | Flow [ml/min] |
|---|---|---|---|
| 0.0 | 95 | 5 | 1.8 |
| 0.25 | 95 | 5 | 1.8 |
| 1.70 | 0 | 100 | 1.8 |
| 1.75 | 0 | 100 | 2.5 |
| 1.90 | 0 | 100 | 2.5 |

Analytical column: Sunfire C18 (Waters) 2.5 μm; 3.0×30 mm; column temperature: 60° C.;

Method U

| time (min) | Vol % water (incl. 0.1% TFA) | Vol % MeOH | Flow [ml/min] |
|---|---|---|---|
| 0.0 | 95 | 5 | 1.5 |
| 0.7 | 1 | 99 | 1.5 |
| 0.8 | 1 | 99 | 1.5 |
| 0.81 | 95 | 5 | 1.5 |

Analytical column: Ascentis Express C18 (Supelco) 2.7 μm; 2.1×50 mm; column temperature: 60° C.;

Method V

| time (min) | Vol % water (incl. 0.1% FA) | Vol % ACN | Flow [ml/min] |
|---|---|---|---|
| 0.0 | 95 | 5 | 3.0 |
| 0.3 | 95 | 5 | 3.0 |
| 2.0 | 2 | 98 | 3.0 |
| 2.4 | 2 | 98 | 3.0 |
| 2.45 | 95 | 5 | 3.0 |
| 2.8 | 95 | 5 | 3.0 |

Analytical column: Pursuit XRS C18 (Varian) 5.0 μm; 4.6×50 mm; column temperature: r.t.;

Method W

| time (min) | Vol % water (incl. 0.1% TFA) | Vol % ACN | Flow [ml/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stablebond C18 (Agilent) 1.8 μm; 3.0×30 mm; column temperature: 60° C.

Method X

| time (min) | Vol % water (incl. 0.1% NH$_4$OH) | Vol % ACN | Flow [ml/min] |
|---|---|---|---|
| 0.00 | 97 | 3 | 2.2 |
| 0.20 | 97 | 3 | 2.2 |

-continued

| Method X | | | |
|---|---|---|---|
| time (min) | Vol % water (incl. 0.1% NH$_4$OH) | Vol % ACN | Flow [ml/min] |
| 1.20 | 0 | 100 | 2.2 |
| 1.25 | 0 | 100 | 3.0 |
| 1.40 | 0 | 100 | 3.0 |

Analytical column: XBridge C18 (Waters) 2.5 μm; 3.0×30 mm; column temperature: 60° C.

Method AA (GC Method)

Analytical column: SLB-5MS 15 m, ID 100 μM, df 0.10 μM.

Average velocity 45 cm/s, carrier gas:He, split ratio: 300:1, injector temp: 250° C., injection volume: 1 μL.

Initial temp: 60° C., initial time: 1.0 min, solvent delay: 0.6 min, rate: 50° C./min, final temp: 250° C., final time: 1.0 min.

The invention claimed is:

1. A compound of the formula I

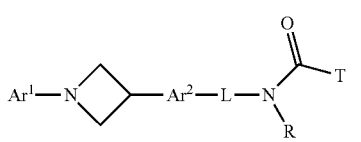

(I)

wherein

Ar$^1$ is selected from a group consisting of:
  6- to 10-membered aryl and 5- to 10-membered heteroaryl, which substituted with one or more substituents R$^1$,
    wherein two substituents R$^1$ linked to adjacent C-atoms of Ar$^1$ together may form a C$_{3-5}$-alkylene bridge, in which 1, 2 or 3 CH$_2$-groups may be replaced by O, C(=O), S, S(=O), S(=O)$_2$, NH or N(C$_{1-4}$-alkyl),
    and wherein the alkylene bridge may optionally be substituted by one or two C$_{1-3}$-alkyl groups;

R$^1$ is selected from a group consisting of:
  H, F, Cl, Br, I, CN, OH, —NO$_2$, C$_{1-6}$-alkyl, C$_{2-6}$-alkenyl, C$_{2-6}$-alkynyl, C$_{3-10}$-carbocyclyl, C$_{3-10}$-carbocyclyl-C$_{1-3}$-alkyl, C$_{1-6}$-alkyl-O—, C$_{3-6}$-alkenyl-O—, C$_{3-6}$-alkynyl-O—, C$_{3-10}$-carbocyclyl-O—, C$_{3-10}$-carbocyclyl-C$_{1-3}$-alkyl-O—, C$_{1-6}$-alkyl-S—, C$_{1-6}$-alkyl-S(=O)—, C$_{1-6}$-alkyl-S(=O)$_2$—, C$_{3-10}$-carbocyclyl-S—, C$_{3-10}$-carbocyclyl-C$_{1-3}$-alkyl-S—, C$_{1-4}$-alkyl-C(=O)—, C$_{3-10}$-carbocyclyl-C(=O)—, R$^3$R$^4$N—, R$^3$R$^4$N—C$_{2-3}$-alkyl-O—, R$^3$R$^4$N—C(=O)—, R$^3$R$^4$N—S(=O)$_2$—, C$_{1-6}$-alkyl-C(=O)—NR$^3$—, C$_{1-6}$-alkyl-S(=O)$_2$—NR$^3$—, C$_{1-6}$-alkyl-C(=O)—NR$^3$—C$_{1-3}$-alkyl-, HO—C(=O)—, C$_{1-6}$-alkyl-O—C(=O)—, heterocyclyl, heterocyclyl-O—, heterocyclyl-C$_{1-3}$-alkyl, heterocyclyl-C$_{1-3}$-alkyl-O—, heterocyclyl-C(=O)—, heterocyclyl-NR$^4$—, aryl, aryl-C$_{1-3}$-alkyl, aryl-O—, aryl-C$_{1-3}$-alkyl-O—, heteroaryl, heteroaryl-C$_{1-3}$-alkyl, heteroaryl-O— and heteroaryl-C$_{1-3}$-alkyl-O—,
    wherein in each carbocyclyl and heterocyclyl a CH$_2$-group may be replaced by —C(=O)—, —C=CH$_2$—, —C=CH(C$_{1-6}$-alkyl)- or —C=C(C$_{1-6}$-alkyl)$_2$-,
    wherein each carbocyclyl and heterocyclyl may be substituted with one or more C$_{1-4}$-alkyl, which may be substituted with one or more substituents R$^2$,
    wherein each alkyl, carbocyclyl and heterocyclyl may be substituted with one or more substituents R$^2$,
    wherein each heterocyclyl may be substituted with aryl or heteroaryl, and
    wherein each aryl and heteroaryl group may be substituted with one or more substituents R$^5$;

R$^2$ is selected from a group consisting of:
  F, Cl, Br, CN, OH, C$_{1-4}$-alkyl-O—, C$_{3-7}$-cycloalkyl-O—, C$_{3-7}$-cycloalkyl-C$_{1-3}$-alkyl-O—, H$_2$N—, (C$_{1-4}$-alkyl)NH—, (C$_{1-4}$-alkyl)$_2$N—, C$_{1-4}$-alkyl-C(=O)—, C$_{1-4}$-alkyl-S(=O)$_2$—, HO—C(=O)— and C$_{1-4}$-alkyl-O—C(=O)—,
    wherein each alkyl or cycloalkyl may be substituted with one or more substituents independently selected from F and OH; and R$^3$ is selected from a group consisting of:
  H, C$_{1-6}$-alkyl, C$_{3-10}$-carbocyclyl, C$_{3-10}$-carbocyclyl-C$_{1-3}$-alkyl, C$_{3-6}$-alkenyl, C$_{3-6}$-alkynyl, heterocyclyl, heterocyclyl-C$_{1-3}$-alkyl, aryl, aryl-C$_{1-3}$-alkyl, heteroaryl and heteroaryl-C$_{1-3}$-alkyl,
    wherein each carbocyclyl and heterocyclyl may be substituted with one or more C$_{1-4}$-alkyl,
    wherein in each carbocyclyl and heterocyclyl one CH$_2$-group may be replaced by —C(=O)—, and
    wherein each alkyl, carbocyclyl, heterocyclyl, aryl and heteroaryl group may be substituted with one or more substituents R$^5$, R$^4$ is H or C$_{1-6}$-alkyl; and Ar$^2$ is
  phenylene;
  and R$^5$ is selected from a group consisting of:
  F, Cl, Br, CN, OH, C$_{1-4}$-alkyl-, C$_{1-4}$-alkyl-O—, C$_{1-4}$-alkyl-S—, C$_{1-4}$-alkyl-S(=O)$_2$—, C$_{1-3}$-alkyl-O—(C=O)—, H$_2$N—, (C$_{1-4}$-alkyl)NH—, (C$_{1-4}$-alkyl)$_2$N—, C$_{1-4}$-alkyl-C(=O)—NH—, C$_{1-4}$-alkyl-C(=O)—N(C$_{1-4}$ alkyl)- and heterocyclyl,
    wherein each alkyl may be optionally substituted with one or more F-atoms and/or with a substituent selected from OH, C$_{1-3}$-alkyl-O— and CN;

L is
  a straight chain C$_{1-4}$-alkylene group which is optionally substituted with one or more C$_{1-3}$-alkyl or C$_{1-3}$-alkyl-O—C$_{1-3}$-alkyl groups,
    wherein two alkyl substituents together may form a C$_{1-5}$-alkylene bridge in which 1 or 2-CH$_2$-groups may be replaced by a group independently selected from 0, S, NH or N(C$_{1-4}$-alkyl)-, and wherein the C$_{1-5}$-alkylene bridge is optionally substituted by 1 or 2 C$_{1-3}$-alkyl groups; and R is H; and T is selected from a group consisting of:
  C$_{1-6}$-alkyl, C$_{2-6}$-alkenyl, C$_{2-6}$-alkynyl, C$_{3-10}$-carbocyclyl, C$_{3-10}$-carbocyclyl-C$_{1-3}$-alkyl, C$_{1-6}$-alkyl-O—, C$_{3-10}$-carbocyclyl-O—, C$_{3-10}$-carbocyclyl-C$_{1-3}$-alkyl-O—, C$_{1-6}$-alkyl-S—, C$_{3-10}$-carbocyclyl-S—, C$_{3-10}$-carbocyclyl-C$_{1-3}$-alkyl-S—, C$_{1-4}$-alkyl-C(=O)—, C$_{1-4}$-alkyl-S(=O)$_2$—, R$^3$R$^4$—N—, R$^3$R$^4$—N—C$_{1-3}$-alkyl-, R$^3$R$^4$—N—CO—, C$_{1-4}$-alkyl-C(=O)—R$^4$N—C$_{1-3}$-alkyl, heterocyclyl, heterocyclyl-C$_{1-3}$-alkyl-, aryl, aryl-C$_{1-3}$-alkyl-, heteroaryl-C$_{1-3}$-alkyl- and heteroaryl,
    wherein in each carbocyclyl and heterocyclyl a CH$_2$-group may be replaced by —C(=O)—, wherein each carbocyclyl and heterocyclyl may be substituted with one or more $C_{1-4}$-alkyl, which may be substituted with one or more substituents $R^2$, wherein each alkyl, carbocyclyl and heterocyclyl may be substituted with one or more substituents $R^2$, and wherein each aryl and heteroaryl group may be substituted with one or more substituents $R^5$, or any tautomers and stereoisomers thereof, or a pharmaceutically acceptable salt thereof.

2. A compound according to claim 1, wherein L is a straight chain $C_{1-3}$-alkylene group which is optionally substituted with one methyl group.

3. A compound according to claim 1, wherein
$Ar^1$ is selected from the group consisting of:
phenyl, thiadiazolyl, pyridinyl, pyrimidinyl, pyridazinyl, quinolinyl, oxazolo[4,5-d]pyrimidinyl, 2,3-dihydro-benzo[1,4]dioxinyl and 3,4-dihydro-2H-benzo[b][1,4]dioxepinyl, wherein $Ar^1$ may be substituted with one or two substituents $R^1$.

4. A compound according to claim 3, wherein
$Ar^1$ is

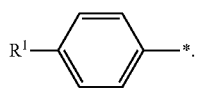

5. A compound according to claim 1, wherein
$R^1$ is selected from a group consisting of:
F, Cl, Br, $C_{1-4}$-alkyl, $C_{3-5}$-cycloalkyl, $C_{1-4}$-alkyl-O—, $C_{3-6}$-cycloalkyl-O—, $C_{3-5}$-cycloalkyl-CH$_2$—O—, $H_2N$—, thiophenyl and phenyl, wherein each alkyl and cycloalkyl group may be substituted by one to three F; and wherein in the NH$_2$-group, one or both hydrogen atoms may independently be replaced by $C_{1-4}$-alkyl or $C_{3-5}$-cycloalkyl, wherein each alkyl and cycloalkyl group may be substituted by one or more F; and wherein each phenyl group may be substituted by Cl or —OCH$_3$.

6. A compound according to claim 1, wherein
T is selected from a group consisting of:
$C_{1-3}$-alkyl, —O—($C_{1-2}$-alkyl), —NH—($C_{1-2}$-alkyl), —N($C_{1-2}$-alkyl)$_2$, $C_{3-5}$-cycloalkyl, $C_{3-5}$-cycloalkenyl, $C_{2-6}$-alkenyl, $C_{2-6}$-alkinyl, heterocyclyl, phenyl, heteroaryl and heteroaryl-CH$_2$—, wherein the heterocyclyl group is selected from the group consisting of: pyrrolidinyl, tetrahydrofuranyl, piperidinyl, and tetrahydropyranyl; and wherein each heteroaryl group is selected from the group consisting of:
pyrrolyl, furanyl, oxazolyl, isoxazolyl, thiazolyl, isothiazolyl, pyrazolyl, imidazolyl, triazolyl, pyridinyl, pyrimidinyl, pyrazinyl and pyridyzinyl; and wherein in heterocyclyl a —CH$_2$-group may optionally be replaced by —C(═O)—; and wherein each alkyl, cycloalkyl, heterocyclyl, phenyl and heteroaryl may be optionally substituted with one to three groups independently selected from the group consisting of: F, CN, OH, $C_{1-3}$-alkyl-, $C_{1-3}$-alkyl-O— and $CH_3$—C(═O)—NH—.

7. A compound according to claim 6, wherein T is $CH_3$, cyclopropyl or heteroaryl, wherein the heteroaryl group is selected from the group consisting of:
oxazolyl, isoxazolyl, thiazolyl, isothiazolyl and pyrazolyl; and wherein and heteroaryl group may be optionally substituted with one or two groups independently selected from the group consisting of: $CH_3$, and $CH_3$—C(═O)—NH—.

8. A compound according to claim 1 having the formula

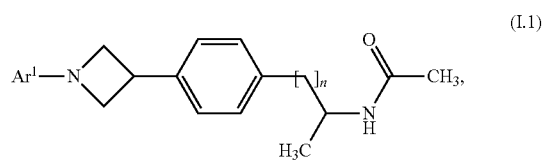

(I.1)

wherein
n is 0, 1 or 2; and
$Ar^1$ is selected from a group consisting of:
phenyl, pyridinyl, pyrimidinyl, pyridazinyl,

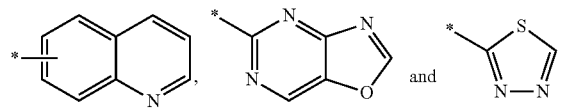

wherein each $Ar^1$ group is optionally substituted by 1 or 2 $R^1$ and $R^1$ is selected from a group consisting of:
F, Cl, Br, straight-chained or branched $C_{1-4}$-alkyl, cyclopropyl, $C_{3-5}$-cycloalkyl-O—, $C_{3-5}$-cycloalkyl-NH—, cyclopropyl-CH$_2$—O—, $R^3R^4N$, phenyl, thiophenyl, wherein two $R^1$ groups that are attached to adjacent C-atoms together may form a —O—CH$_2$—CH$_2$—O— or —O—CH$_2$—CH$_2$—CH$_2$—O— bridge, wherein $R^3$ is H or $C_{1-4}$-alkyl, and
$R^4$ is H or $C_{1-3}$-alkyl, wherein the phenyl group in $R^1$ is optionally substituted by Cl or —O—($C_{1-3}$-alkyl); and wherein the alkyl and cycloalkyl groups in $R^1$ may each be substituted by one or more F atoms, or a pharmaceutically acceptable salt thereof.

9. A method for treating obesity or type 2 diabetes which comprises administering to a host suffering from obesity or type 2 diabetes a therapeutically effective amount of a compound according to claim 1.

10. A pharmaceutical composition comprising a compound according to claim 1 and a pharmaceutically acceptable carrier or diluent.

* * * * *